(12) United States Patent
Shalman et al.

(10) Patent No.: US 6,471,656 B1
(45) Date of Patent: Oct. 29, 2002

(54) METHOD AND SYSTEM FOR PRESSURE BASED MEASUREMENTS OF CFR AND ADDITIONAL CLINICAL HEMODYNAMIC PARAMETERS

(75) Inventors: Evgeny Shalman, Tel Aviv; Elhanan Dgany, Kfar Saba; Chen Barak, Shoham; Simon Henri Noskowicz, Kfar Saba, all of (IL)

(73) Assignee: Florence Medical Ltd, Kfar Saba (IL)

( * ) Notice: Subject to any disclaimer, the term of this patent is extended or adjusted under 35 U.S.C. 154(b) by 0 days.

(21) Appl. No.: 09/344,505

(22) Filed: Jun. 25, 1999

(51) Int. Cl.$^7$ ................................................ A61N 5/00
(52) U.S. Cl. ..................... 600/486; 600/505; 600/561
(58) Field of Search ........................... 600/345, 366, 600/373–374, 381, 403, 410, 420, 431, 481, 483, 485–488, 504–505, 508, 513, 526, 561

(56) References Cited

U.S. PATENT DOCUMENTS

| | | | |
|---|---|---|---|
| 4,928,693 A | | 5/1990 | Goodin et al. |
| 5,113,868 A | | 5/1992 | Wise et al. |
| 5,178,153 A | * | 1/1993 | Einzig |
| 5,715,827 A | | 2/1998 | Corl et al. |
| 5,775,338 A | | 7/1998 | Hastings |
| 5,807,265 A | | 9/1998 | Itoigawa et al. |
| 5,873,835 A | * | 2/1999 | Hastings et al. ............ 600/488 |
| 6,026,317 A | * | 2/2000 | Verani .................... 600/431 X |
| 6,094,591 A | * | 7/2000 | Foltz et al. ................. 600/419 |

OTHER PUBLICATIONS

U.S. application No. 09/264,782, Dgany et al.
U.S. application No. 09/666,841, Dgany et al.

* cited by examiner

*Primary Examiner*—Robert L. Nasser
(74) *Attorney, Agent, or Firm*—Nath & Associates PLLC; Harold L. Novick

(57) ABSTRACT

The present invention relates to intravascular pressure measurement based devices and methods determining clinical parameters related to stenosis severity for improved clinical diagnosis and treatment of cardiovascular disease in blood vessels or tubular conduits. More specifically, the invention provides methods for the determination of the clinically significant well known Coronary Flow Reserve (CFR) parameter-previously acquired by velocity measurement devices. In addition Coronary Flow Reserve in the same vessel without stenosis may be estimated and uses to select the necessary medical treatment. Additional pressure based clinical parameters, Diastole to Systole Velocity Ratio (DSVR) and Fractional Flow Reserve (FFR) in stenotic blood vessel during intervention (using only pressure measurements across stenosis) may also be calculated simultaneously, with the same set of interventional devices. Correlation of CFR with these parameters (e.g. FFR) may be further used to estimate the stenosis severity, downstream stenosis and the condition of the vascular bed or conditions related to aneurysms. It is known that there is a correlation between CFR and FFR for healthy vascular bed. Too low value of CRF for given FFR indicates either downstream flow restriction or insufficient infusion of vasodilator. Too high value of CFR for given FFR indicates vascular bed disease.

23 Claims, 45 Drawing Sheets

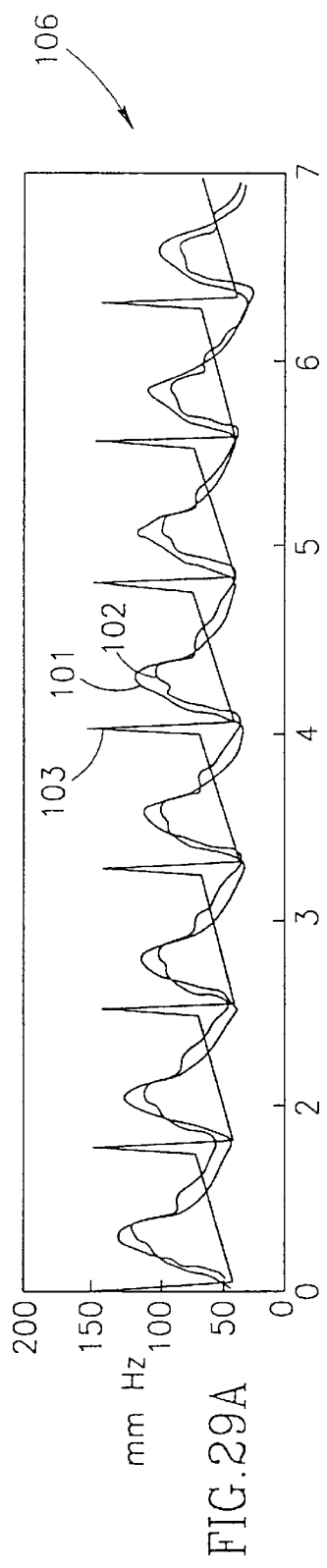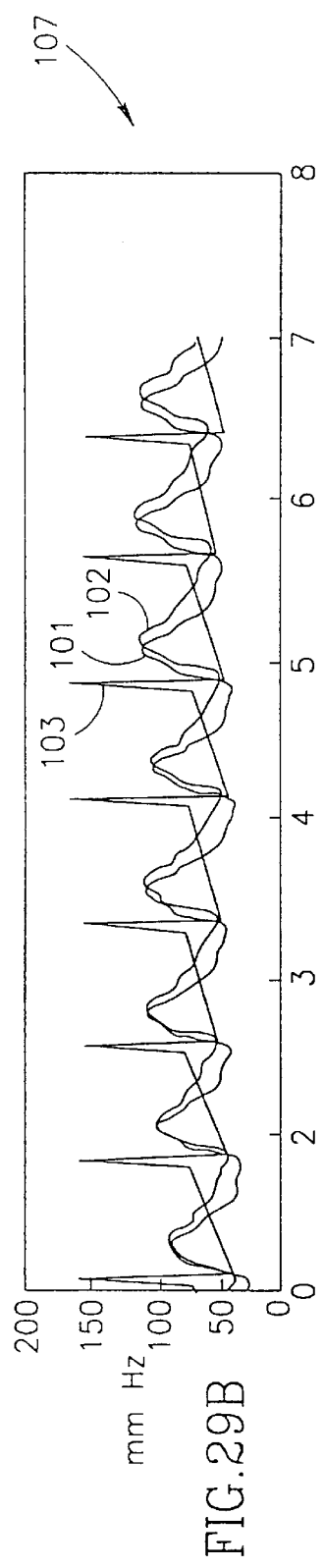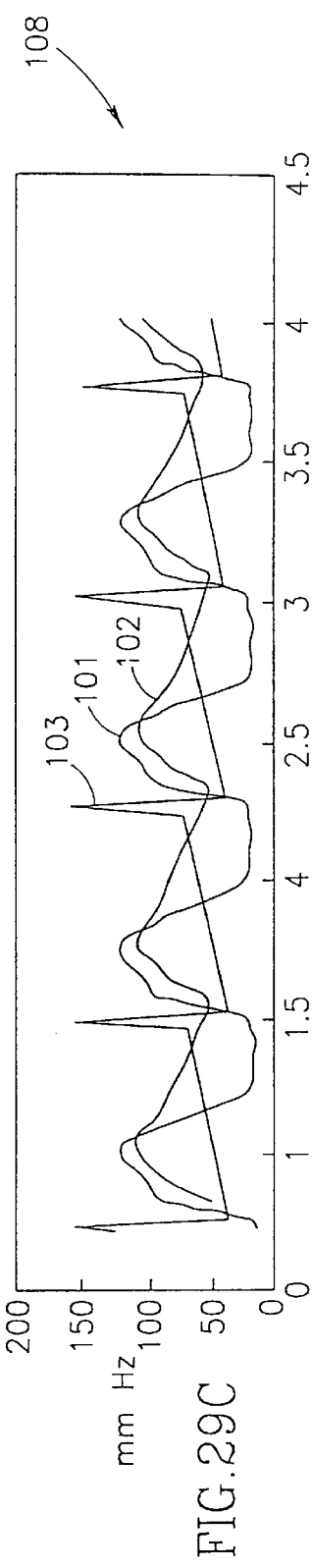

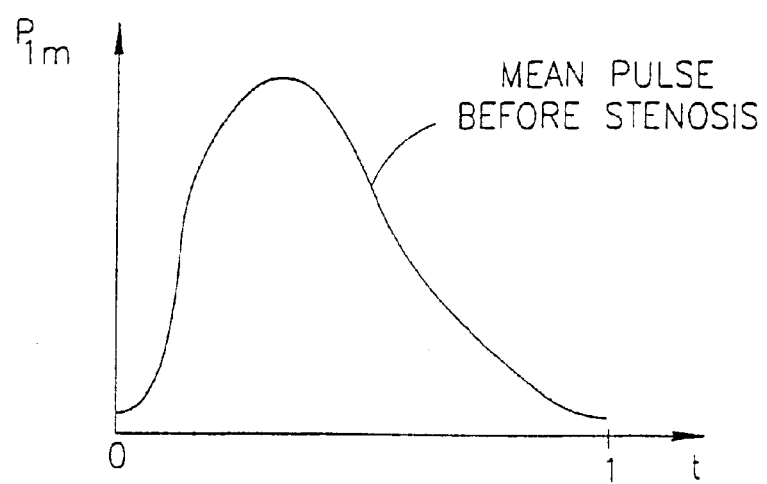
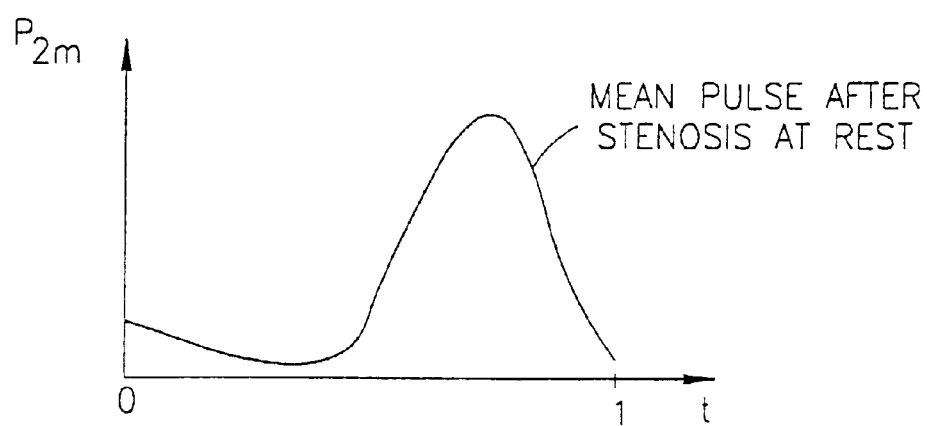
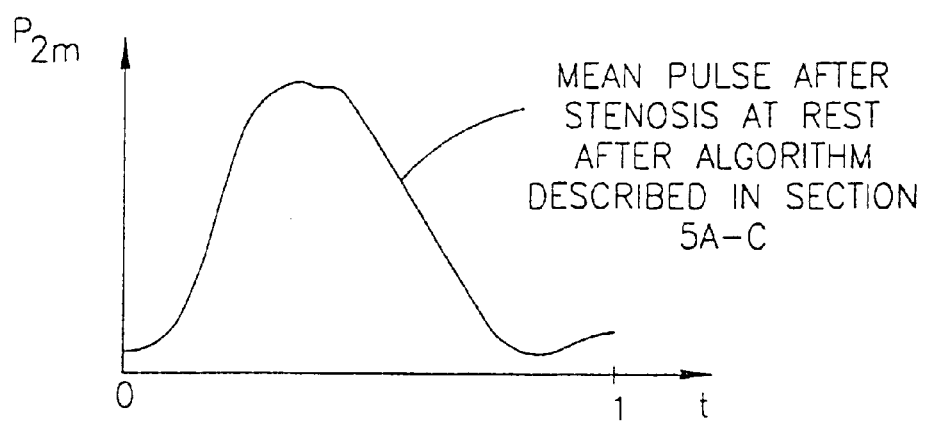
FIG.43B

METHOD AND SYSTEM FOR PRESSURE BASED MEASUREMENTS OF CFR AND ADDITIONAL CLINICAL HEMODYNAMIC PARAMETERS

CROSS-REFERENCES TO OTHER APPLICATIONS

This application claims the benefit of U.S. patent application Ser. No. 09/264,782, filed on Mar. 9, 1999.

FIELD OF INVENTION

The present invention relates to the field of medical diagnostic and therapeutic devices in general and to a system for intravascular characterization of blood vessel lesions and vascular bed.

BACKGROUND OF THE INVENTION

Vascular diseases are often manifested by reduced blood flow due to atherosclerotic occlusion of vessels. For example, occlusion of the coronary arteries supplying blood to the heart muscle is a major cause of heart disease. Numerous methods are currently available for treating various lesion types. Some of these methods are given herein below, sequenced from "softer" to "heavier", relating to their ability to open calcified lesions; per cutaneous trans-luminal angioplasty (PTCA), "Cutting balloon" angioplasty, directional coronary atherectomy (DCA), rotational coronary atherectomy (RCA), Ultrasonic breaking catheter angioplasty, transluminal extraction catheter (TEC) atherectomy, Rotablator atherectomy, and excimer laser angioplasty (ELCA). Often, stents are placed within the lesion so as to prevent re-closure of the vessel (also known as recoil).

Lesion characteristics, together with vessel condition proximal and distal to the lesion and vascular bed condition are used to determine the medically and economically optimal treatment method or combination of methods of choice. Geometry, pressure and flow are three variables often measured in the cardiovascular system. These measurements are performed prior, during and after the treatment, providing diagnostic and therapeutic data. The measurement prior to the treatment allows careful treatment selection. Measurements during and after the treatment enable evaluation of the treatment efficacy. Recent progress in probe miniaturization opened a whole new range of pressure and flow measurements that have been previously impossible to perform.

Lesion geometry is evaluated by angiography, qualitative coronary angiography (QCA), or by intravascular ultrasound (IVUS). These measurements allow calculation of the percent diameter stenosis (angiography or QCA) or percent area stenosis (IVUS). This information is used to estimate stenosis severity, but during the last years clinicians have realized that direct physical information about pressure and flow is necessary for complete evaluation of coronary artery disease. Physiological measurements such as pressure gradient have been clinically used as an indicator for lesion severity. However, previous attempts to relate the pressure gradient across the stenosis to its functional significance have been disappointing. The decrease in the pressure gradient after PTCA has been used to assess the success of the treatment, with poor correlation.

Other parameters have been defined and proven more effective as indicators for lesion severity. The coronary flow velocity reserve (CFVR) is defined as the ratio of hyperemic to baseline flow velocity. The fractional flow reserve (FFR) is defined as the ratio of distal (to stenosis) pressure (Pd) to aortic pressure (Pa) during hyperemia. Hyperemic conditions are obtained by administration of vasodilators (e.g. papaverine, adenosine). Clinical studies have demonstrated that in most cases, lesions with CFVR<2 must be treated using one of the above mentioned methods, whereas for patients with CFVR>2, angioplasty may be avoided. Similarly, in most cases angioplasty may be avoided if FFR>0.75. Coronary flow occurs essentially during diastole while systolic contribution to total coronary flow is smaller. A notable difference between diastolic to systolic velocity ratio (DSVR) was observed between normal and stenotic arteries. A cut-off value of 1.7 was proposed to distinguish between significant and non-significant lesions.

The FFR and CFVR are independent but complementary indicators. The first characterize the specific lesion whereas the second is a more global parameter, characterizing the lesioned vessel (lesion and distal bed). Clinical studies (Di Mario et al., Catherization and Cardiac Diagnosis 38, 189–201, 1996) show that for approximately 75% of the patients CFR and FFR lead to the same conclusion regarding the lesion significance. At the same time, for 25% of the patients, the conclusions regarding lesion significance were different. This means that simultaneous determination of coronary flow reserve and fractional flow reserve is highly important and gives the clinician the additional and more complete information regarding the lesion severity.

Major technical progress has been made lately with respect to pressure and velocity monitoring guide wires. For example, 0.014" Pressure Wire ™ (Radi Medical System, Uppsala, Sweden) is now available for intracoronary pressure measurements. However, for light stenosis, these measurements may be performed using diagnostic low profile catheters, Millar pressure transducer catheters (available by Millar Instruments, Inc., Houston, Tex., U.S.A.) or any other intravascular pressure equipment.

A 0.014" Doppler Flow wire (Cardiometrics Inc., Mountain View, Calif.) is now available for intracoronary velocity measurements. Both wires may be advanced into distal parts of the coronary tree without significantly impeding the flow. Simultaneous measurements of FFR and CFVR require the use of both wires. Such a procedure is complicated, expensive and was used only for research purposes. Therefore, clinicians use either velocity measurements to calculate coronary flow velocity reserve (CFVR) or pressure measurements to calculate fractional flow reserve (FFR). Furthermore, working with the Flow wire is sensitive to the location of the tip within the vessel cross section. The wire tip will measure accurately if located along the longitudinal axis. However, significant errors will appear once the wire is within the boundary layer. Therefore, manipulating the Flow wire requires high expertise and a lot of experience. Fortunately, these limitations are not relevant to the pressure wire measurements, yielding accurate data with simple handling.

SUMMARY OF THE INVENTION

This invention provides a method for calculating the flow-based clinical characteristics, coronary flow reserve (CFR) and diastolic to systolic velocity ratio (DSVR), in addition to the FFR, using pressure measurements across a stenosis. In addition coronary flow reserve in the same vessel without stenosis ($CFR_0$) may be estimated as well as aneurysms. FFR, CFR, $CFR_0$ and DSVR are simultaneously calculated for a complete characterization of the vessel of interest. Further, the present invention relates generally to a sensor apparatus for determination of characteristics in a tubular conduit, such as a blood vessel or the urethra, having at least one pressure sensor adapted to measure pressure across an obstruction.

The invention provided, includes a processor unit operatively connected to the at least one sensor, a program for controlling the processor unit. The processor unit is operative with the program to receive signals from the sensor; identify changes in the sensor signal; detect characteristics of the tubular conduit, the characteristics of the tubular conduit being divided from changes in the sensor signal; and recognized and assign a label to the characteristic of said tubular conduit. This invention provides a system which includes the Automatic Similar Transmission method.

The characteristics that may be determined include a flow ratio in a blood vessel; a coronary flow reserve in a blood vessel; diastole to systole velocity ratio in a blood vessel; coronary flow reserve together with fractional flow reserve in the same blood vessel without stenosis and analysis of their correlation for estimation of vascular bed conditions; coronary flow reserve together with fractional flow reserve in the same blood vessel with out stenosis for estimation of vasodilatation effectiveness.

Further, this invention provides the determination of a hemodynamic condition of the artery by determining the vascular bed index ($VBI_0$) which is equal to the ratio of mean shear to mean pressure. The invention provides a system and methods for determining the vascular bed index.

Further, the present invention provides a methods of determining/detecting microvascular disease due to the abnormal ratio of FFR to CFR based on either or proximal and/or distal pressure. The method may be in combination with a balloon procedure. Also, the methods described provide for post PTCA evaluation (prior to stenting), determination or validation of dilatation success by subsequent CFR increase after PTCA, and indication of whether a stent is neded. The methods and systems provided herein, indicate high probability or microvascular disease, due to the abnormal ratio of FFR to CFR. Further, Post Stenting in combination with a deflation balloon allows the estimation of CFR of the vessel. Thus, in one embodiment of the invention only a distal pressure measurement will allow the CFR calculation.

Lastly, this invention provides determining CFR and FFR directly from intraarterial pressure measurements, thus the simultaneous CFR and FFR measurements permit one to obtain additional information about the vascular bed. The present invention provides the hemodynamical parameters in estimating the severity of stenotic blood vessels in an attempt to increase the reliability of these parameters.

BRIEF DESCRIPTION OF THE DRAWINGS

The present invention will be understood and appreciated more fully from the following detailed description taken in conjunction with the appended drawings in which like components are designated by like reference numerals:

FIG. 1.a are schematics isometric view of a system for determining blood vessel hemodynamic parameters, constructed and operative in accordance with another preferred embodiment of the present invention;

FIG. 1.b are schematics isometric view of a system for determining blood vessel hemodynamic parameters, constructed and operative in accordance with another preferred embodiment of the present invention;

FIG. 2.a is a schematic functional block diagram illustrating the details of the system 1.a of FIG. 1.a;

FIG. 29 presents human data of ECG signals and pressure measurements during rest and vasodilatation. These data are used to calculate hemodynamic parameters using synchronization by ECG signals.

DETAILED DESCRIPTION OF THE INVENTION

Figure 1:
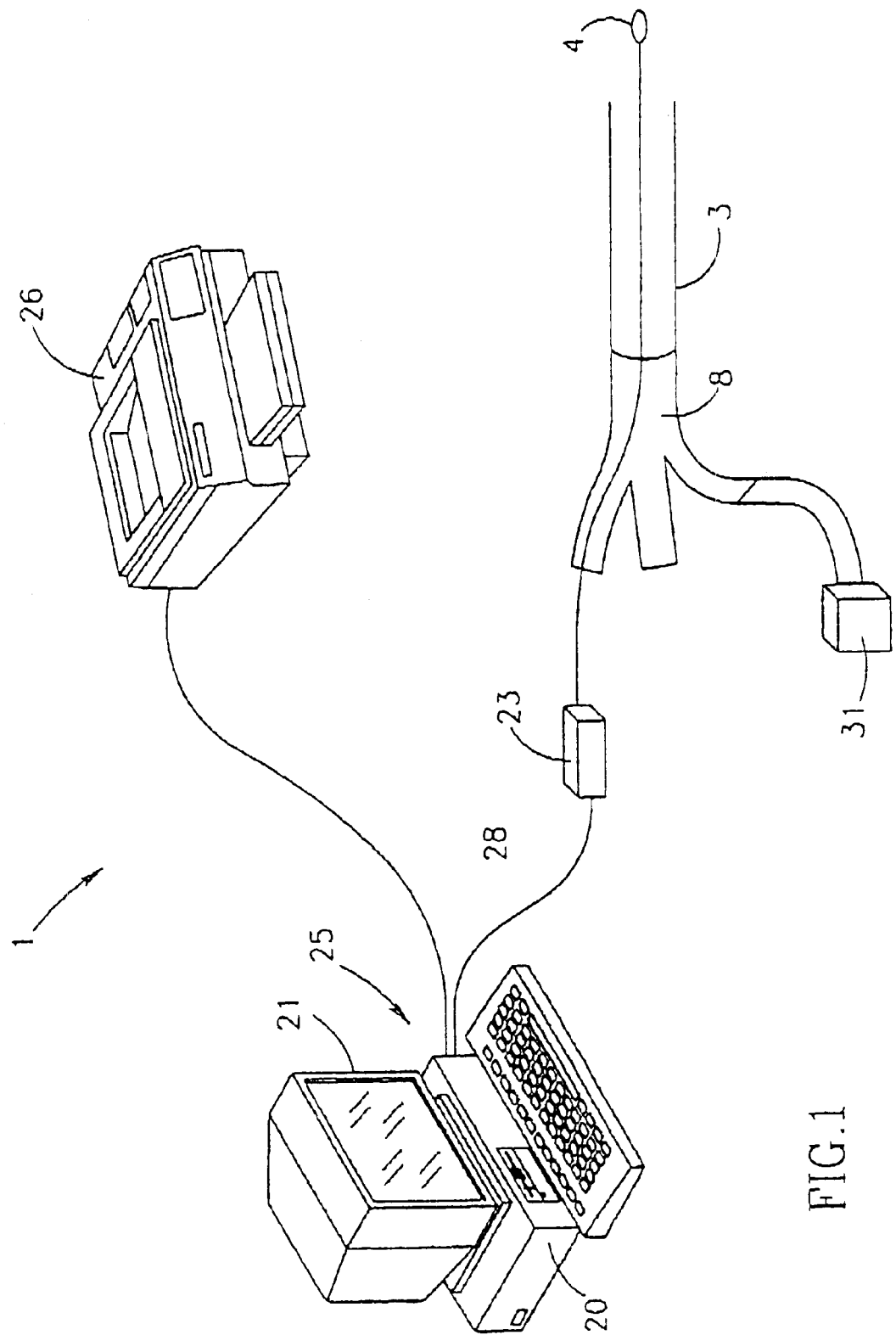
FIG. 1 is a schematic isometric view of a system for determining blood vessel hemodynamic parameters, constructed and operative in accordance with a preferred embodiment of the present invention.
Figure 1A:
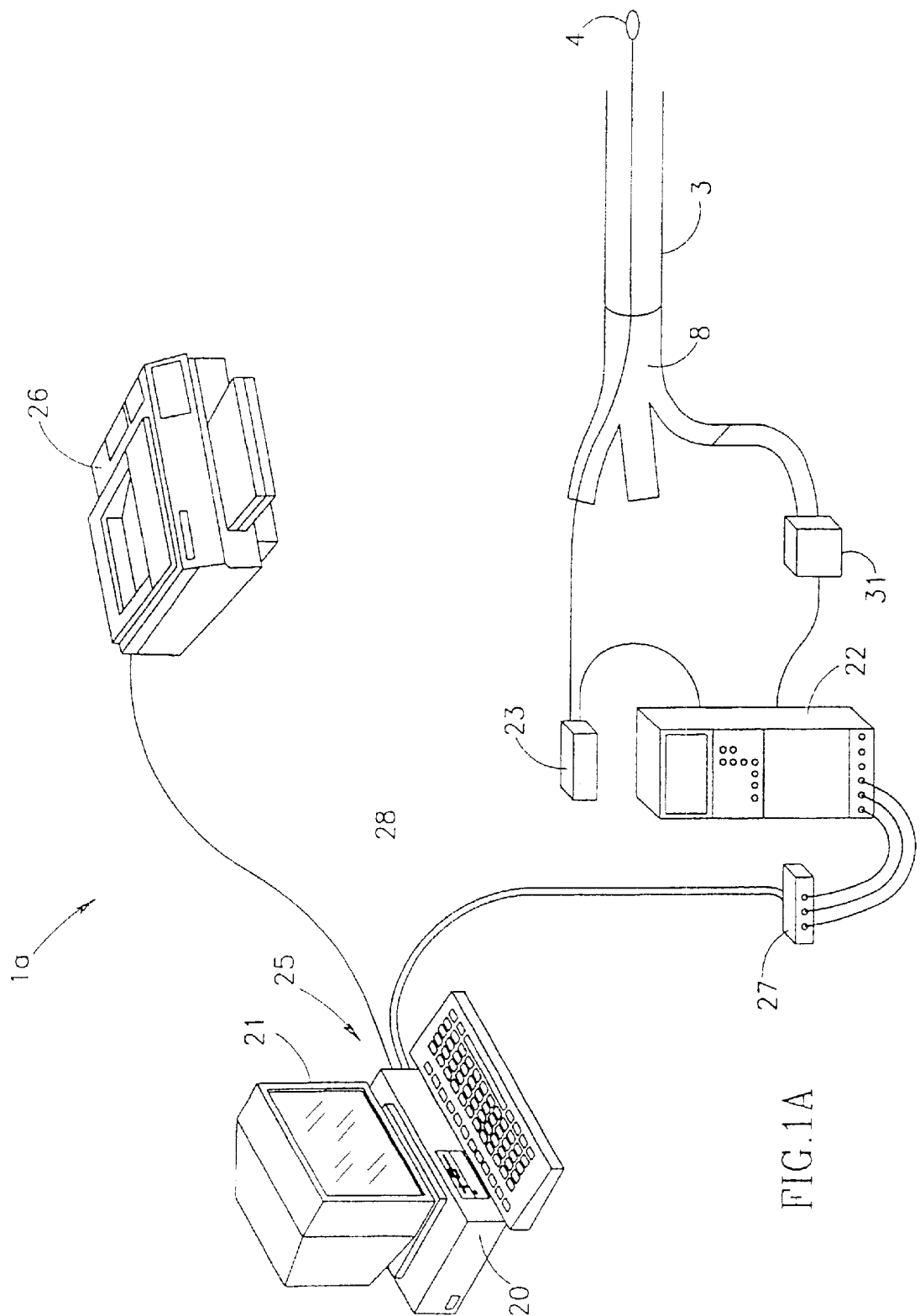
Figure 1B:
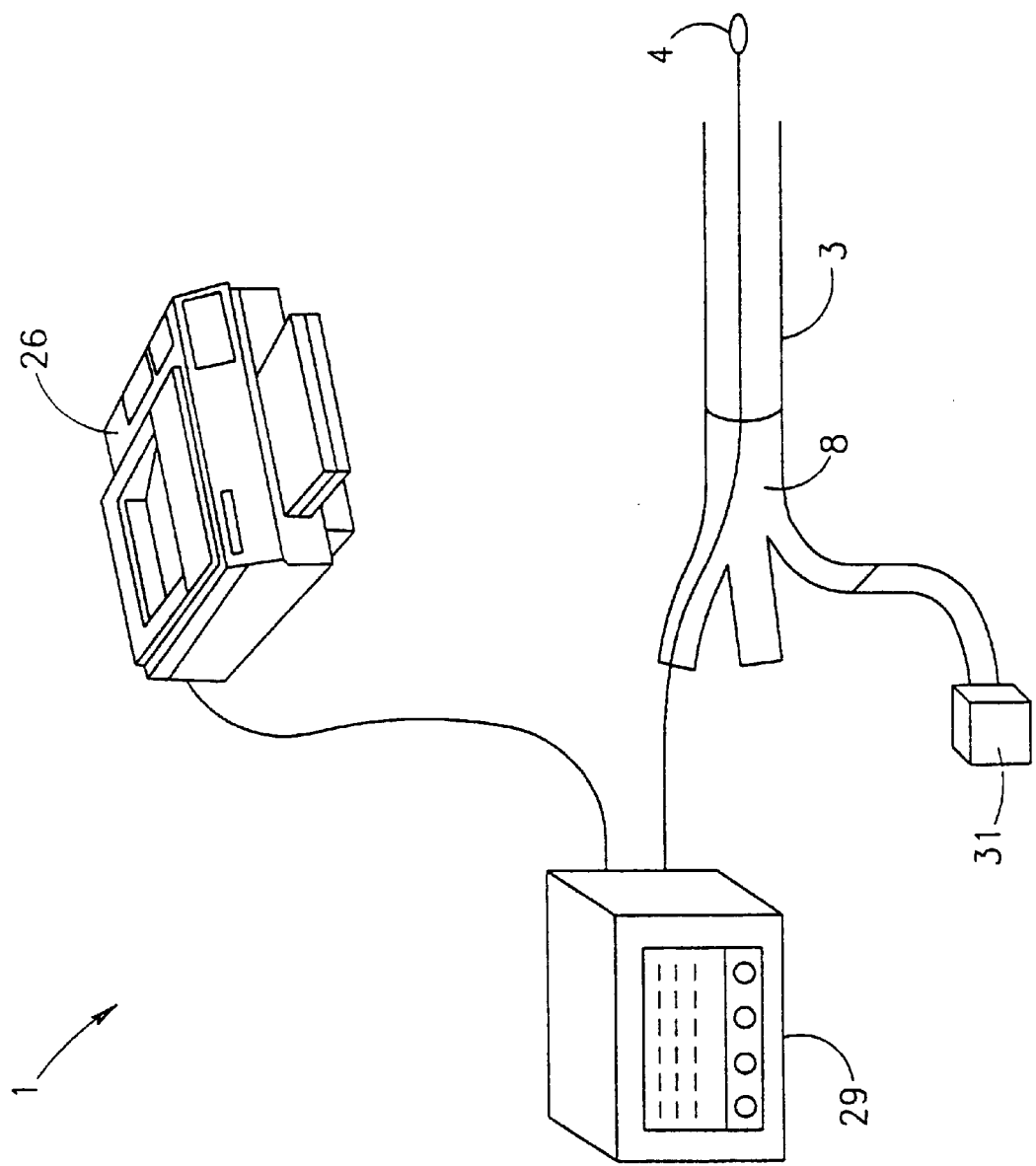

The pressure gradient in a blood vessel without stenosis is small (pressure difference between two points 5 cm apart is less than 1 mm Hg). The accuracy of the devices for pressure measurement, which are used in medicine for intracoronary pressure measurements does not allow accurate determination of such small pressure differences. Therefore, one cannot make an accurate calculation of flow using these existing pressure measurement devices in a healthy non-stenosed vessel. The situation is different if an obstruction exists in the blood vessel (stenosis or some artificial obstruction). The pressure difference across such an obstruction may reach 40–50 mmHg at rest and 60–70 mmHg during hyperemia. This significant pressure difference may be measured with high accuracy and may be used for calculations of coronary flow reserve (CFR), using the methods and system presented herein. This calculated CFR might be slightly different than the coronary flow velocity reserve (CFVR) as measured by the Flow wire. The difference may arise from changes in the velocity profiles. Limiting to the available technologies, accurate results may be achieved if the pressure difference across the stenosis at rest is more than 4 mmHg. However, using advanced methods of analysis, will allow to reduce this limitation to about 0.5 mmHg.

As provided herein, the methods and systems described allow the calculation of both coronary flow indices, CFR and FFR directly from intrarterial pressure measurements. The pressure derived flow indices correlated with and accurately predicted actual flow measurements. By applying the methods percutaneous coronary interventions (PCI) decisions may be accurately made so as to achieve reduction in flow limiting ischemia. The results presented herein based on both a Computational Fluid Dynamic (CFD) simulation and confirmance by in-vivo experiments demonstrated that the methods and systems provided herein, at all levels of stenosis severity pressure measurements derived indices of CFR and FFR had superior correlation with actual flow indices.

Further, the present invention provides methods and a system for calculation of CFR and FFR from on line intra-arterial pressure measurements. Intracoronary pressure measurements were made in patients undergoing diagnostic angiography with findings of lesions of questionable clinical significance (intermediate lesions of 50–70% visual stenoses severity). Basal pressure measurements proximal, distal and during trans-lesional pull back were made with the methods and systems provided herein. Patients were given intracoronary adenosine to achieve maximal vasodilatation and measurements were taken.

In the work of Wong M., Vijayaraghavan G., Bae J. H., Shah P. M. "In Vitro Study of Pressure-Velocity Relation Across Stenotic Orifices", published in the American Journal of cardiology, v.56, pp.465–469, pressure—flow relation across stenotic orifices was investigated in pulsatile in-vitro model. They had shown that for short stenosis the pressure—flow relation is independent of the orifice size, for a wide pressure range. The relation is quadratic and crosses zero. This means, that in short stenosis, the pressure gradient across the stenosis ($\Delta p$ is a quadratic function of flow (Q).

$$\Delta p = K \cdot Q^2 \qquad (1)$$

Where K is a constant determined solely by the stenosis diameter. If pressure measurements are obtained simultaneously upstream of the stenosis and downstream of the stenosis rest and during hyperemia, then flow at rest across the stenosis may be calculated using the equation:

$$Q_{rest} = sqrt(\Delta p_{rest}/K) \qquad (2)$$

And the hyperemic flow may be found using the equation:

$$Q_{hyper} = sqrt(\Delta p_{hyper}/K) \qquad (3)$$

Where $\Delta p_{rest}$, $Q_{rest}$ and $\Delta p_{hyper}$, $Q_{hyper}$ are the pressure differences across the stenosis and flow during rest and hyperemia respectively. The coronary flow reserve (CFR) is defined as the ratio of the mean hyperemic flow to the mean flow at rest:

$$CFR = \frac{\int_{heartbeat} Q_{hyper} dt}{\int_{heartbeat} Q_{rest} dt}$$

Assuming the stenosis geometry is similar during rest and hyperemia, then K in equations (2) and (3) cancels out.

$$CFR = \frac{\int_{heartbeat} \sqrt{\Delta p_{hyper}}}{\int_{heartbeat} \sqrt{\Delta p_{rest}}}$$

Therefore, the coronary flow reserve (CFR) may be calculated if the pressure difference across the stenosis is known during rest and hyperemia. Equations (2) and (3) are valid only for short stenosis. In the case of an arbitrary stenosis, the pressure difference across the stenosis may be expressed as (Young D. F., Tsai F. Y. "Flow characteristics in model of arterial stenosis"—II. Unsteady flow J. Biomechanics, 1973, vol. 6, pp.547–559):

$$\Delta p = K_1 Q + K_2 Q^2 + K_3 dQ/dt$$

In the physiological range, the first and last components of this equation are small. With accuracy of 1 mmHg, equations (2) and (3) may be used. If Δp across the stenosis is more than 4 mmHg, the accuracy of CFR calculation will reach 10%.

$CFR_0$ is the coronary flow reserve of a healthy vascular bed without stenosis. Using the following notations:

Q mean flow over a heartbeat in a stenotic vessel at rest;
$Q^V$ mean flow over a heartbeat in a stenotic vessel during hyperemia (vasodilatation);
$Q_N$ mean flow over a heartbeat in the same non-stenotic vessel at rest;
$Q_N V$—means flow over a heartbeat in the same non-stenotic vessel during hyperemia (vasodilatation);
Pa: Aortic pressure
Pd: Mean distal pressure at rest
Then, $$CFR = \frac{Q^V}{Q}; \quad CFR_0 = \frac{Q_N^V}{Q_N}; \quad FFR = \frac{Q^V}{Q_N^V} = \frac{P_d^V}{P_a}$$

and, $$CFR_0 = \frac{Q_N^V}{Q^V} \cdot \frac{Q^V}{Q} \cdot \frac{Q}{Q_N} = \frac{1}{FFR} \cdot CFR \cdot \frac{Q}{Q_N}$$

The vascular bed autoregulation tends to compensate hydraulic resistance of the stenosis, so at rest $Q=Q_N$, hence $$CFR_0 = CFR/FFR$$

If CFR and FFR are known, then the coronary flow reserve (CFR0) in the same vessel, in case of healthy vascular bed, may be derived. A too high or too low value of $CFR_0$ indicates a non healthy vascular bed. Too low value of CFR for given FFR indicates either downstream flow restriction (additional stenosis) or insufficient infusion of vasodilator. Too high value of CFR for given FFR indicates vascular bed disease. The last equation may be used for determination of coronary flow reserve by positioning an artificial obstruction in a blood vessel, as presented herein below.

Figure 43A:
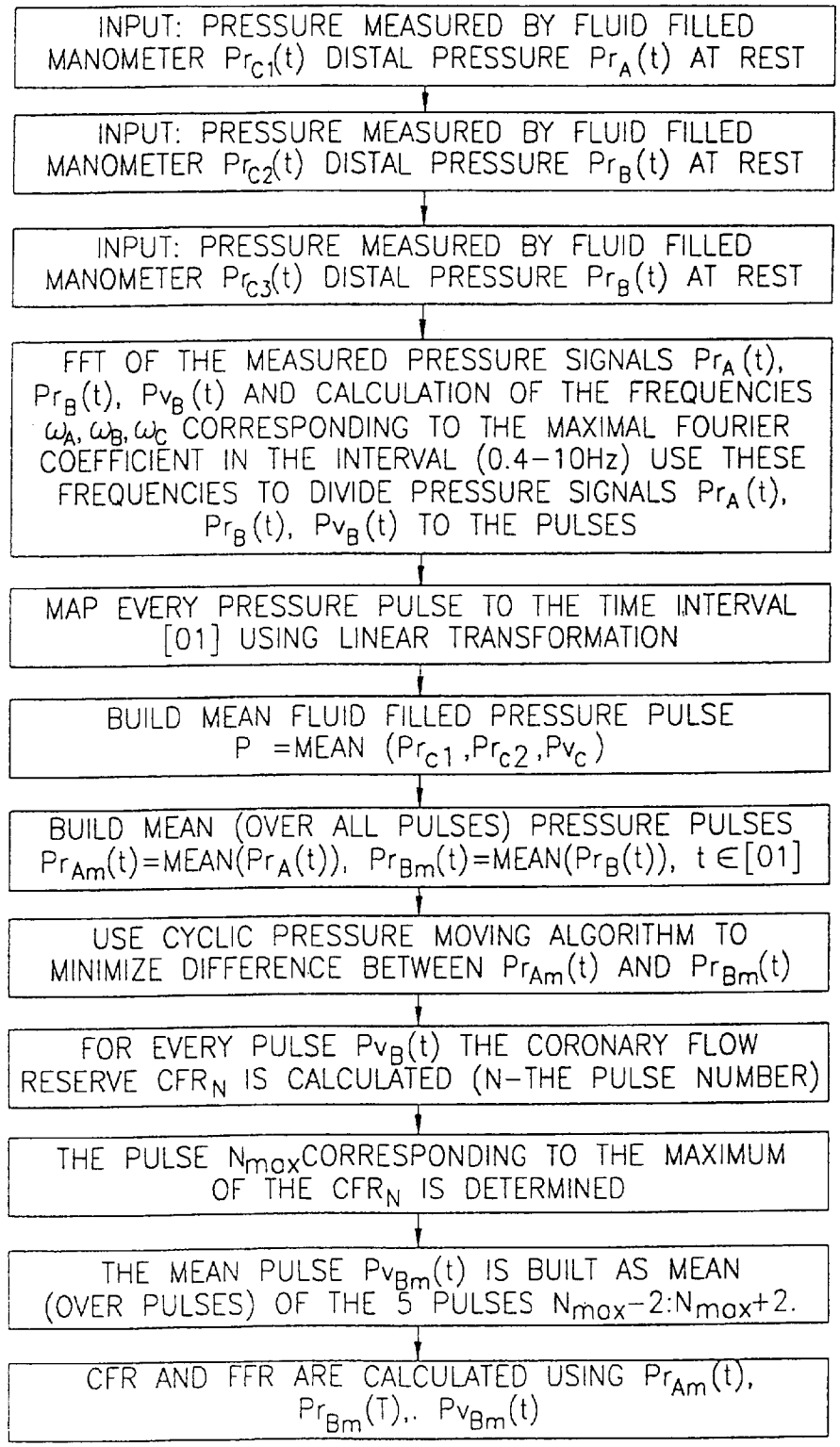
FIG. 43 Block diagram of Automatic Similar Transformation Method

In another embodiment, calculating CFR and FFR may be accomplished by dividing into pulses the proximal and distal pressure. Dividing the pulses are known to those skilled in the art. For example, one use an ECG signal or only using a pressure signal. The Automatic Similar Transformation (AST) Method the steps of which are described in FIG. 43. In one embodiment, the systems provided herein include the AST method.

In the AST method, every pulse p(t), 0<t1<t2 is mapped to the time interval [01] using the following transformation P(τ)=P((τ−t1)/(t−t2))), 0<τ<1. Then mean pressure pulse $P_{means}(\tau)$ is calculated, using averaging over all pulses for a give τ. Six pressure signals result: mean proximal fluid filled pressure Fp(τ); mean proximal pressure, measured by pressure transducer Pp(τ); mean fluid filled pressure Fd(τ) and means pressure transducer pressure Pd(τ) both measured at rest when pressure transducer is distal to stenosis; mean fluid filled pressure Fv(τ) and mean pressure transducer pressure Pv(τ) both measured during vasodilation when pressure transducer is distal to stenosis. Pressure signals Pd(τ) and Pv(τ) are corrected to the changes in aortic pressure:

$$Pd(\tau)=Pd(\tau)*mean(Fp(\tau))/mean(Fd(\tau)));$$

$$Pv(\tau)=Pv(\tau)*mean(Fp(\tau))/mean(Fv(\tau)));$$

Now pressure Pp(τ), Pd(τ) and Pv(τ) are used to calculate CFR, FFR, and DSVR. In the pulse detection using only pressure signal the pulse detection is based on the pressure signal measured by moving pressure transducer. The pulse detection method consists from following stages:

1. FFT (fast Fourier transform) of the measured pressure signal in proximal point at rest ($P_1$(t)), in distal point at rest ($P_2$(t)) and in distal point during vasodilatation ($P_3$(t)).
2. The frequency corresponding to the maximum value of the Fourier coefficients in the interval (0.5–10 Hz) is used as the pulse frequency $\omega_1$ (for $P_1$ series), $\omega_2$ (for $P_2$ series), $\omega_3$ (for $P_3$ series).
3. For every pressure series $P_i$ pressure the times of every pulse maximums $t_{im}$ are found using following steps:
   a. First maximum must be found in the interval $0<t<\omega_i*f$, were f is the sampling rate.
   b. The pressure maximum number k is looking for in the interval ($t_{m,k-1}+0.5*\omega_i*f$, $t_{m,k-1}+1.5*\omega_i*f$).
4. Finding time $T_{m,k}$ when pressure reach minimum in the time interval ($t_{m,k-1}$, $t_{m,k}$) Points $T_{m,k}$ are points of the beginning of the pulse number k (hence end of the pulse k−1).

The measured pressure signal is now divided into pulses. For pulse selection, the following steps are taken:

1. For every pulse calculate 'length' lp of the fluid filled ($P_f$) and pressure ($P_r$) signal using equation $I_p$=mean($P^2$)−means(P*)mean(P), where mean is calculated over one heartbeat. P means $P_f$ or $P_r$.
2. Only pulses with $lp_f/lp$>thesh are considered (here $lp_f$ and lp are the length of fluid filled and pressure pulses respectively, tresh is a number (in software realization thresh=0.1)). This allows throwing away pulses with drug admission.
3. Every pulse is mapped to time interval (0,1) with sampling rate 200 Hz as in the previous version of the algorithm.
4. Mean pulses $P_{1m}$ and $P_{2m}$ at rest are calculated from pressure series $P_1$(t) and $P_2$(t) as in the previous algorithm, (for example $P_{1m}$(k)=mean($P_1$(k)), 1<k<200 time point number for interpolated pulse. Mean value is calculated over all pulses remaining after stage 2).
5. Due to difference of the pulse shape before and after stenosis the position of the pulse minimum may be different relative to the systole beginning. To compensate, the following cycle pressure steps are taken:

6.
a. Double pulse $P_{2m}$. $P_{2m,double}(1:400)=[P_{2m}(1:200), P_{2m}(1:200)]$.
b. Calculate $$s(k) = \sum_{k}^{k+200} (P_{2m,double}(k+i) - P_m(i))^2$$

c. Find $k_{min}$, the value of k when s(k) reach minimum. Instead $P_{2m}$ use $P_{2m}=P_{2m,double}(k_{min}:k_{min}+200)$.

7. The steps of step 5 applied to every n-th pulse $P_{3n}$ (1:200) remaining after stage 2. Then $CFR_n$ for this pulse is calculated using equation:

$$CFR_n = \left(\sum_{i=1}^{200} \sqrt{P_{3n}(i) - P_{1m}(i)} \bigg/ \sum_{i=1}^{200} \sqrt{P_{2m}(i) - P_{1m}(i)}\right)$$

8. The pulse $n_{max}$ when $CFR_n$ reach maximum must be found. Mean pulse during vasodilatation $P_{3m}$ is calculated as mean for 5 pulses $n_{max}-2:n_{max}+2$. Then CFR and FFR are calculated.

In another embodiment CFR may be calculated based on the difference across the stenosis may be estimated from the volume flow rate Q(t), the minimal stenosis cross-sectional area $A_S$ and the healthy vessel cross-sectional area $A_0$ using the Young-Tsai (Young D. F., Tsai F. Y. A flow characteristics in model of arterial stenosis A B II. Unsteady flow. J. Biomechanics, 1973, vol. 6 pp.547–559) equation upon one-heart beat ($u=Q/A_0$).

$$\Delta P = K_1 * u^2 + K_2 * u, \quad (1)$$

$$K_1 = 1.52 * \rho * CQ * (A_0/A_S - 1)^2$$

$$K_2 = 4 * \mu * K_\mu / (\pi * D_0^3)$$

$$K_\mu = 32 ** A_0 * (0.83 * L_S + 1.64 * D_S)/(D_0 A_S)$$

u: mean velocity
CQ=1.1
A0: cross-sectional area of a vessel
D0: cross-sectional diameter of a vessel
$\rho$: blood density
$\mu$: blood viscosity
LS: stenosis length If mean($u^2$)=b•mean(u)$^2$, then (HPG-hyperemic pressure gradient, BPG—baseline pressure gradient): BPG=K1*b*$(Q/A_0)^2$; HPG=K1*b*$(Q_v/A_0)^2$; Q, $Q_v$—flow at rest and during vasodilatation respectively, then HPG/BPG=$(Q_v/Q)^2$. CFR=$Q_v/Q$, hence CFR=sqrt(HPG/BPG).

In another embodiment flow was calculated using only pressure measurements across a stenosis. The flow (ml/min) in rest and after vasodilatation is determined based on measured FFR. The following relation between FFR and % stenosis was determined:

$$\%_{stenosis} = 0.8861 + 0.0641 * FFR - 0.6739 * FFR^2 \quad (3)$$

Figure 40A:
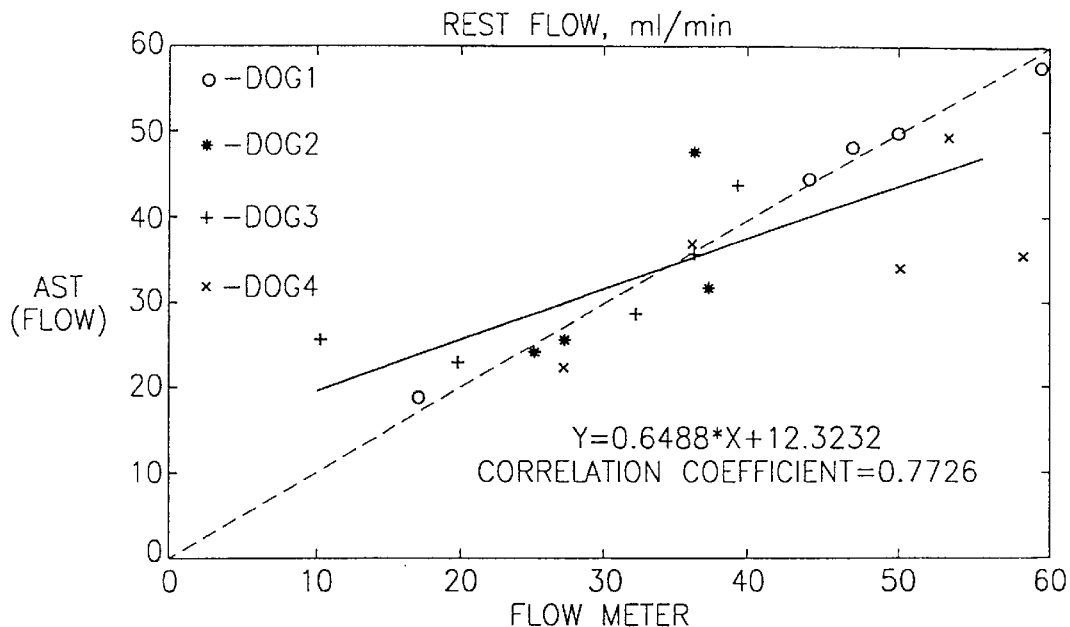
FIG. 40 Results of flow calculation using only pressure measurements across stenosis.
Figure 40B:
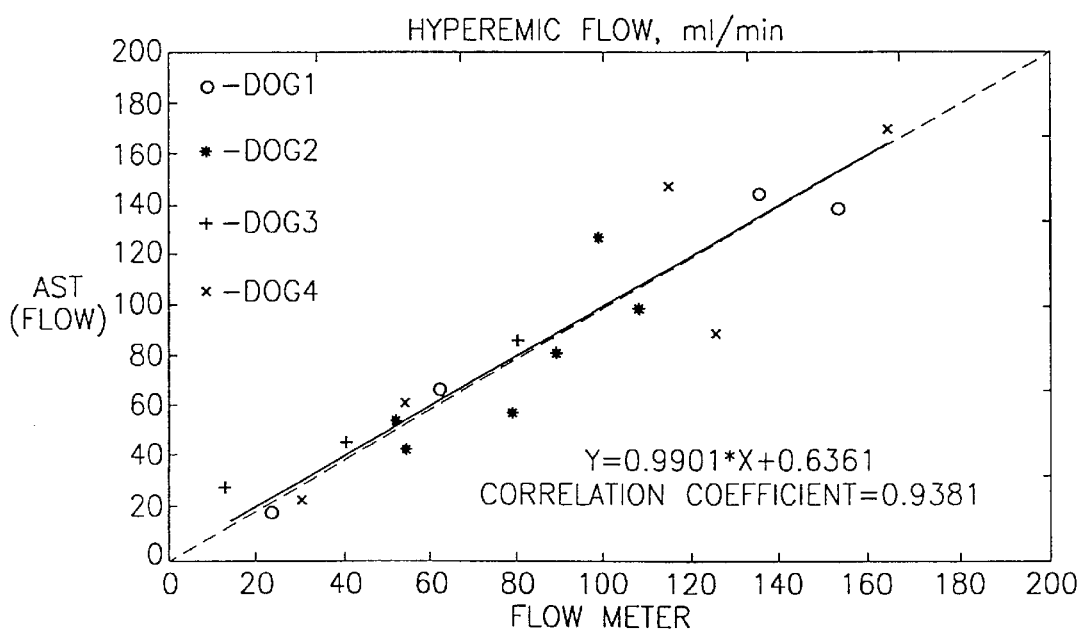
Figure 41A:
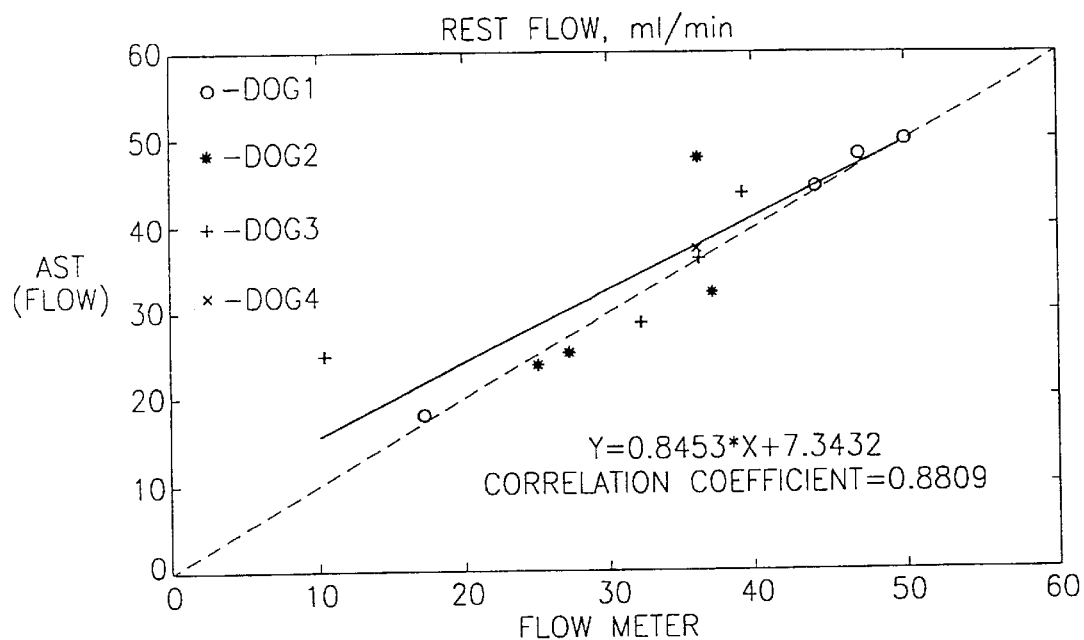
FIG. 41 Results of flow calculation using only pressure measurements across stenosis.
Figure 41B:
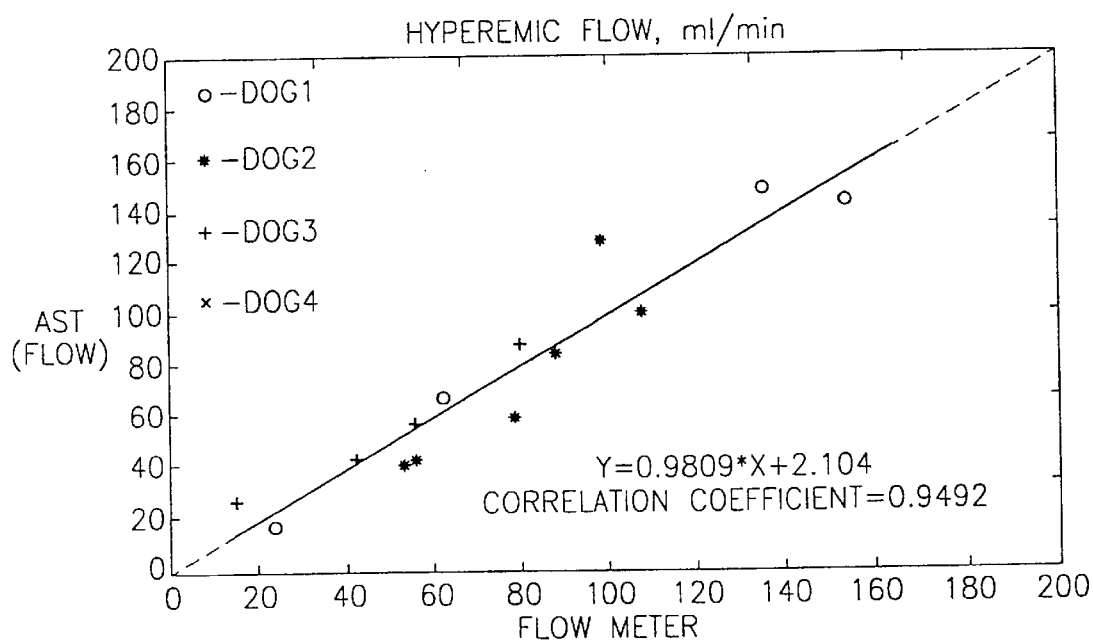

If the % stenosis is known, then the mean velocity u may be calculated by Young&Tsai equation (without linear term). The flow Q may be calculated if the diameter d of the vessel is known ($Q = u * \pi d^2 .4$). FFR can be used to estimate % stenosis. As shown in FIG. 40 hyperemic flow and flow at rest for all 4 dogs are presented. The hyperemic results are acceptable for all dogs (correlation coefficient R=0.94). The correlation coefficient at rest is relatively low (R=0.77) mainly due to the fourth dog. Correlation between measured and calculated flow for first 3 dogs is better, as may be seen from FIG. 41.a and 41-b. (R=0.88 at rest and R=0.95 during vasodilatation).

Figure 2:
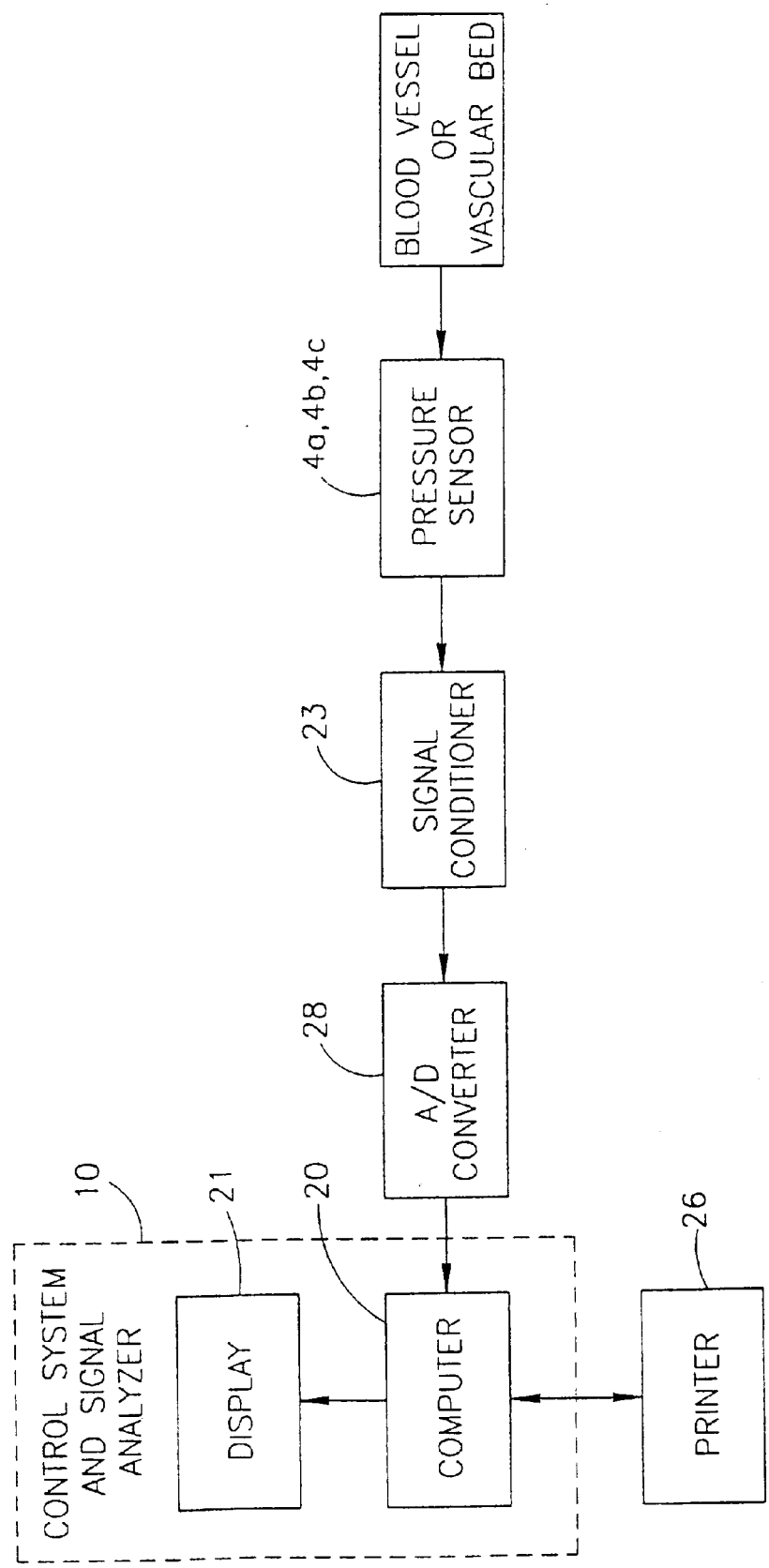
FIG. 2 is a schematic functional block diagram illustrating the details of the system 1 of FIG. 1.
Figure 2A:
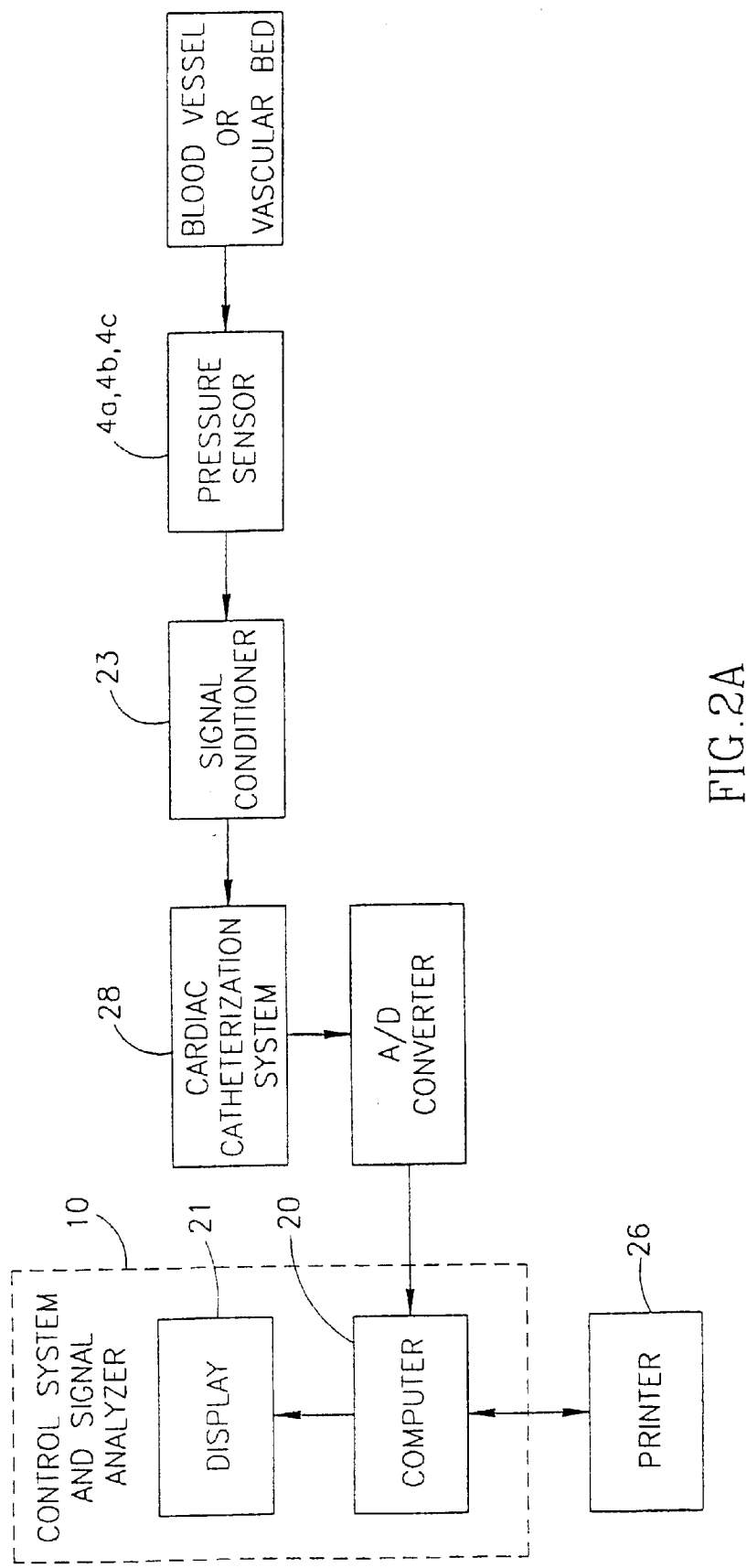

Reference is now made to FIGS. 1, 1.a, 1.b, 2 and 2.a. FIGS. 1, 1.a and 1.b present a schematic isometric view of a system for determining blood vessel (lesion regions and non-lesioned regions) clinical hemodynamic characteristics: CFR, DSVR and FFR. The system is constructed and operative in accordance with two embodiment of the present invention (1 and 1a). FIGS. 2 and 2.a are schematic functional block diagrams illustrating the details of the system 1 of FIG. 1 and system 1.a of FIG. 1.a.

Figure 3:
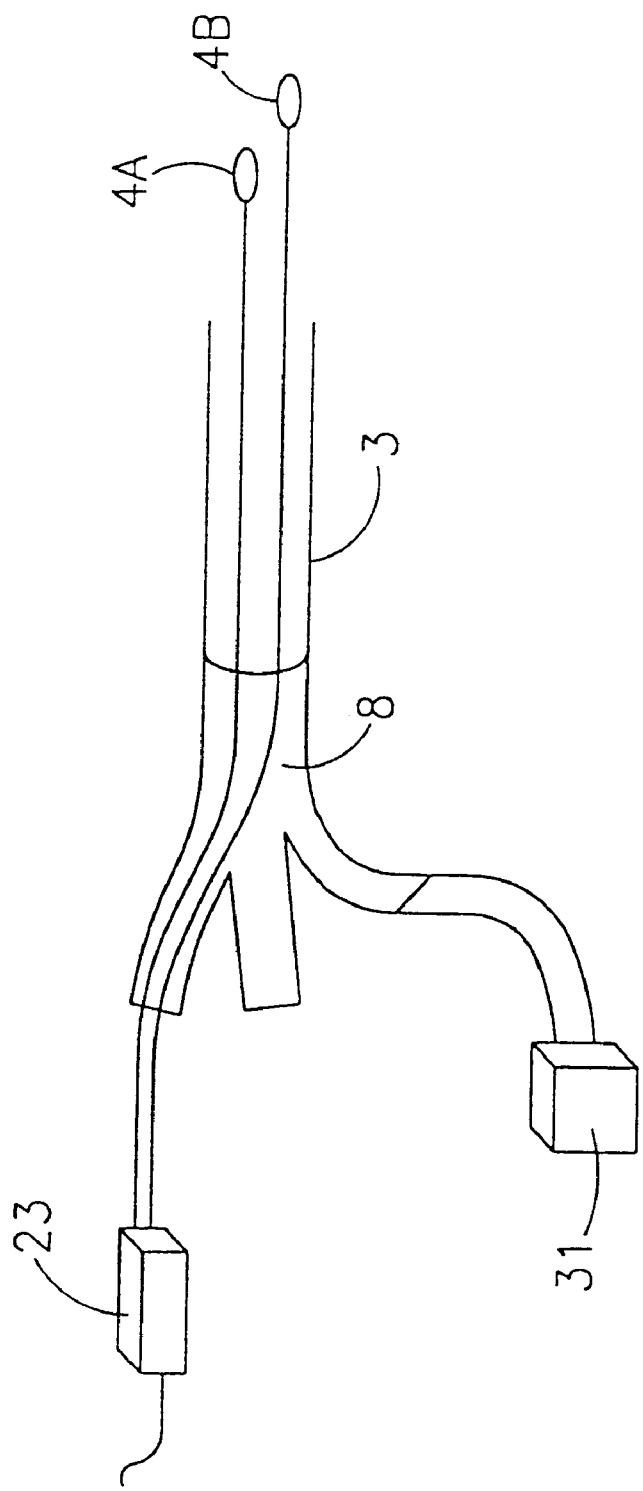
FIG. 3 is a schematic isometric view of a part of system 1 or 1.a of FIG. 1 or 1.a, constructed and operative in accordance with another preferred embodiment of the present invention.

The systems 1, 1.a, and 1.b. include a pressure sensor catheter or guide wire 4, inserted into the vessel directly or via a catheter lumen 3 for measuring the pressure inside a blood vessel. The lumen catheter may be a guiding catheter (e.g. 8F Archer coronary guiding catheter from Medtronic Interventional Vascular, Minneapolis, U.S.A.) or a diagnostic catheter (e.g. Siteseer diagnostic catheter, from Bard Cardiology, U.S.A.), a balloon catheter (e.g. Supreme fast exchange PTCA catheter, by Biotronik GMBH & Co, U.S.A.) or any other hollow catheter. System 1 and systems 1.a and 1.b. may include one (4) or more (i.e. FIG. 3) pressure sensors on guide wire and also a fluid filled (FF) pressure transducer 31 (standard catheterization lap equipment), connected via the end of the guiding catheter 3, for measuring the pressure inside a blood vessel. In an exemplary embodiment, the pressure sensor 4 can be the 3F one pressure sensor model SPC-330A or dual pressure catheter SPC-721, commercially available from Millar Instruments, Inc., TX, U.S.A., or any other pressure catheter suitable for diagnostic or combined diagnostic/treatment purposes such as the 0.014" guidewire mounted pressure sensor product number 12000 from Radi Medical Systems, Upsala, Sweden, or Cardiometrics WaveWire pressure guidewire from Cardiometrics Inc. an Endsonics company of CA, U.S.A.

The systems 1, 1.a and 1.b also include a signal conditioner 23, such as a model TCB-500 control unit commercially available from Millar Instruments, or Radi Pressure Wire Interface Type PWI10, Radi Medical Systems, Upsala, or other suitable signal conditioner. The signal conditioner 23 is suitably connected to the pressure sensor 4 for amplifying the signals of the pressure sensor. The system 1 further includes an analog to digital (A/D) converter 28 (i.e. NI E Series Multifunctional I/O model PCI-MIO-16XE-10 commercially available by National Instruments, Austin, Tex.) connected to the signal conditioner 23 and to the FF pressure transducer 31 for receiving the analog signals therefrom. The signal conditioner 23 may be integrated in the data acquisition card of the computer 20, or may also be omitted altogether, depending on the specific type of pressure sensors used.

The system 1.a of FIG. 1.a also includes a standard cardiac catheterization system 22, such as Nihon Kohden Model RMC-1100, commercially available from Nihon Kohden Corporation, Tokyo, Japan. The signal conditioner 23 and the FF pressure transduce 31 are directly connected to the monitoring system 22. The ECG is also available from the monitor using standard equipment and procedures. The system 1.a further includes an analog to digital (A/D) converter 28 connected to the output of the monitoring system 22 through a shielded I/O connector box 27, such as NI SCB-68 or BNC-2090 commercially available from National Instruments, Austin, Tex.

The systems 1 and 1.*a* also include a signal analyzer 25 connected to the A/D converter 28 for receiving the digitized conditioned pressure signals from the A/D converter 28. The signal analyzer 25, includes a computer 20 and optionally a display 21 connected to the computer 20 for displaying text numbers and graphs representing the results of the calculations performed by the computer 20 and a printer 26 suitably connected to the computer 20 for providing hard copy of the results for documentation and archiving. The A/D converter 28 can be a separate unit or can be integrated in a data acquisition card installed in the computer 20 (not shown). The computer 20 processes the pressure data, sensed by the pressure sensors 4 and acquired by the A/D converter 28 or the data acquisition card (not shown) and generates textural, numerical and/or graphic data that is displayed on the display 21. The system 1.*b* includes a single hardware box 29 containing all signal conditioning, calculations, archiving options and digital display and output to a printer 26.

Figure 4:
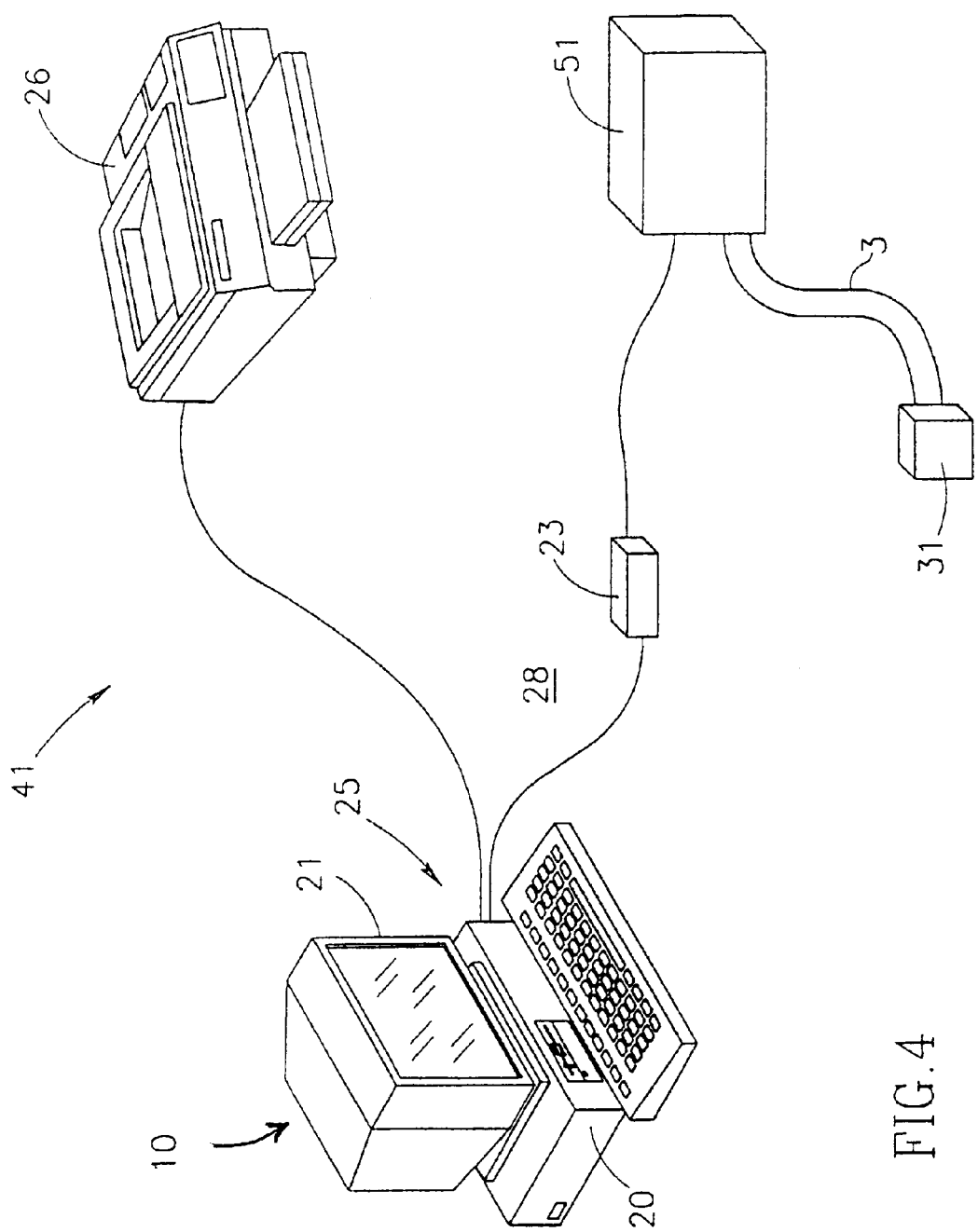
FIG. 4 is a schematic isometric view of an in-vitro system, constructed and operative in accordance with a preferred embodiment of the present invention.
Figure 5:
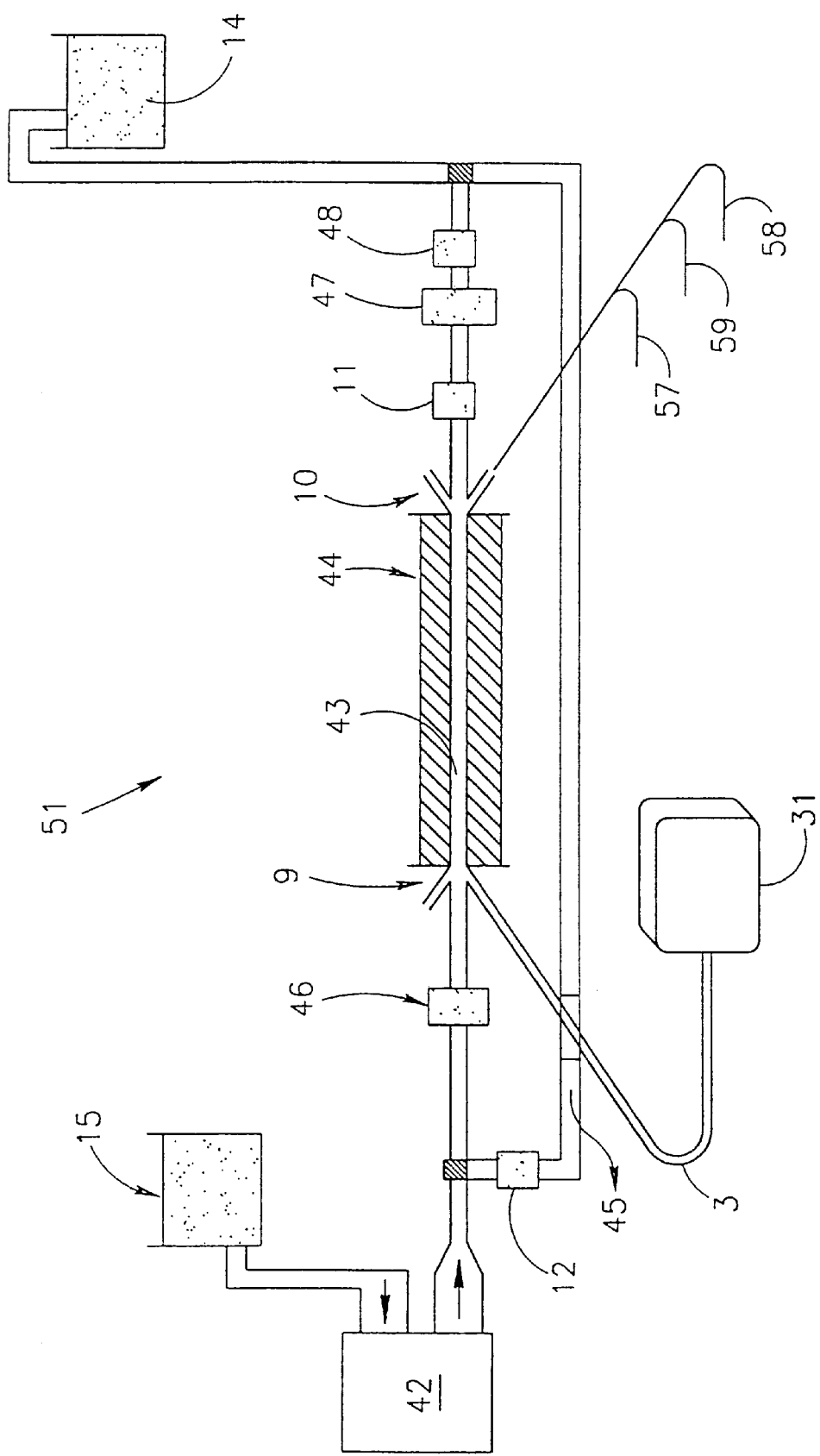
FIG. 5 is a schematic detailed illustration of the in-vitro tubing system 51 of FIG. 4.
Figure 6:
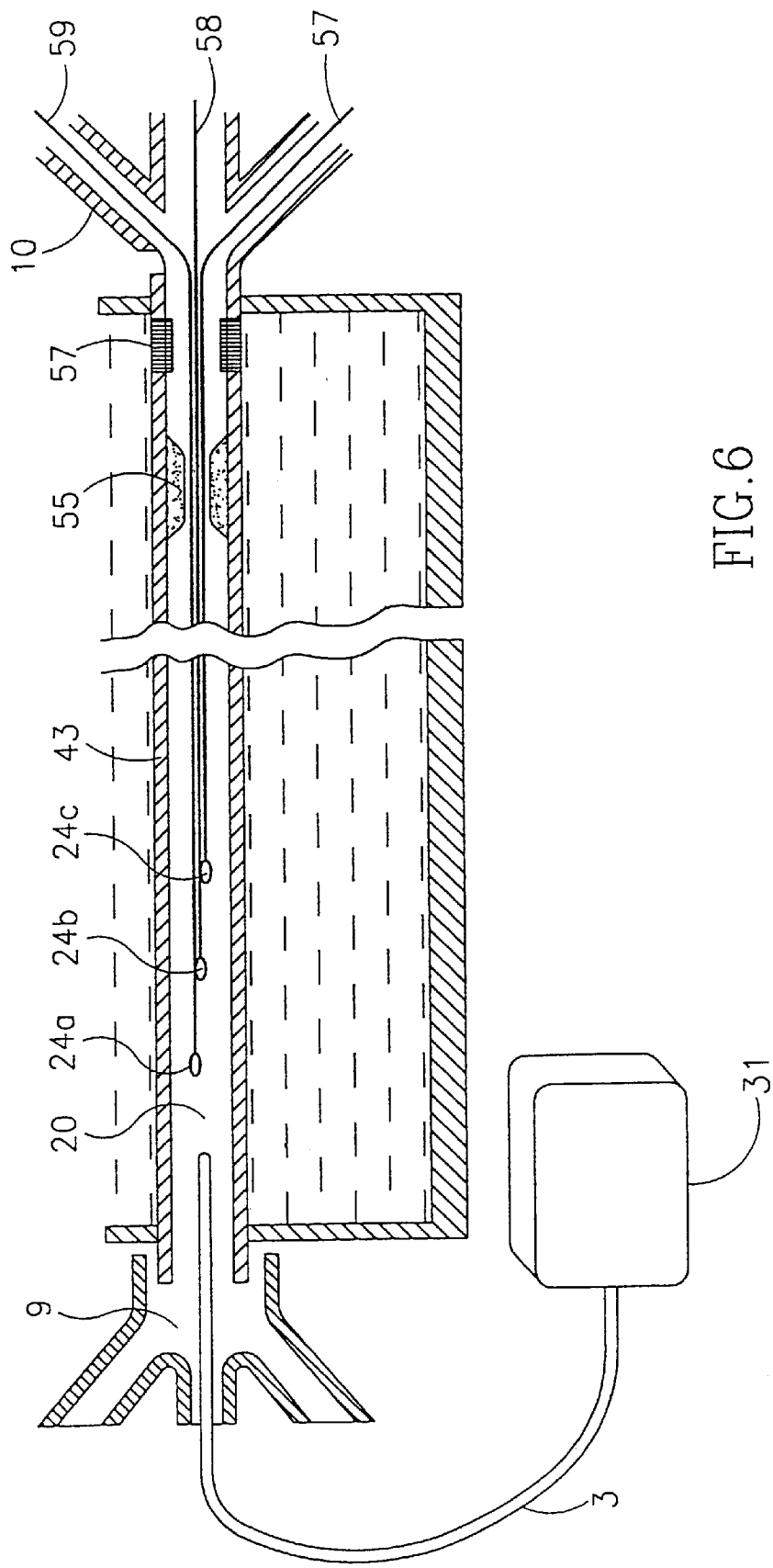
FIG. 6 is a detailed schematic illustration of the experimental section 44 of FIG. 5 and the positioning of the pressure sensors within a the latex tube during the operation of the system of FIGS. 4 and 5.

Reference is now made to FIGS. 4, 5 and 6 for purposes of illustration. FIG. 5 is a schematic diagram representing an in-vitro experimental apparatus constructed and operative for determining flow characteristics in simulated non-lesioned and lesioned blood vessels, in accordance with an embodiment of the present invention. FIG. 2 is a schematic functional block diagram illustrating the functional details of a system including the apparatus of FIG. 5 and apparatus for data acquisition, analysis and display.

The fluidics system 51 of FIG. 5 is a recirculating system for providing pulsatile flow. The system 51 includes a pulsatile pump 42 (model 1421A pulsatile blood pump, commercially available from Harvard Apparatus, Inc., Ma, U.S.A.). The pump 42 allows control over rate, stroke volume and systole/diastole ratio. The pump 42 re-circulates distilled water from a water reservoir 15 to a water reservoir 14.

The system 51 further includes a flexible tube 43 immersed in a water bath 44, to compensate for gravitational effects. The flexible tube 43 is made from Latex and has a length of 120 cm. The flexible tube 43 simulates an artery. The flexible tube 43 is connected to the pulsatile pump 42 and to other system components by Teflon tubes. All the tubes in system 51 have 4 mm internal diameter. A bypass tube 45 allows flow control in the system and simulates flow partition between blood vessels. A Windkessel compliance chamber 46 is located proximal to the flexible tube 43 to control the pressure signal characteristics. A Windkessel compliance chamber 47 and a flow control valve 48 are located distal to the flexible tube 43 to simulate the impedance of the vascular bed. The system 51 of FIG. 5 further includes an artificial stenosis made of a tube section 55, inserted within the flexible tube 43. The tube section 55 is made from a piece of Teflon tubing. The internal diameter 52 (not shown) of the artificial stenosis 45 may be varied by using artificial stenosis sections fabricated separately and having various internal diameter.

Reference is now made to FIG. 6, which is a schematic cross sectional view illustrating a part of the fluidics system 51 in detail. Pressure is measured along the flexible tube 43 using a pressure measurement system including MIKRO-TIP pressure catheters 57,58 and 59, and SPC-320, SPC-721 or SPC-524 pressure catheter, connected to a model TCB-500 control unit, commercially available from Millar Instruments Inc., TX, U.S.A. The catheters 57,58 and 59 are inserted into the flexible tube 43 via the connector 10, connected at the end of the flexible tube 43. The catheters 57,58 and 59 include pressure sensors 24A, 24B and 24C, respectively, for pressure measurements. A fluid filled pressure transducer 31 is connected to the system 51 via the end of the guiding catheter 3, inserted into the flexible tube 43 via the connector 9. The fluid filled pressure transducer 31 is connected to the system 51, when additional pressure readings are needed, or in place of an intravascular pressure transducer, according to the defined experiment.

The system 51 of FIG. 5 also includes a flowmeter 11 connected distal to the flexible tube 43 and a flowmeter 12 connected to the bypass tube 45. The flowmeters 11 and 12 are suitably connected to the A/D converter 28. The flowmeters 11 and 12 are model 111 turbine flow meters, commercially available from McMillan Company, TX, U.S.A.

Reference is now made to FIG. 4. The system 41 includes the system 51. The system 41 also includes a signal conditioner 23, of the type sold as model TCB-500 control unit commercially available from Millar Instruments. The signal conditioner 23 is suitably connected to the pressure sensors 24A, 24B and/or 24C for amplifying the pressure signals. The system 41 further includes an analog to digital converter 28 (E series Instruments multifunction I/O board 28) model PC-MIO-16E-4, commercially available from National Inc., TX, U.S.A.) connected to the signal conditioner 23 for receiving the conditioned analog signals therefrom. The system 41 also includes a signal analyzer 25 connected to the A/D converter 28 for receiving the digitized conditioned pressure signals from the A/D converter 28. The signal analyzer 25 includes a computer (Pentium 586) 20, a display 21 connected to the computer 20 for displaying text numbers and graphs representing the results of the calculations performed by the computer 20. A printer 26 is suitably connected to the computer 20 for providing hard copy of the results for documentation and archiving. The computer 20 processes the pressure data which is sensed by the pressure sensors 24A, 24B and 24C and acquired by the A/D converter 28 and generates textural, numerical and graphic data that is displayed on the display 21.

The I/O board was controlled by a Labview graphical programming software, commercially available from National Instruments Inc., TX, U.S.A. 10 sec interval of pressure and flow data were sampled at 5000 Hz, displayed during the experiments on the monitor and stored on hard disk. Analysis was performed offline using Matlab version 5 software, commercially available from The MathWorks, Inc., MA U.S.A.

The system uses various methods to determine the hemodynamic parameters defined herein above: CFR, DSVR, and FFR. All the methods are based on measurement or calculation of the pressure gradient (pressure drop) between two points along a blood vessel or tubular conduit. These two points may be located proximal and distal to a stenosis, an aneurysm or a section of the vessel where the wall characteristics are of interest.

The methods described herein below are more efficient and accurate than the existing tools and methods. First, the possibility to obtain multiple parameters in one procedure with one set of equipment allows the physician to gain a more comprehensive estimation of the vascular bed condition. Second, the pressure based CFR estimation presented herein is more accurate and robust than the velocity based CFR. The reasons for this include the change in the velocity profile between rest and vasodilatation conditions, the errors introduced due to mal-positioning of the sensor within the vessel cross-section and also patient breathing and motion.

Lastly, the methods presented here are less sensitive to instability (drift of jump) of the pressure transducers, and when instability is identified, correcting procedure is short and presents no further risk to the patient (no need to re-cross the lesion).

Figure 7:
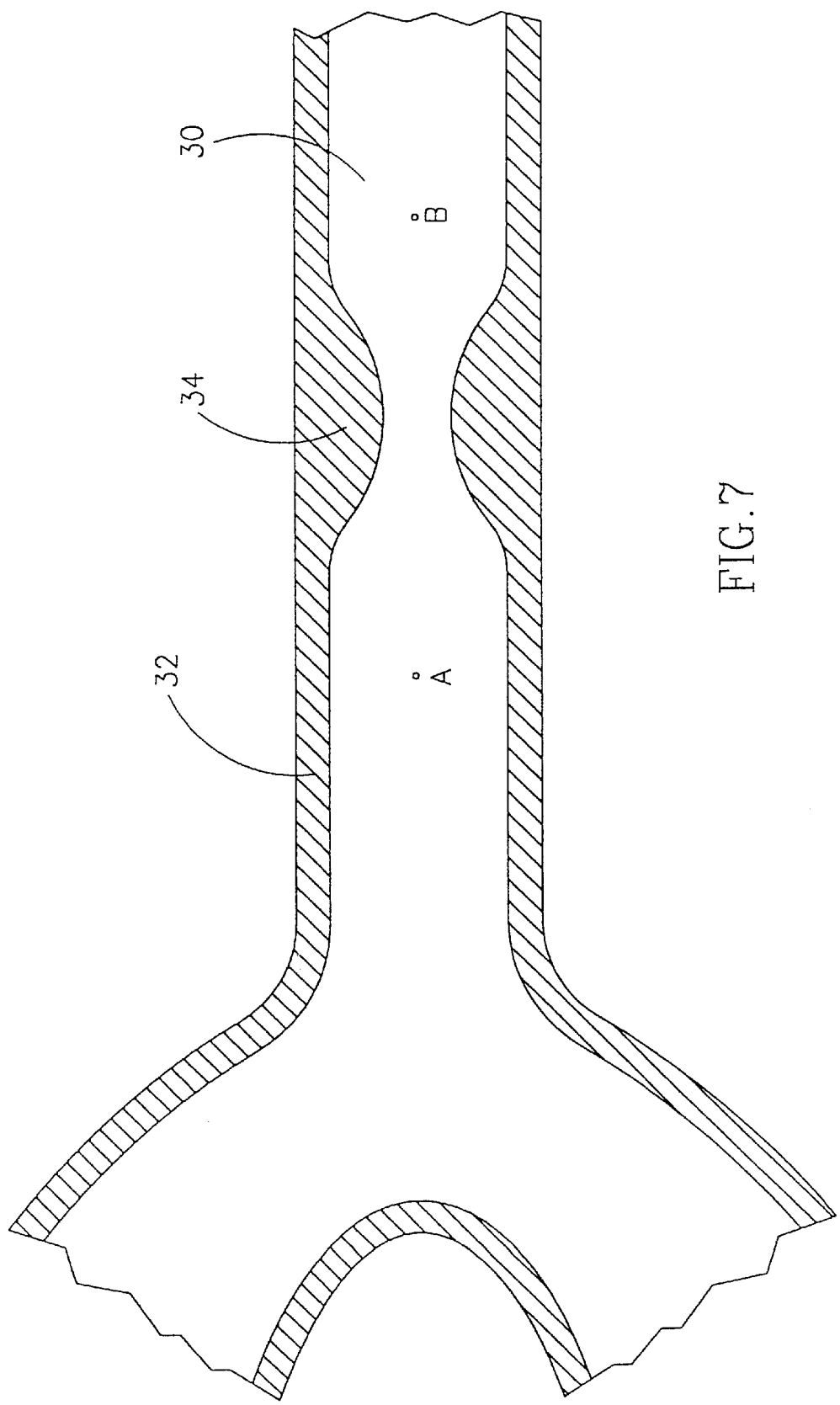
FIG. 7 is a schematic cross section illustrating an artery with a stenosis and points A and B designating pressure measurement points.

Reference is now made to FIG. 7 describing a section of blood vessel 30 having an arterial wall 32. The artery 30 may also include a stenosis 34, obstructing the blood flow. Points A and B are located proximal and distal to the stenosis. The pressure over time, $P_A(t)$ and $P_B(t)$, enable the calculation of the above mentioned parameters.

Depending on the parameter of interest, measurements of the pressure gradient across the stenosis or aneurysm during various physiological conditions are needed:

1. REST condition: The patient is in normal condition, without any effect of dragues causing changes in blood pressure or flow rate.
2. HYPEREMIA/VASODILATATION condition: The patient is under the influence of dragues causing dilatation of the vascular bed, resulting in an increase blood flow rate.
3. SYSTOLE
4. DIASTOLE

CFR CALCULATION

In order to estimate the CFR value, pressure measurements are performed with the patient in REST and HYPEREMIA conditions. CFR parameter is calculated using the following equation:

$$CFR = \frac{\int_0^T \sqrt{(Pv_A - Pv_B) \cdot dt}}{\sqrt{(Pr_A - Pr_B) \cdot dt}}$$

where $Pv_A$ and $Pv_B$: Pressure during hyperemia at points A and B, respectively.

$Pr_A$ and $PR_B$: Pressure at rest at points A and B, respectively.

t: Time

T: Time of one heat beat

CFR CALCULATION: using maximal diastolic flow maximum

Figure 11:
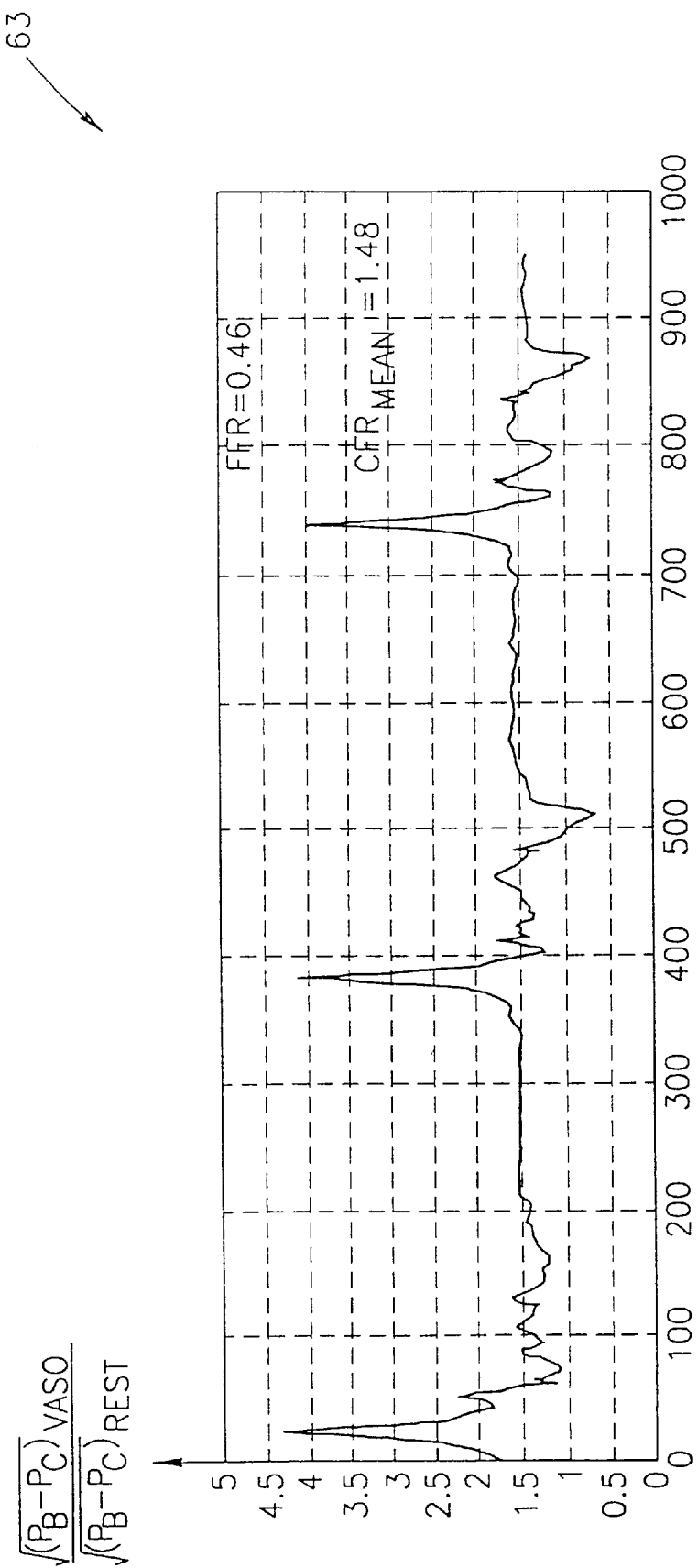
FIG. 11 presents the result of the calculation performed on the data shown in FIG. 11.

The method of CFR calculation uses the pressure difference across the stenosis over a full heartbeat. The methods provided herein provide for the calculation of CFR as the ration of the flow diastolic maximum during vasolidation and at rest (FIG. 40). As shown in FIG. 11, the ratio of flows during vasolidation and rest is almost constant during systole. Hence, as provided herein, CFR may be calculated as a ratio of maximal flows at rest and during vasolidation. The flow is proportional to the square root of the pressure difference across a stenosis, yielding the following equation:

$$CFR = \frac{\max_{diastole} \left( \sqrt{P_{VA} - P_{VB}} \right)}{\max_{diastole} \left( \sqrt{P_{VA} - P_{VB}} \right)}$$

This method of CFR calculation is beneficial for stenosis with small mean pressure gradient at rest. The maximal diastolic flow may be 1.5–2 times higher then the mean flow. Therefore, the maximal flow pressure gradient at rest is 2–4 times higher than the mean pressure gradient. As a result, good estimation of the CRR may be achieved even for pressure gradient at rest of 1–2 mmHg or less. This reduces a limitation is calculating the CFR parameter in cases where the pressure gradient across the stenosis is very low. Consequently, allowing the calculation of the CFR parameter in most cases. Accordingly, the present invention provides a method which incorporates calculating CFR using flow integral or using maximal diastolic flow as hereinabove described.

DSVR CALCULATION

In order to estimate DSVR, pressure data is required at REST condition only. The pressure gradient between points A and E during diastole and during systole are calculated separately. Therefore, simultaneous pressure data at points A and B are required during systole and diastole. DSVR parameter is calculated using the following equation:

$$DSVR = \frac{\int_{diastole} (Prd_A - Prd_B) \cdot dt}{\int_{systole} (Prs_A - Prs_B) \cdot dt}$$

where:

$Prd_A$: pressure at point A at rest during diastole $Prd_B$: pressure at point B at rest during diastole $Prs_A$: pressure at point A at rest during systole $Prs_B$: pressure at point B at rest during systole

FFR CALCULATION

In order to estimate FFR, pressure data during HYPEREMIA condition is required.

FFR parameter is calculated using the following equation:

$$FFR = \frac{Pv_B}{Pv_A}$$

where:

$Pv_B$: Mean pressure at point B during hyperemia $Pv_A$: Mean pressure at point A during hyperemia

METHOD 1: SIMULTANEOUS TWO SITES PRESSURE MEASUREMENTS

Figure 8:
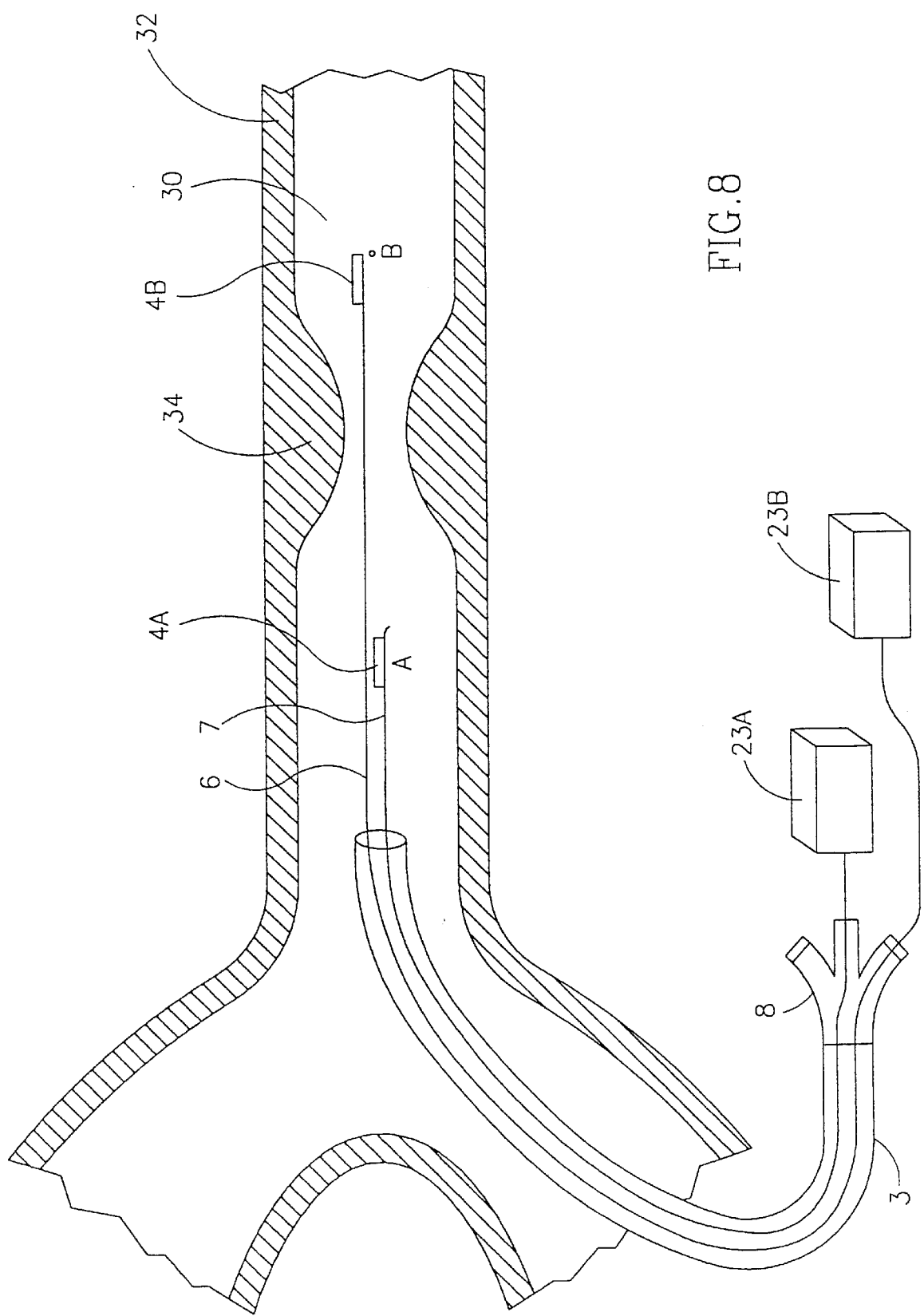
FIG. 8 is a schematic cross section of a blood vessel, illustrating the positioning of the two pressure sensors used in Method 1.

Reference is now made to FIG. 8, illustrating a cross section of an artery 30 having an arterial wall 32 and stenosis 34. Two points, A and B proximal and distal to the stenosis define a section of the artery. The hemodynamic parameters: CFG, DSVR, and FFR, along this section are of interest.

A guiding catheter 3 (or diagnostic catheter, or any other hollowed catheter) is inserted into the blood vessel of interest. Two guide wires 6 and 7, each having a pressure sensor at the tip 4A or 4B, are inserted through the guiding catheter and positioned so that one pressure sensor (4A) is located at point A, proximal to the stenosis, and the second pressure sensor (4B) is located at point B, distal to the stenosis. Both pressure sensors are connected to signal conditioners 23A and 23B, of the kind described in FIGS. 1, 1.a and 2, 2.a.

DATA ACQUISITION

The following steps are performed to obtain the required data:

Step 1: Simultaneous measurement of pressure is performed by the two pressure sensors, yielding $Pr_A(t)$ and $Pr_B(t)$. The measurement is performed while the patient is at rest.

Step 2: Simultaneous measurement of pressures is performed again, by the two pressure sensors, yielding $Pv_A(t)$ and $Pv_B(t)$. The measurement is performed while the patient is under the effect of vasodilation dragues.

DATA ANALYSIS

All 3 parameters (CFR, DSVR, and FFR) are calculated using the equations mentioned herein above.

METHOD 2: SIMULTANEOUS TWO SITES PRESSURE MEASUREMENT USING A FLUID FILLED PRESSURE TRANSDUCER

Figure 9:
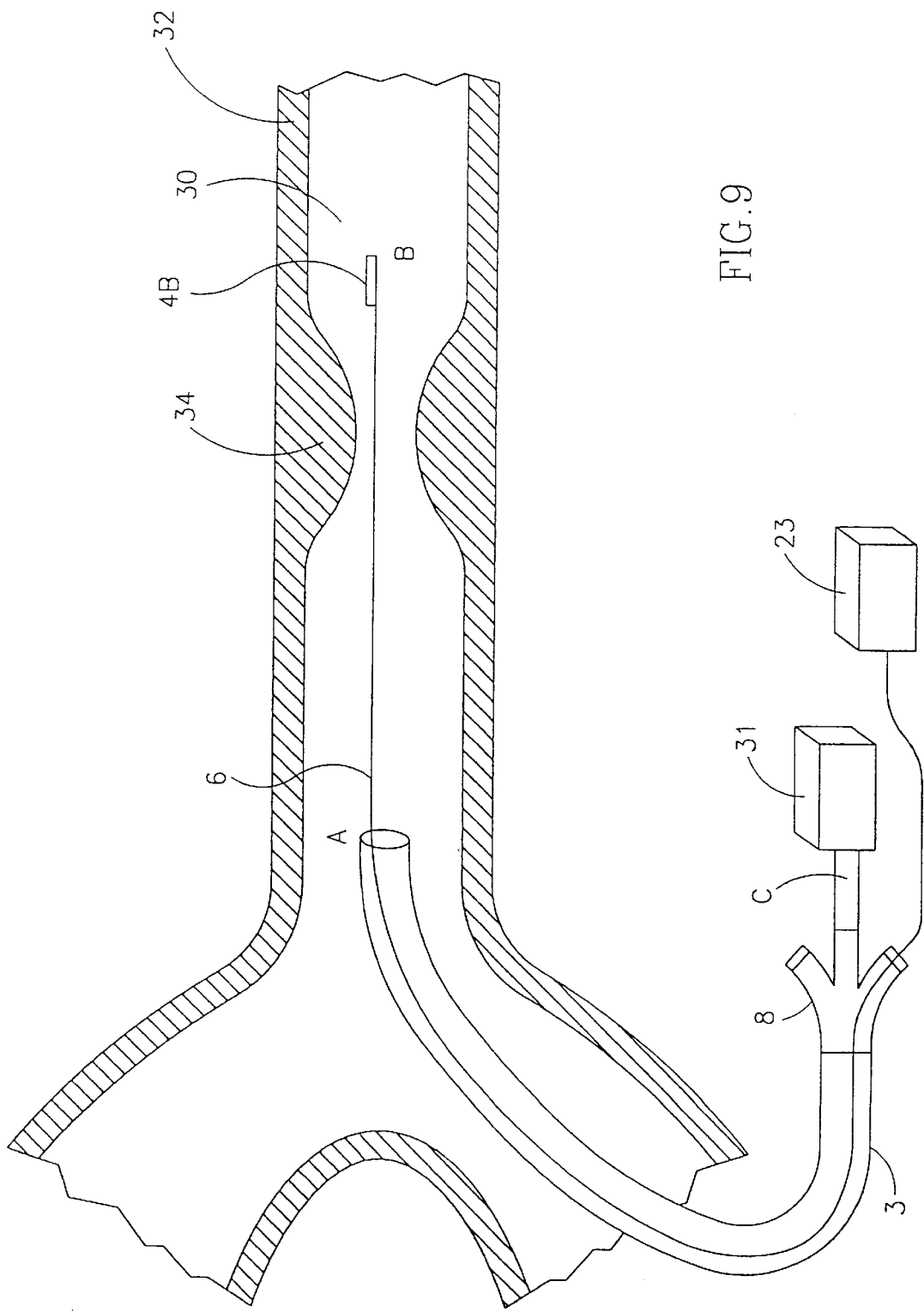
FIG. 9 is a schematic cross section of a blood vessel, illustrating the positioning of the pressure sensors used in Method 2.

Reference is now made to FIG. 9, illustrating a cross section of an artery 30 with an arterial wall 32 and a stenosis 34. Two points A and B upstream and downstream of the stenosis define a section of the artery. The hemodynamic parameters: CFR, DSVR, and FFR, of this section are of interest.

A guiding catheter 3 (or diagnostic catheter, or any other hollowed catheter) is inserted into the blood vessel of interest. The tip of the catheter is positioned at point A, at the proximal section of the vessel. A pressure fluid filled transducer 31 is connected to the external end of the catheter (point C) and measures the pressure at that point. A single guide wire (6) having a pressure sensor at its tip (4B), is inserted trough the guiding catheter and positioned so that the pressure sensor 4B is located at point B. The pressure sensor is connected to a signal conditioner 23 as described in FIGS. 1, 1.$a$ and 2,2.$a$.

The pressure gradient between points A and C ($P_A$–$P_C$) are known to be small. Therefore, it is assumed that $P_A$ ($P_C$. In cases of severe or moderate stenosis, the pressure gradient is $P_B$–$P_C$>10 mmHg. The pressure difference $P_A$–$P_C$ is negligible (comparing to $P_B$–$P_C$). Therefore, the assumption that $P_A \approx P_C$ does not affect the coefficients (CFR, DSVR and FFR) calculated values. In cases of light stenosis the use of this method is not recommended.

In another embodiment the pressure measured by the Pressure Wire, the mean fluid filled pressure pulse ff_m is corrected in accordance with the floowing equation: for every pulse the correct pressure P measured by the Pressure Wire multiplicatively is Pc(t)=P(t)*ff(t)/ff_m(t). Here Pc(t) corrected pressure, ff(t) pressure measured by fluid filled manometer.

DATA ACQUISITION

The following steps are performed to obtain the required data:

Step 1: Simultaneous measurement of pressure is performed by the two pressure sensors, yielding $Pr_C(t)$ and $Pr_B(t)$. The measurement is performed while the patient is at rest.

Step 2: Simultaneous measurement of the pressure is repeated, yielding $Pv_C(t)$ and $Pv_B(t)$. The measurement is performed while the patient is at vasodilatation condition.

DATA ANALYSIS $P_A$ is considered to be equal to $P_C$, ($P_A \approx P_C$). All 3 parameters (CFR, DSVR, and FFR) are calculated using the equations described herein above.

CLINICAL EXAMPLE

Human test data are used to demonstrate the implementation of this method. Pressure measurements were performed during rest and vasodilatation conditions. The pressure was measured proximal to the stenosis (point A of FIG. 9) using a fluid filled pressure sensor, and distal to the stenosis (point B of FIG. 9) using Radi pressure wire.

Figure 10:
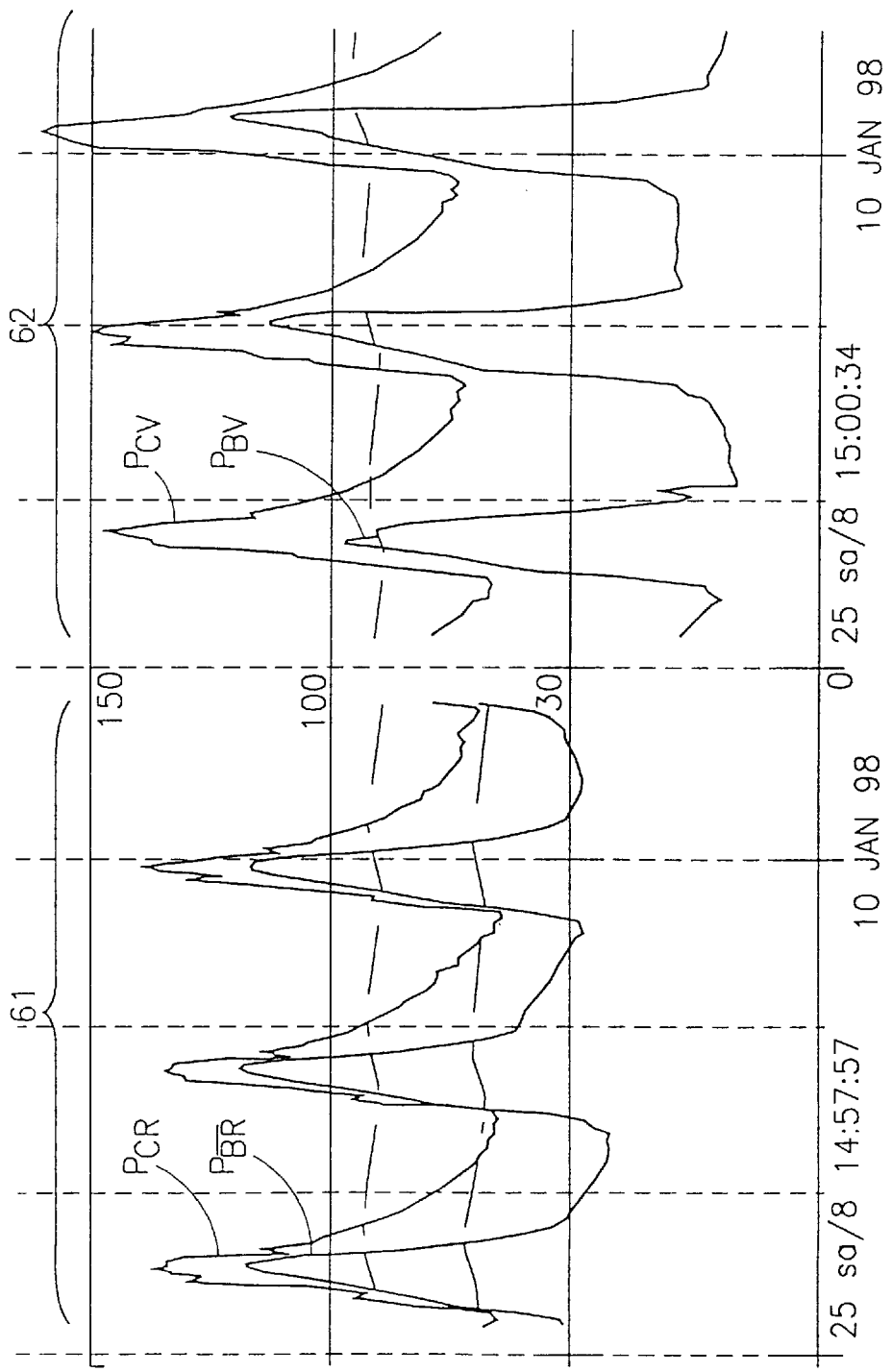
FIG. 10 presents an example of pressure data used by Method 3 to determined hemodynamic coefficients.

Reference is now made to FIG. 10, illustrating the data acquired on paper (velocity of 25 mm/sec). The data was digitized using a computer software Graph 61 illustrates pressure data versus time during rest. Curves Pcr and Pbr describe the pressure at points C and B, respectively. Graph 62 illustrates pressure data versus time during vasodilatation. Curves Pcv and Pbv describe the pressure at points C and B, respectively. Due to the high pressure gradient across the stenosis (more than 10 mmHg at rest condition), the pressure measured by the fluid filled manometer (Pc) may be used instead of pressure data at point A.

Reference is now made to FIG. 11. Graph 63 illustrates the calculated non-dimensional flow ratio versus time, derived as $$\frac{\sqrt{(Pb-Pc)_{vaso}}}{\sqrt{(Pb-Pc)_{rest}}}$$

Then, the parameters CFR and FFR are calculated: FFR=0.46 and CFR=1.48.

IN-VITRO EXAMPLE

In vitro experimental was performed, using the in-vitro test system described in FIGS. 4, 5 and 6. The experimental section included an artificial stenosis (90% area reduction). Two pressure sensors (Millar SPC-524) were located, one 2 cm proximal to the stenosis and the second 2 cm distal to stenosis. The system was running with a glycerin water solution to simulate blood viscosity.

The system was run in two different modes to simulate rest and vasodilatation conditions. These modes were obtained by changing three variables of the in-vitro system including the pump flow, the bypass opening and closure, and the height of the output reservoir. Yielding various flow levels through the stenosis, with stable physiologic input pressure, simulating the aortic pressure.

Flowmeter 11 data and pressure data from both sensors were obtained in each system mode. Applying the analysis described in Method 2 to this data yields the FFR and CFR values.

The results are presented in Table 1, where the cases refer to different levels of flow through the system:

|  | FFR$_{calculated}$ | CFR$_{calculated}$ | CFR$_{measured}$ |
| --- | --- | --- | --- |
| case 1. | 0.7 | 1.9 | 2.0 |
| case 2. | 0.3 | 2.5 | 2.47 |

A high correlation is observed between CFR value derived from actual flow measurements and from pressure measurements.

METHOD 3: NON-SIMULTANEOUS PRESSURE MEASUREMENTS WITH FLUID FILLED PRESSURE SYNCHRONIZATION

Figure 12:
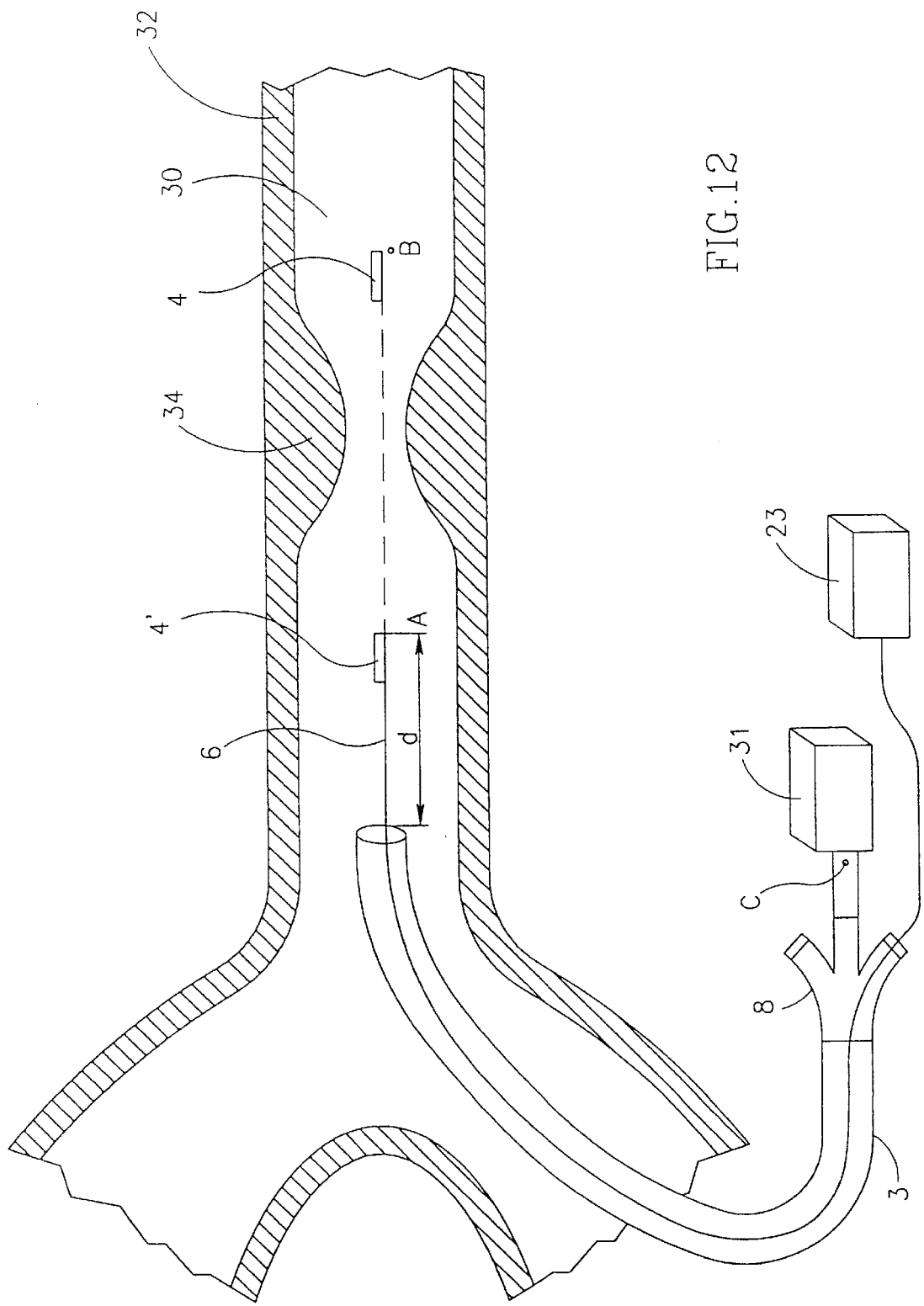
FIG. 12 is a schematic cross section of a blood vessel, illustrating the positioning of the pressure sensors used in Method 3.

Reference is now made to FIG. 12, illustrating a cross section of an artery 30 have an arterial wall 32 and a stenosis 34. Two points, A and B, proximal and distal to the stenosis define a section of the artery. The parameters CFR, DSVR, and FFR of this section are of interest.

A guiding catheter 3 (or diagnostic catheter, or any other hollowed catheter) is inserted into the blood vessel of interest 30. An external fluid filled pressure transducer 31 is connected to the guiding catheter ostium (proximal end), measuring the pressure at point C (referred as fluid field pressure).

One guide wire 6, having a pressure sensor at its tip 4 is inserted through the guiding catheter and positioned so that the pressure sensor 4 is located at point A proximal to the stenosis. The pressure sensor 4 is connected to system 23 described in FIGS. 1, 1.$a$ and 2, 2.$a$. Then, the pressure sensor 4 is moved to point B for further measurements.

DATA ACQUISITION

The following steps are performed to obtain the required data:

Step 1: The pressure sensor 4 is located proximal to the stenosis, at point A.

Step 2: Simultaneous measurement of pressure by the two pressure sensors, 4 and 31 are obtained, yielding $Pr_A(t)$ and $Pr_C(t)$. The measurements are performed while the patient is at real. The pressure sensor 4 is moved to point B, distal to the stenosis.

Step 3: Simultaneous measurement of pressure is performed by the two pressure sensors, 4 and 31. Data of pressure versus time $Pr_B(t)$ and $Pr_C(t)$ is obtained.

Step 4: Inducing vasodilatation

Step 5: Simultaneous measurement of pressure s performed by pressure sensors 4 and 31, yielding $Pv_B(t)$ and $Pv_C(t)$. The measurements are performed during vasodilatation condition.

Step 6: Pressure sensor 4 is moved backward to point A, proximal to stenosis.

Step 7: Simultaneous measurement of pressure is performed by the pressure sensors 4 and 31, yielding $Pv_A(t)$ and $Pv_C(t)$ is obtained.

DATA ANALYSIS

To calculate hemodynamic parameters, simultaneous pressures at points A and B are required. Two independent methods where developed synchronizing the pressure data at rest and vasodilatation conditions. Once all pressures signals are available, the parameters: CFR, DSVR, FFR are calculated using the equations mentioned herein above.

Pressure Transfer Function:

The measurement described previously are used to determine the transfer function of pressure between points C and A (Tca) using data acquired in step 1. Alternatively, transfer function between points C and B (Tcb) can be calculated, using data acquired at step 3. Once the transfer functions are known, pressure data at point A (or B) can be calculated from the known pressure at point C.

Input:
  Data acquired at step 1: $Pr_A1(t)$, $Pr_C1(t)$
  Data acquired at step 3: $Pr_B3(t)$, $Pr_C3(t)$
Steps:
  Step 1: Shift the pressure signal $Pr_C1(t)$ to yield a new pressure signal X1(t) with min [X1(t)]=0, X1(t)=$Pr_C1$(t)−min[$Pr_C1(t)$].
  Step 2: Shift the pressure signal $Pr_A1(t)$ to yield a new pressure signal Y1(t) with min [Y1(t)]=0, Y1(t)=$Pr_A1$(t)−min[$Pr_A1(t)$].
  Step 3: Perform FAST FOURIER TRANSFORM (FFT) on X1(t) and Y1(t):
    Fx=FFT(X1)
    Fy=FFT(Y1)
  Step 4: Calculate the transfer function (H) in Fourier space:
    H=Fy/Fx
  Step 5: Calculate transfer function (Tca) in time space using INVERSE FAST FOURIER TRANSFORM (IFFT): Tca(t)=IFFT(H)
  Step 6: Calculate pressure at point A, $Pr_A3(t)$, from the known pressure at point C, $Pr_C3(t)$, using convolution with the transfer function Tca: $Pr_A3$=CONV(Tca, $Pr_C3$)

Now, the simultaneous pressure proximal and distal to the stenosis is known ($Pr_A3$ and $Pr_B3$). The same procedure is used to determine the simultaneous pressure, proximal and distal to the stenosis during vasodilatation ($Pv_A5$ and $Pv_B5$). The calculation of the parameters CFR, DSVR, and FFR is performed using the equation mentioned herein above.

IN VITRO EXAMPLE

In vitro experiment was performed to validate the transfer function Method 1, using the in-vitro test system described in FIGS. 4, 5 and 6. The system was set to 51 stokes/min and 9 cc/stroke. The system included a Latex test tube with a smooth stenosis model, 2 cm long, with an internal diameter of 2 mm. The stenosis was located 35.8 cm from the left bath edge. Cordis 8F MPA-I was located within the connector 9. One pressure transducer was located along the latex tube. Another pressure transducer was located within the guiding catheter to simulate fluid filled pressure readings.

Figure 13:
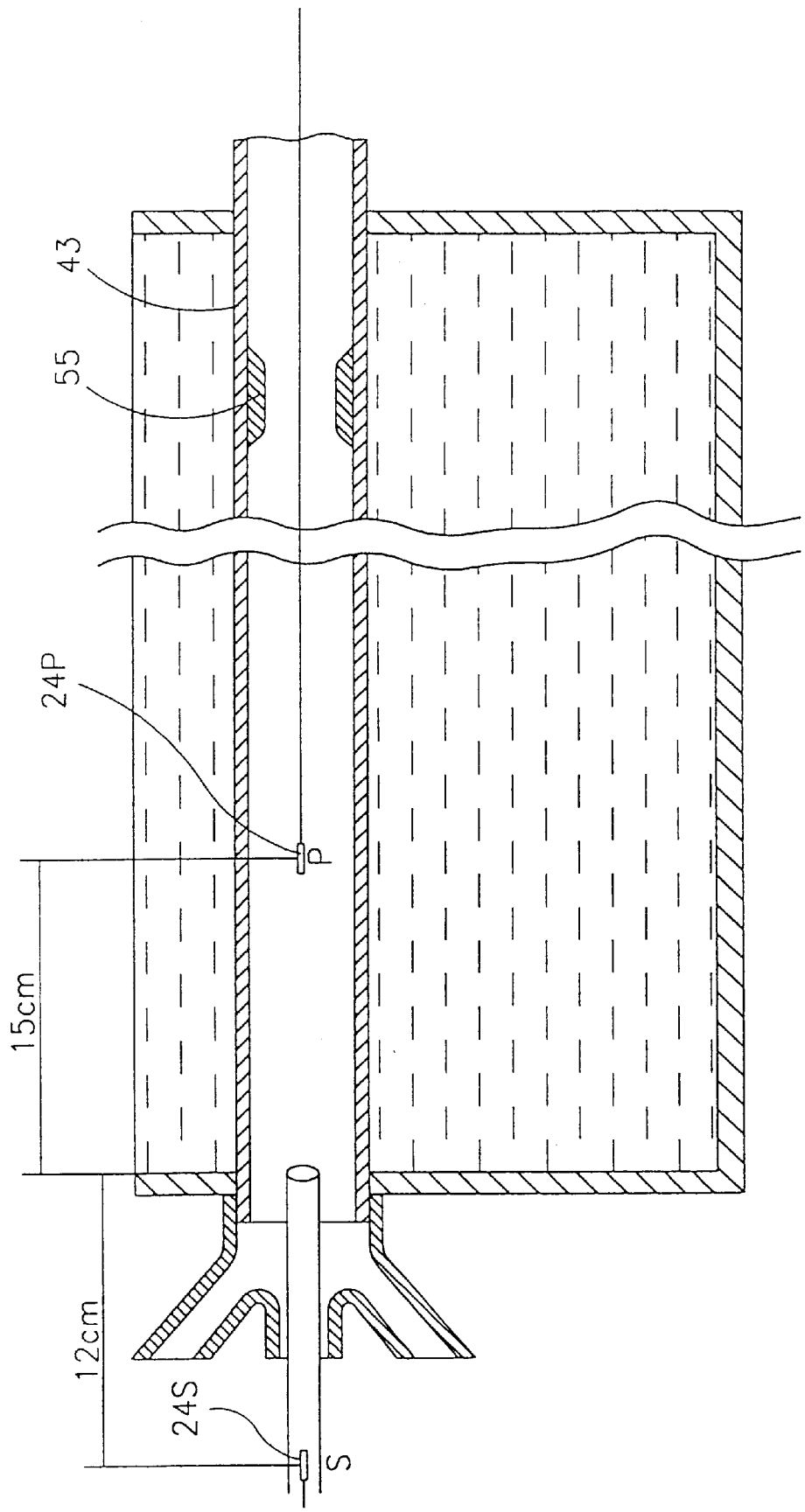
FIG. 13 presents the positioning of pressure sensors and stenosis inside the latex test tube of the in-vitro system of FIGS. 4–6. This configuration was used to validate Method 1, the transfer function method.

Reference is now made to FIG. 13, illustrating the positioning of the pressure sensors 24P and 24S, and the artificial stenosis 55, within the latex test tube, 43. The method 1 is applied to the pressure data at point S and P, to calculate the transfer function between these points, Tsp. Then, the pressure at point D was calculated using the pressure measured at point P, at a different time, and applying the calculated transfer function. This calculated pressure value was compared with the actual pressure at point D as was measured by the sensor 24D during the same heartbeat.

Figure 14:
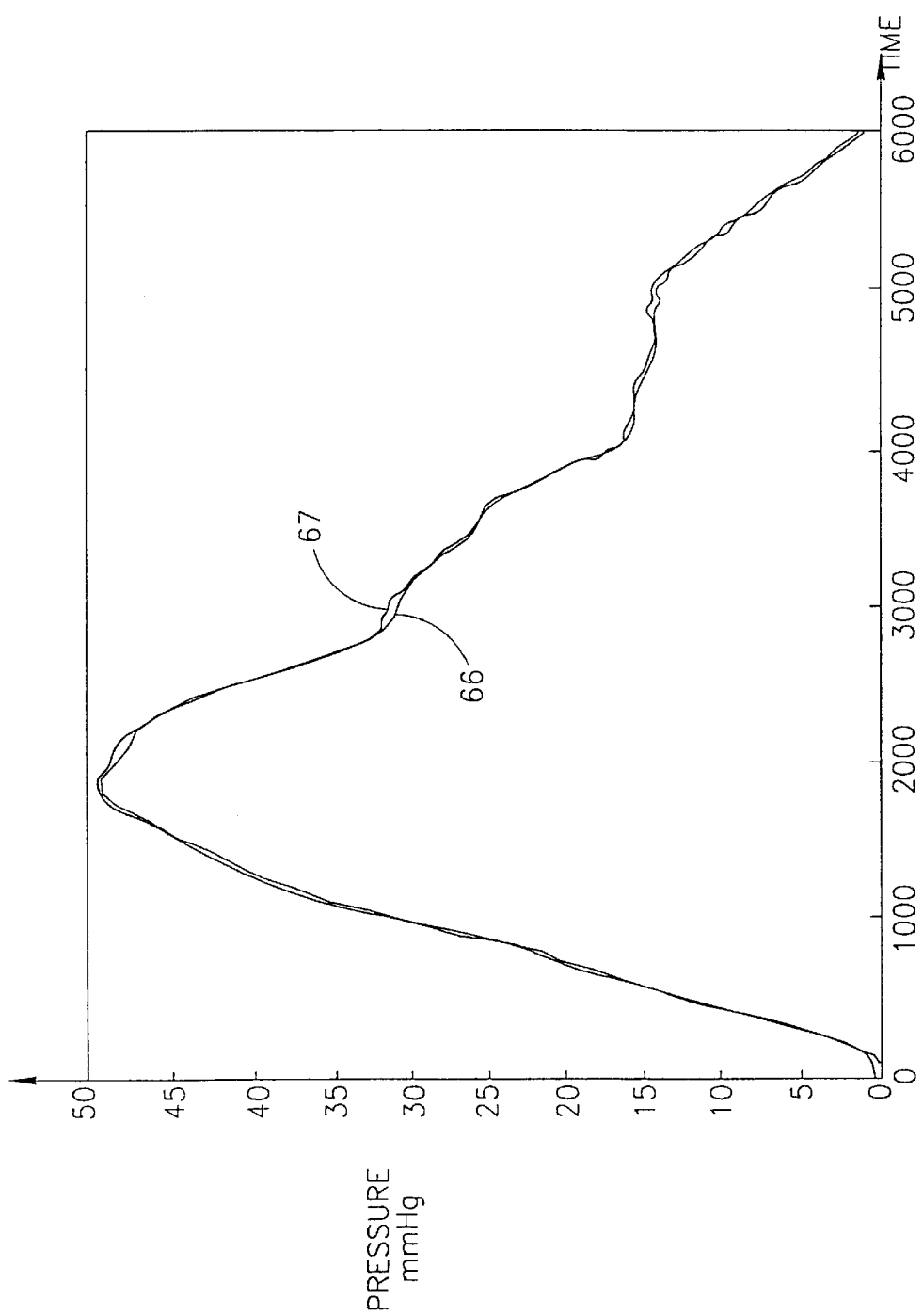
FIG. 14 illustrates a calculated pressure pulse by Method 1, with the actual pressure pulse measured at that point.

The results are described in FIG. 14. The graph designated 66, is the calculated pressure at point P. The graph designated 67, is the actual pressure measurement at point P, as measured by the sensor 24D along the same heartbeat. Almost preferred match exists between the two curves (66 and 67).

Optimal Overlap Method:

The idea of the Optimal Overlap method is based on the observation that fluid filled pressure wave pulse $P_C(t)$ is mathematically similar to $P_A(t)$ but a delayed version of the latter. Thus the best stretching coefficient β and the best delay Δt, for which the function: $\beta \cdot P_2(T+\Delta t)$ is globally close to the foot of $P_A(t)$ is determined. The reason for the appearance of the stretch coefficient (is a possible change in pressure between measurements. Mathematically, a minimum distance in $L_2$ norm, or equivalently a least square criterion is required. Thus, the least square optimal overlap methods can be formulated as follows:

Let i be the index of N successive samples in the foot of the same heart beat (that is from onset of systole to, say 80%, of the maximum of the pressure wave $P_A(t)$) and $t_i$ the corresponding sample times. The optimal overlap criterion reads:

$$\min_{\beta, \Delta t} \sum_{i=1}^{N} (P_1(t_i) - \beta \cdot P_2(t_i - \Delta t))^2$$

Carrying out the partial derivatives with respect to β and Δt, yields the set of implicit equations:

$$\beta = \frac{\sum_{i=1}^{N} P_1(t_i) \cdot P_2(t + \Delta t)}{\sum_{i=1}^{N} P_2^2(t_i + \Delta t)}$$

Let $P'_2(t)$ be the derivative of $P_2(t)$. Then the second non-linear and implicit equation reads;

$$\sum_{i=1}^{N} P_1(t_i) = P'_2(t_i + \Delta t) = \beta \cdot \sum_{i=1}^{N} P_2(t_i + \Delta t) \cdot P'_2(t_i + \Delta t)$$

From these two equations β and Δt are calculated and then used to synchronize pressure measured by pressure transducers at points A and C. Then the pressure at point A, $P_A(t)$, is known from the pressure measured at point C, $P_C(t)$.

METHOD 4: NON-SIMULTANEOUS PRESSURE MEASUREMENTS WITH ECG SIGNALS SYNCHRONIZATION

Reference is now made to FIG. 12, illustrating a cross section of an artery 30 having an arterial wall 32 and a stenosis 34. Two points A and B upstream and downstream of the stenosis define a section of the artery. The hemodynamic parameters: CFR, DSVR, and FFR, along this section are of interest.

A guiding catheter 3 (or diagnostic catheter) is inserted into the blood vessel of interest. An external fluid filled pressure transducer 31 is connected to the guiding catheter entrance (proximal end) measuring the pressure at point C (fluid filled pressure).

A guide wire 6 having a pressure sensor at its tip 4 is inserted through the guiding catheter and positioned so that the pressure sensor 4 is located at point A downstream the stenosis. Both pressure sensors 4 and 31 are connected to the system 23 described in FIG. 1, 1.a and 2,2.a.

Simultaneous ECG data is collected using standard available, at all times, in all catheterization procedures.

DATA ACQUISITION

The following steps are performed to obtain the required data:

Step 1: Simultaneous pressure and ECG measurements are performed. Pressure are measured by two pressure sensors 4 and 31. Data of pressure versus time $Pr_A(t)$ and $Pr_C(t)$ and ECG are acquired, while the patient is at rest condition.

Step 2: Pressure sensor 4 is moved to point B, distal to stenosis.

Step 3: Simultaneous measurements of pressure and ECG are repeated, yielding data of pressure versus time $Pr_B(t)$ and $Pr_C(t)$ and ECG.

Step 4: Induce vasodilatation.

Step 5: Simultaneous measurement of ECG and pressure is repeated, yielding data of pressure versus time $Pv_B(t)$ and $Pv_C(t)$, and ECG. The measurement are performed while the patient is at vasodilatation condition.

Step 6 (optional): Pressure sensor 4 is pulled back to point A, proximal to stenosis while simultaneous measurements of pressure and ECG are performed. Data of pressure versus time $Pv_A(t)$ and $Pv_C(t)$ and ECG chart are obtained.

DATA ANALYSIS

To calculate hemodynamic parameters, simultaneous pressure at points A and B during rest and vasodilatation are required. The pressures at points A and B during rest are measured, but non-simultaneously. Time synchronization is performed using the idea that the ECG signals are stable while measuring pressure at points A or B. Therefore, synchronizing the ECG signals, results in synchronization of the pressure signals at points A and B. Synchronization is achieved by applying Method 2, with the ECG signals used instead of the fluid filled pressure signals. For the vasodilatation condition, it is possible to measure pressure only at point B (downstream). The enlargement of the vessel wall during vasodilatation is negligible proximal to the stenosis, at point A. Therefore, it can be assumed that $Pv_A=Pr_A$, and step 6 of this method may be skipped. The simultaneous pressures at point A and B during vasodilatation is calculated. Then, the parameters CFR, DSVR and FFR are derived using the equations mentioned herein above.

CLINICAL TEST EXAMPLE 1

Data of pressure measurements of a 70 years old woman were used for estimation of CFR, DSVR and FFR. The patient had two lesions in the mid and distal sections of the LAD.

Figure 15:
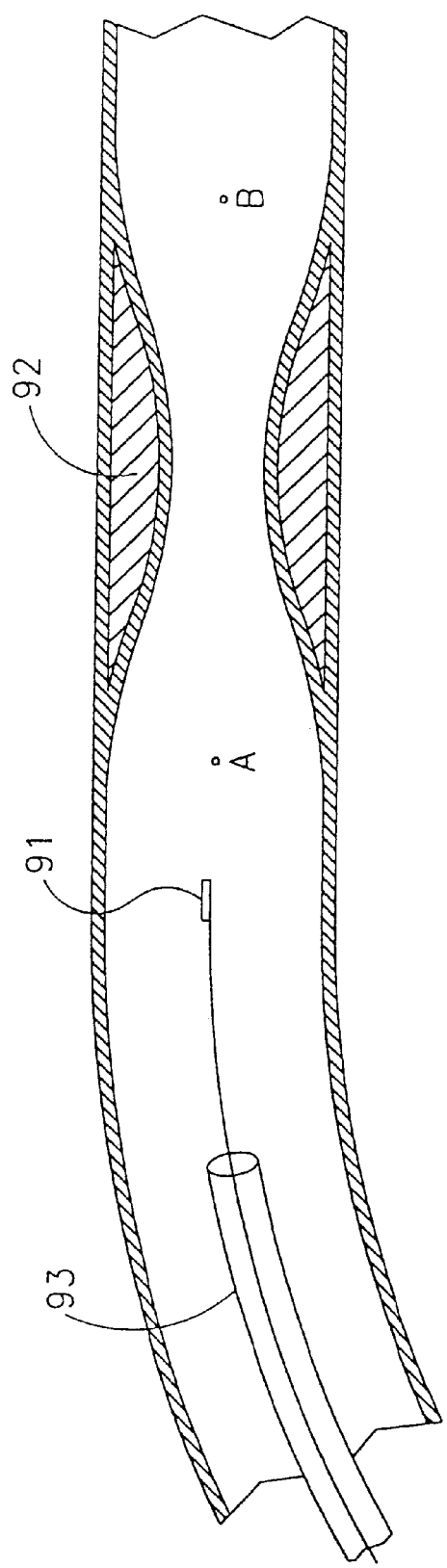
FIG. 15 illustrates an artery with a stenosis, a fluid filled pressure catheter and a pressure wire. Points A and B designate measurements points.

Reference is now made to FIG. 15. Aortic pressure was measured with a fluid filled manometer (not shown) connected to the guiding catheter 93. Pressure in the LAD artery was measured using a Radi pressure wire 91 at point A upstream of the stenosis 92. Then, the pressure wire 91 was moved to measure the pressure at point B downstream of the stenosis. Measurements at point A were made during rest, and at point B and C, during rest and during intracoronary adenosine injection (vasodilatation condition). Pressure signals from the fluid filled manometer, Radi guidewire pressure sensor 91 and ECG were simultaneously recorded and stored with sampling rate of 1 kHz.

Figure 16:
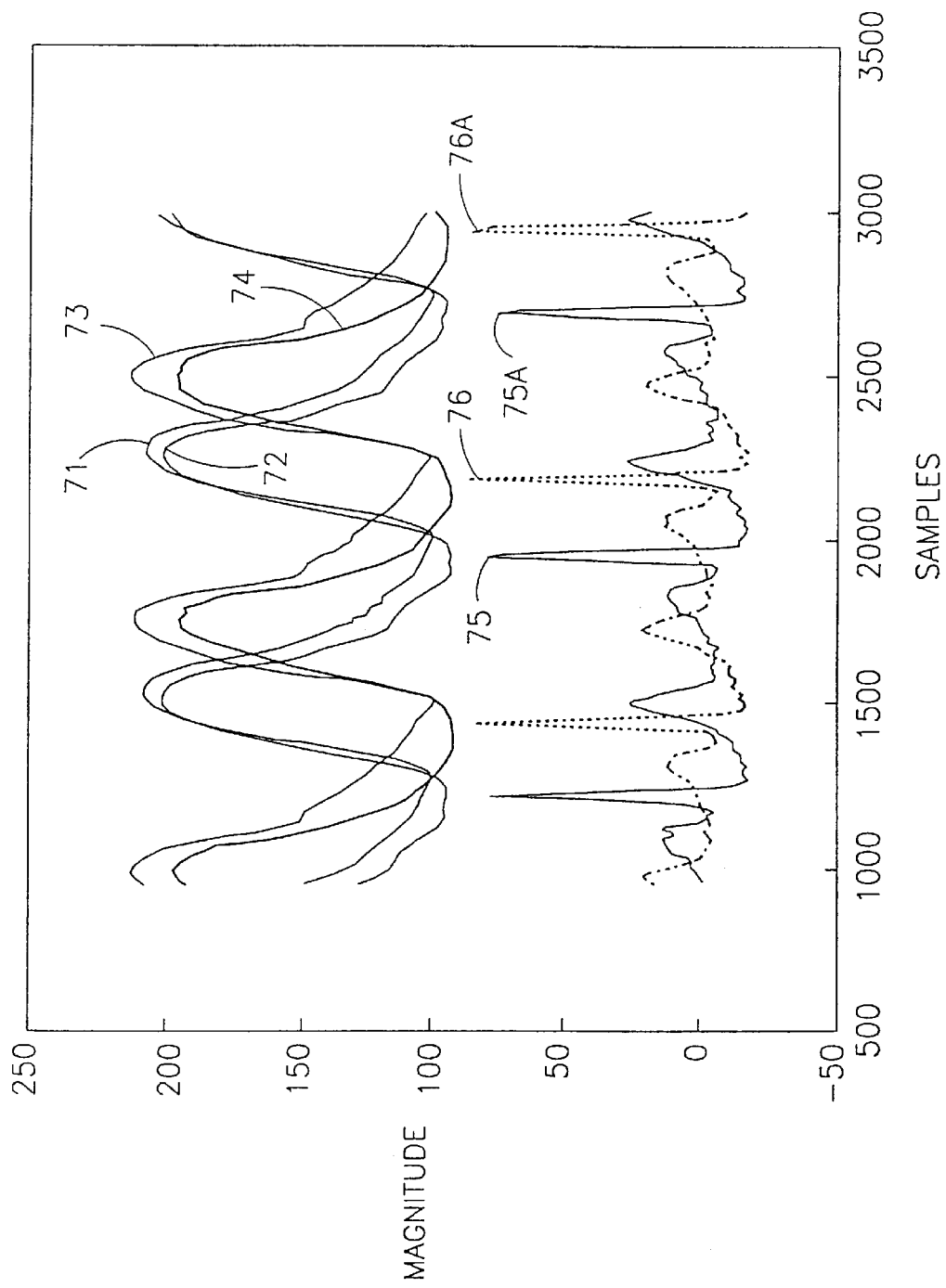
FIG. 16 presents pressure and ECG data, measured on human at rest condition, used by Method 4.

Data analysis included in the calculation of CFR, DSVR and FFR using ECG synchronization. Reference is now made to FIG. 16, illustrating the pressure and ECD signals measured at rest (Radi pressure wire is located at point A and subsequently at point B). Curve 71 is the fluid filled pressure and Curve 72 is the pressure measured by sensor 91, when the Radi pressure wire is at point A. Curve 73 is the fluid filled pressure and Curve 74 is the Radi pressure measured at point B. Curve 75 is the ECG signal measured when Radi pressure wire is at point A. Curve 76 is the ECG signal measured when Radi pressure wire is at point B.

Figure 17:
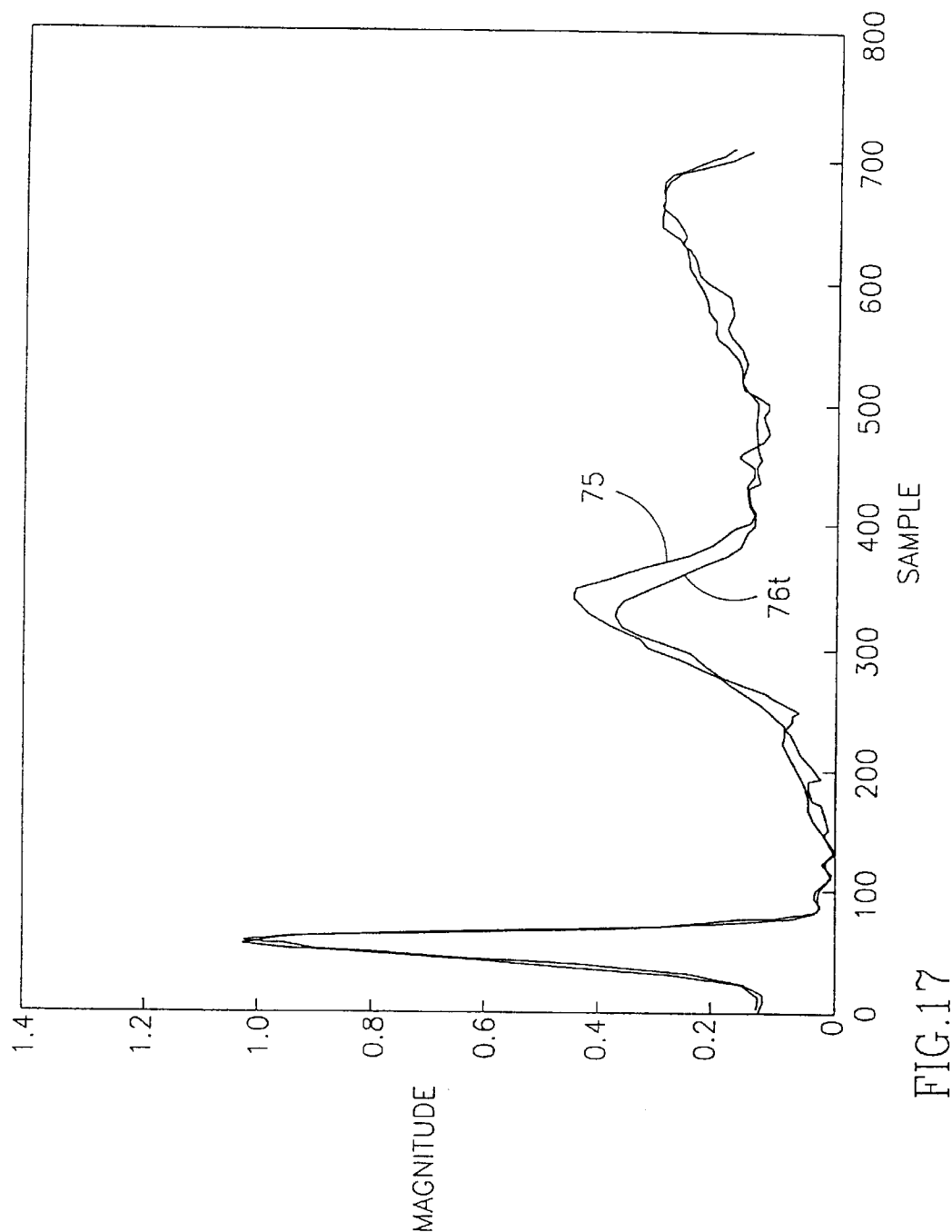
FIG. 17 presents the ECG signals, at rest, after time transformation. The transformation is done using Method 2.

The Optimal Method is used to move the section assigned 76–76a of the ECG signal 76 (measured when pressure sensor 91 is at point B) to the section 75–75a of the ECG signal 75 (measured when Radi pressure wire is at point A). Linear time transformation is applied to the signal 76, in order to match the time length of the signals 75–75a and 76–76a. The result of this transformation is shown in FIG. 17, where the Curve 76t is the transformed ECG curve 76.

Figure 18:
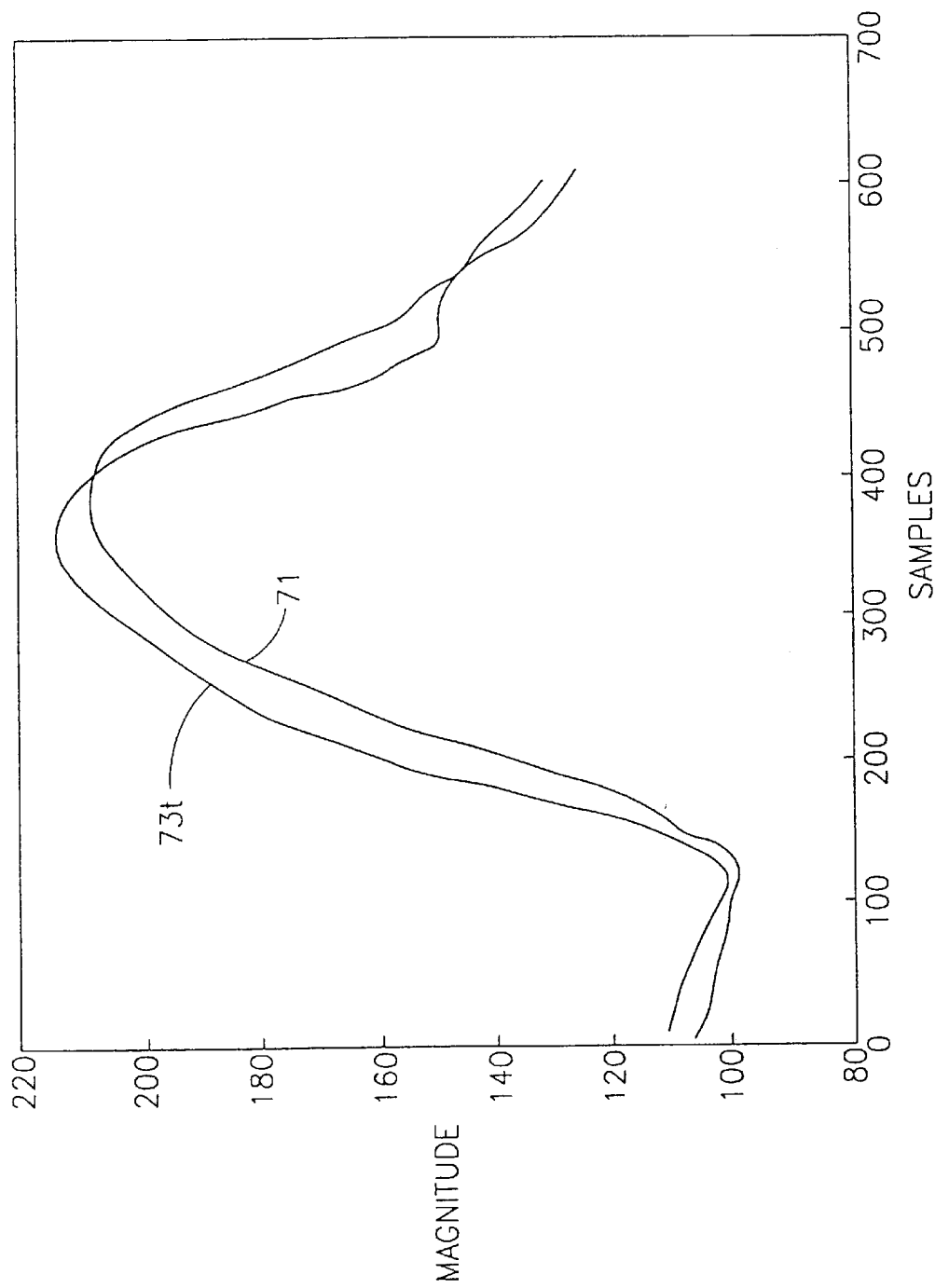
FIG. 18 represents the fluid filled catheter pressure signals at rest and after synchronization of the pulses.
Figure 19:
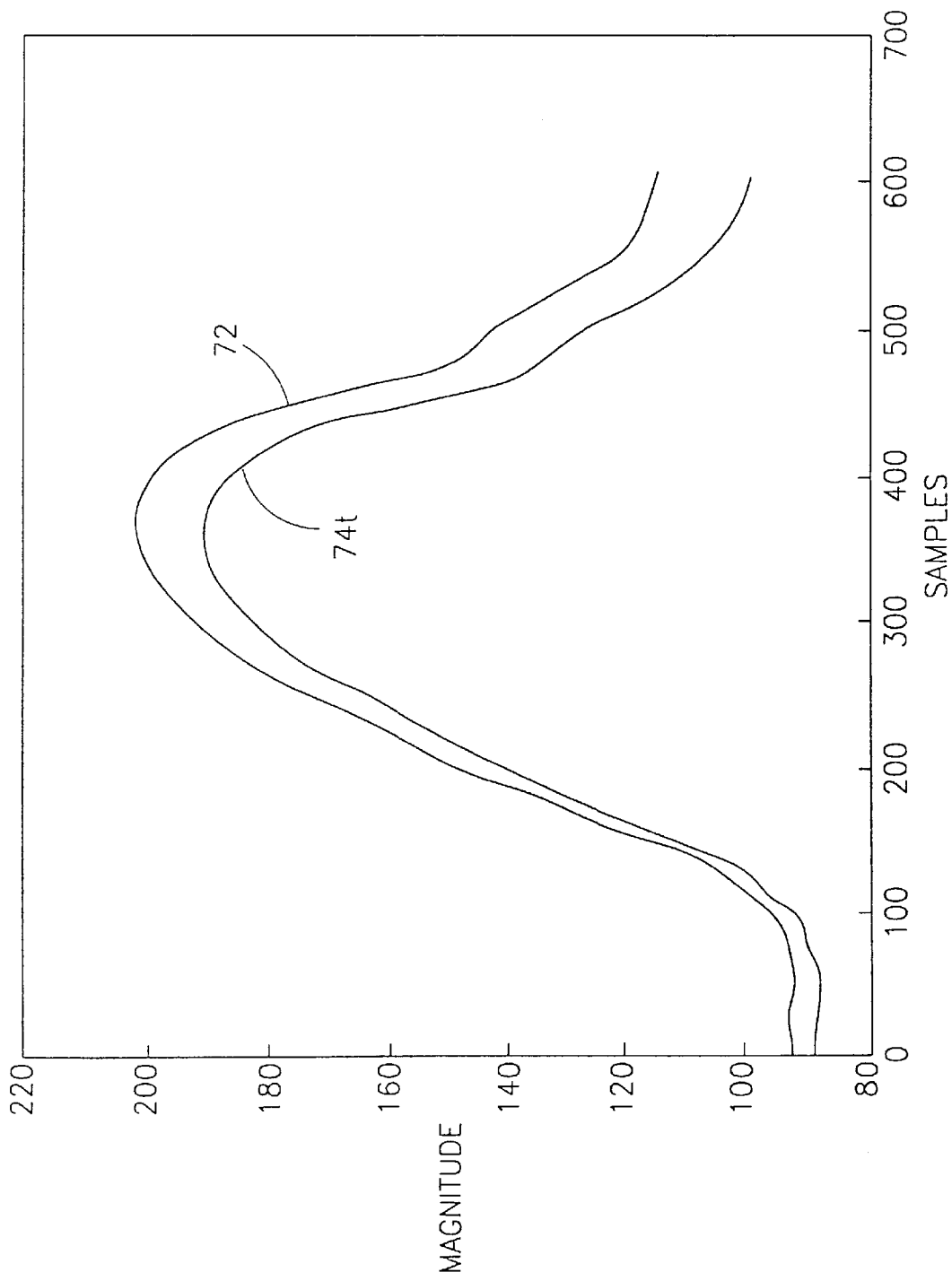
FIG. 19 presents the synchronized pressure signals representing the pressure proximal and distal to the stenosis.

The same time transformation (moving and stretching) is applied to the data measured by the fluid filled pressure transducer and Radi pressure wire. The results of this transformation are shown in FIGS. 18 and 19. FIG. 18 illustrates the measured fluid filled pressure, curve 71, and the transformed fluid filled pressure curve 73t. FIG. 19 describes the measured pressure at point A, curve 72, and the transformed pressure of point B, curve 74t.

The mean values, as measured by the fluid filled manometer when Radi pressure wire is at point A or B are different. The pressure measured at point B by Radi pressure wire is corrected according to the observed difference of the mean fluid filled pressure signals. The mean pressure correction turns the calculation of the hemodynamic parameters using a moving pressure transducer more accurate, because it allows to exclude changes in the aortic pressure between measurements at points A and B. Now, the pressure measured at point A and the corrected pressure at point B (curves 72 and 74t on FIG. 19) are used to calculate the non dimensional flow at rest. The mean value of the non dimensional flow is equal here to 1.8.

Figure 20:
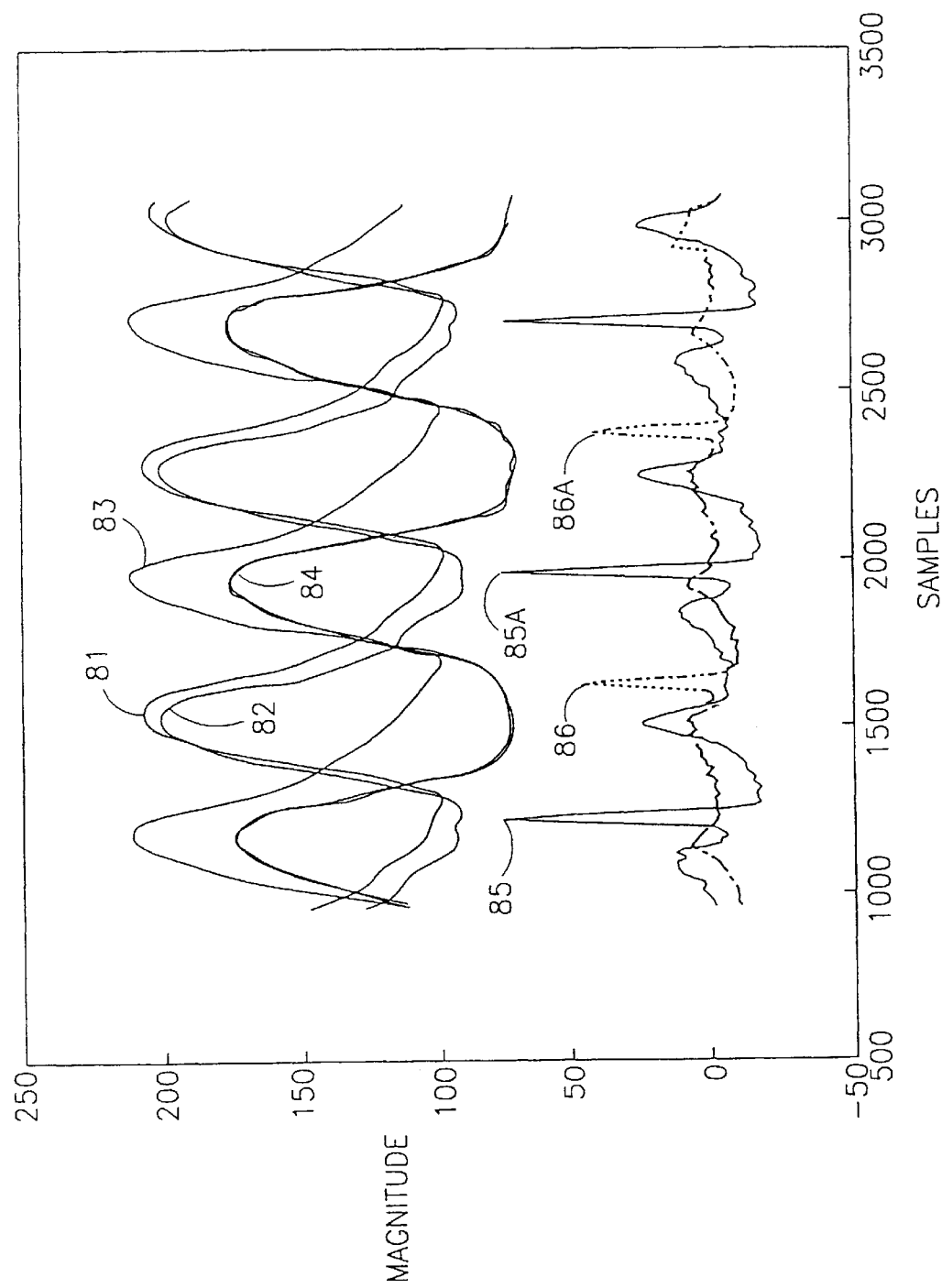
FIG. 20 presents ECG and pressure signals measured at point A during rest and at point B during vasodilatation state.

Reference is now made to FIG. 20, illustrating the pressure and ECG signals corresponding to vasodilatation condition. The pressure upstream the stenosis (point A) during vasodilatation, is assumed to be equal in rest and vasodilatation conditions. Curve 81 is the fluid filled pressure and Curve 82 is the Radi pressure, measured when Radi pressure sensor 91 is at point A and during rest. Curve 83 is the fluid filled pressure and Curve 84 is the sensor 91 pressure, both measured when Radi pressure wire is at point B and during vasodilatation. Curve 85 is the ECG signal measured when Radi pressure wire is at point A, at rest. Curve 86 is the ECG signal measured when Radi pressure wire is at point B, during vasodilatation.

Figure 21:
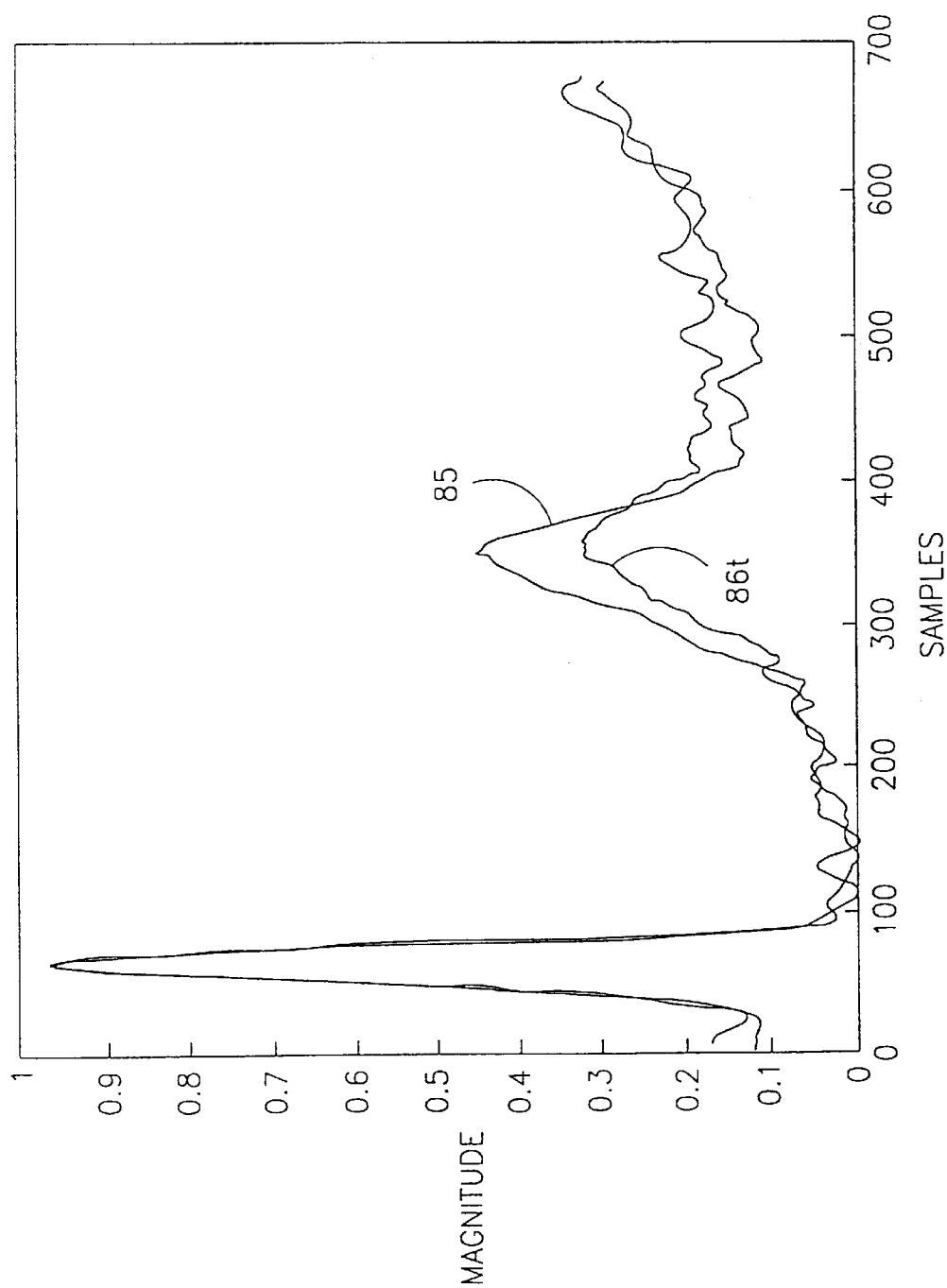
FIG. 21 presents ECG signals, at rest (point A) and during vasodilatation (point B), after synchronization, applying the transformation of Method 2.
Figure 22:
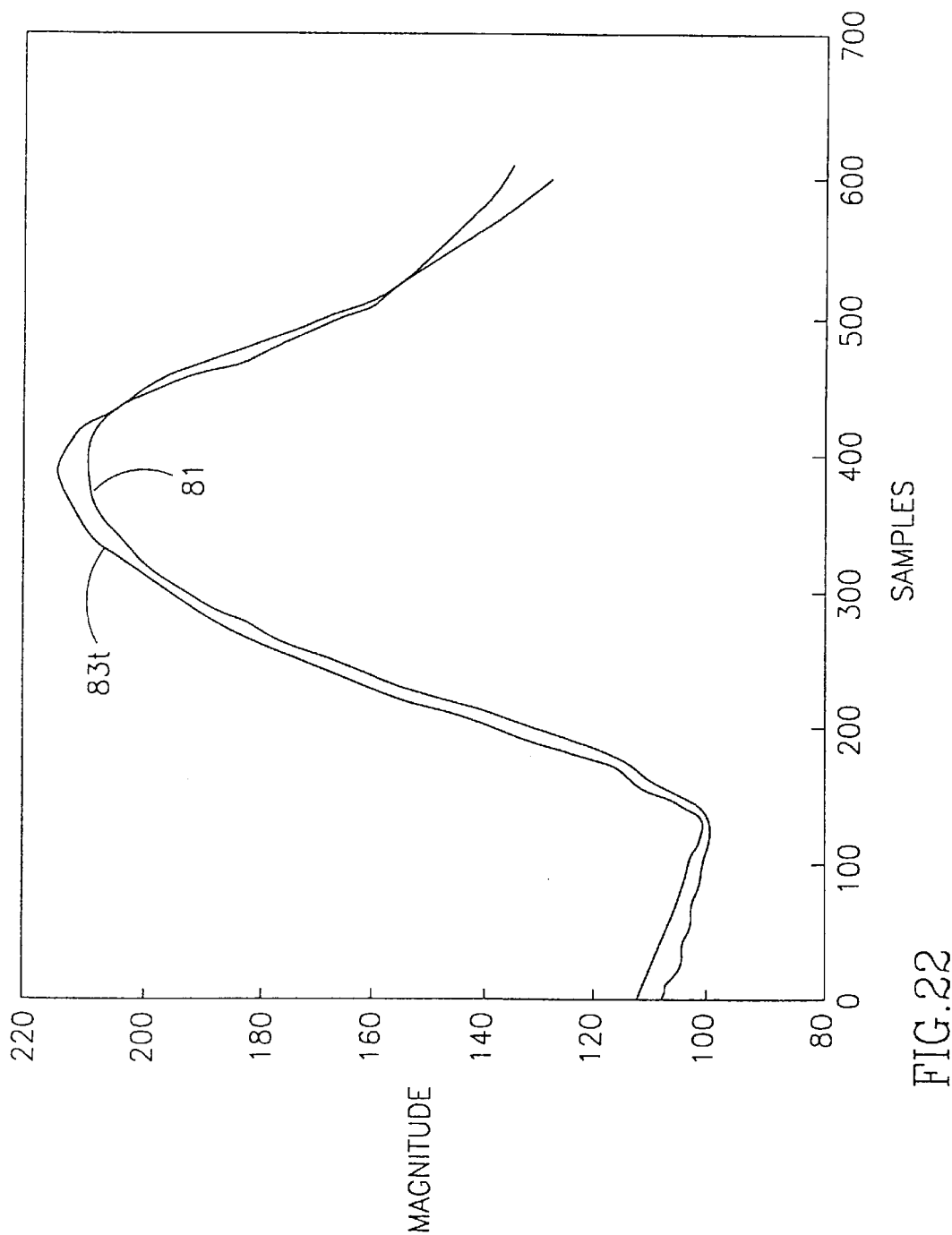
FIG. 22 presents the fluid filled catheter pressure signals, at rest (point A) and during vasodilatation (point B), after synchronization of the pulses.
Figure 23:
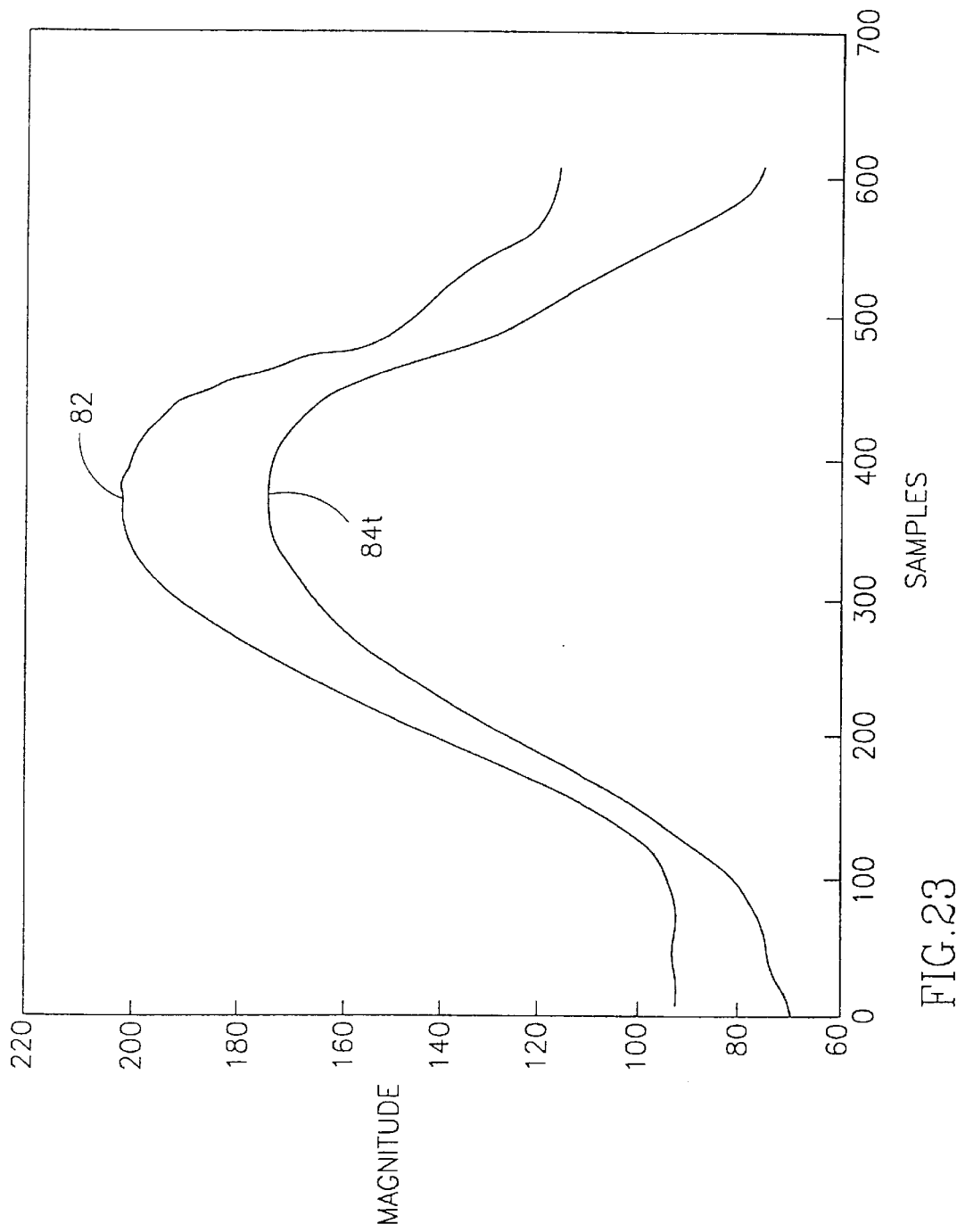
FIG. 23 presents the guide wire pressure signals, at rest (point A) and during vasodilatation (point B), after synchronization of the pulses.

The time transformation (moving and stretching) described herein above, is applied to the ECG measurements performed when Radi pressure wire is at point A at rest, and at point B during vasodilatation. The moved and stretched ECG signal (curve 86t) and the ECG signal 85 are shown in FIG. 21. The above analysis for data during vasodilatation is applied. The results of the transformation are shown in FIGS. 22 and 23. FIG. 22 illustrates the measured fluid filled pressure curve (81) and also the transformed fluid filled pressure curve (83t). FIG. 23 describes the measured pressure curve at point A (82) and the transformed pressure curve of point B (84t). The mean value of the non dimensional flow during vasodilatation is 2.8. Now the parameters of interest are calculated.

FFR is calculated using the mean value of pressure measured at point A and the mean value of corrected pressure measured at point B, both during vasodilatation (shown in FIG. 23), resulting in FFR=0.85. The suggested method of FFR calculation is more accurate then the standard method due to the fact that pressure data at point A is used instead of pressure data measured by fluid filled manometer.

CFR is calculated as the ratio of the non dimensional flows during vasodilatation and rest: CFR=2.8/1.8=1.55.

Figure 25:
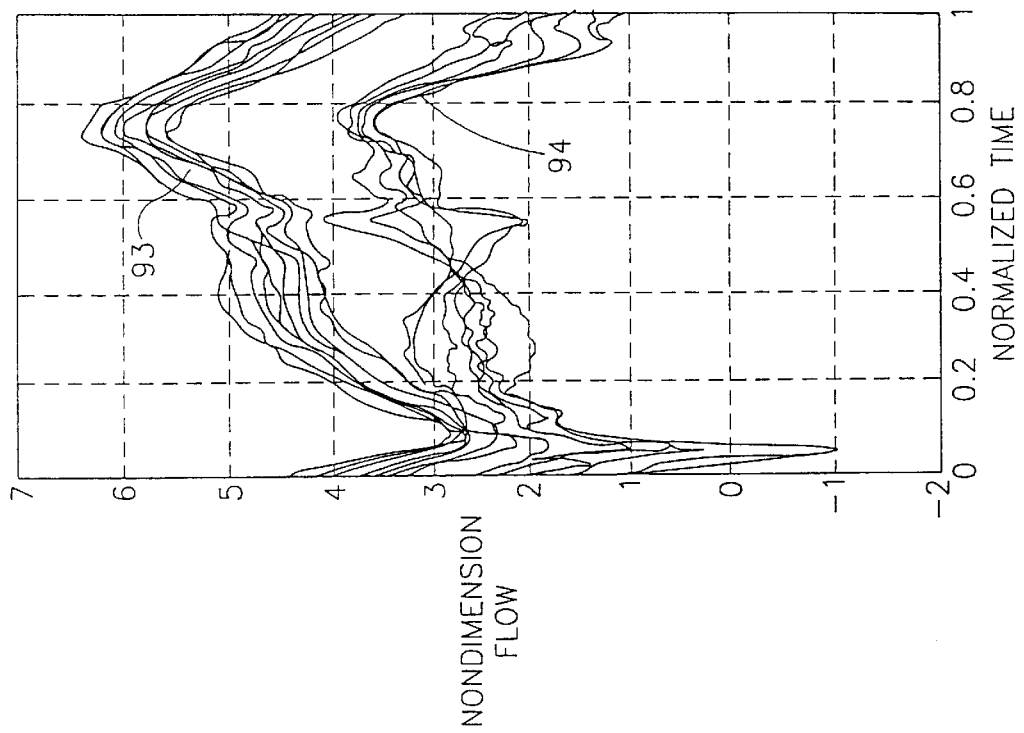
FIG. 25 presents the calculated values of the non-dimensional flow using the data shown in FIG. 24.
Figure 24:
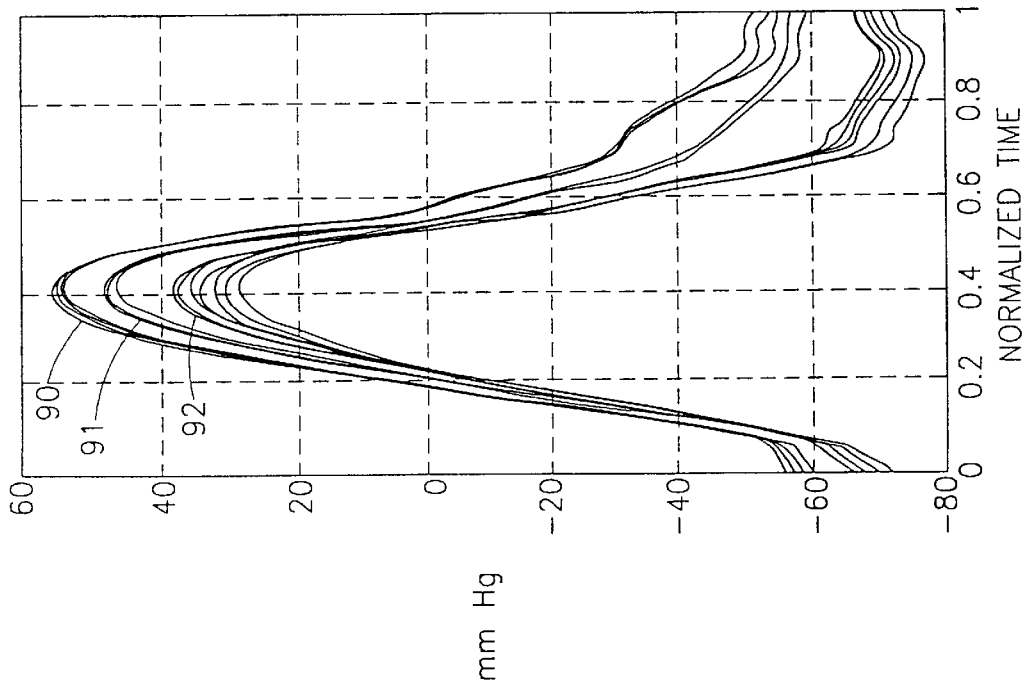
FIG. 24 presents the distribution of a set of synchronized and transformed pressure signals measured at rest and during vasodilatation, used for determining mean values of hemodynamic coefficients.

The procedure as described above, may be applied to a set of heartbeats. FIG. 24 illustrates synthesized and transformed pressure data at point A during rest (curves set 90), at point B during rest (curves set 91) and at point B during vasodilatation (curves set 92). FIG. 25 illustrates the derived non-dimensional flow during rest (curves set 94) and during vasodilatation (curves set 93).

Figure 26:
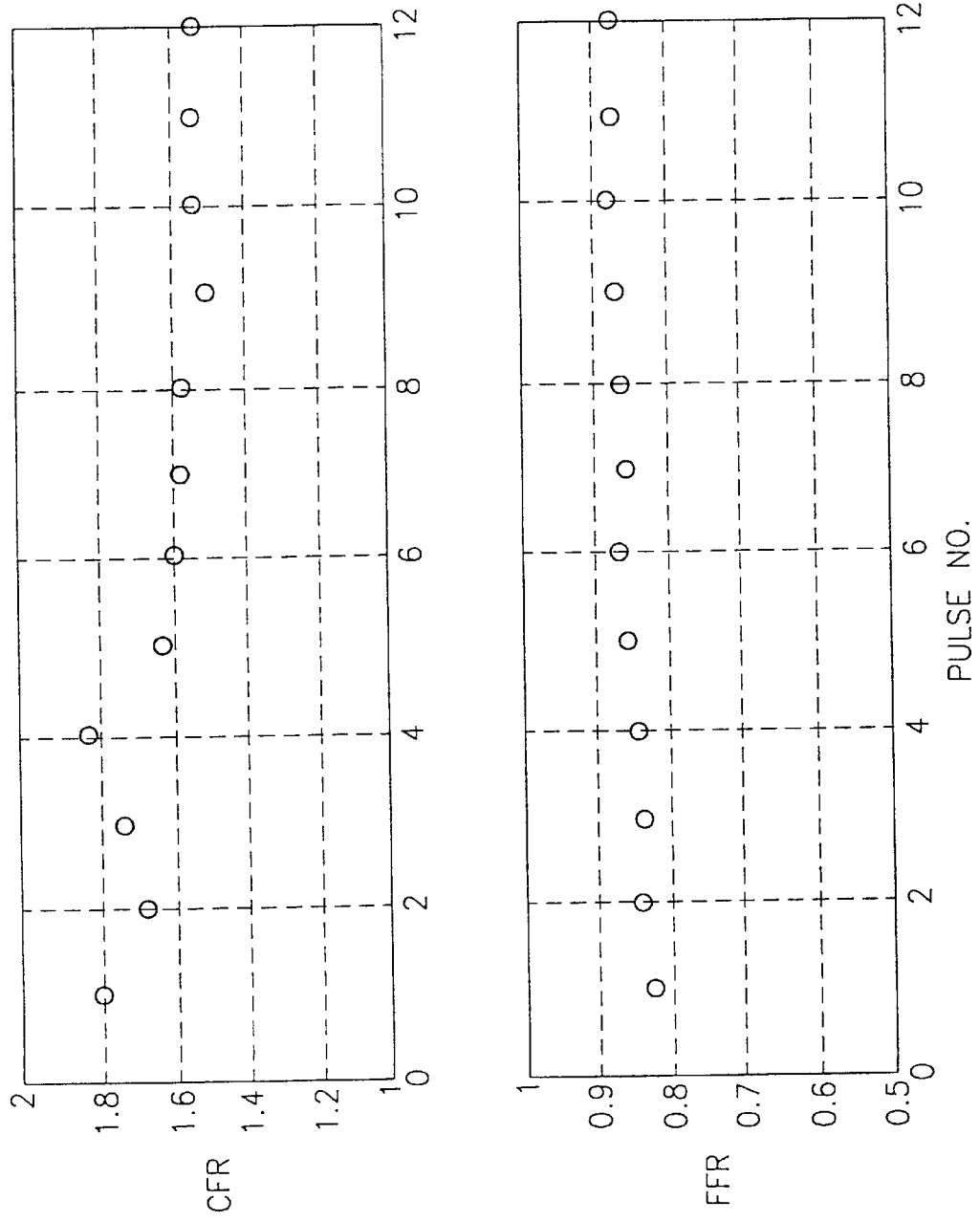
FIG. 26 presents the calculated values of CFR and FFR for each pulse.
Figure 28:
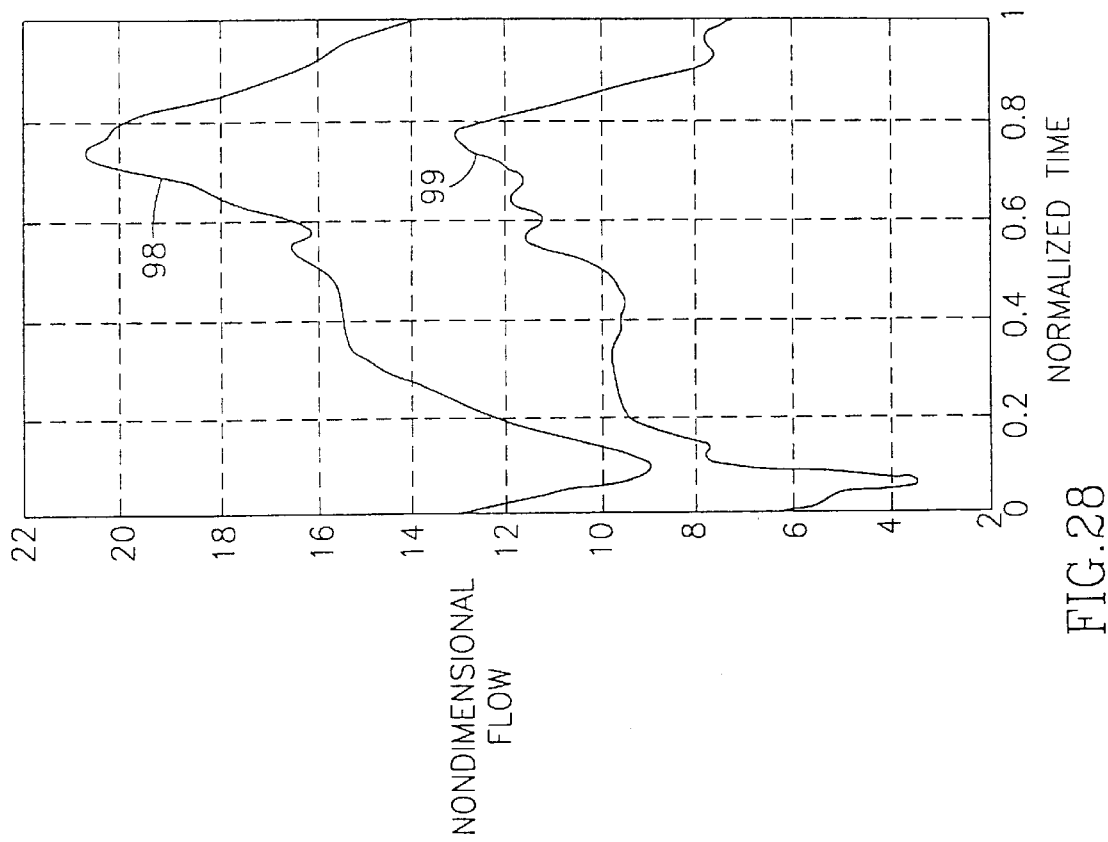
FIG. 28 presents the calculated values of the non-dimensional flow using the data described in FIG. 27.
Figure 27:
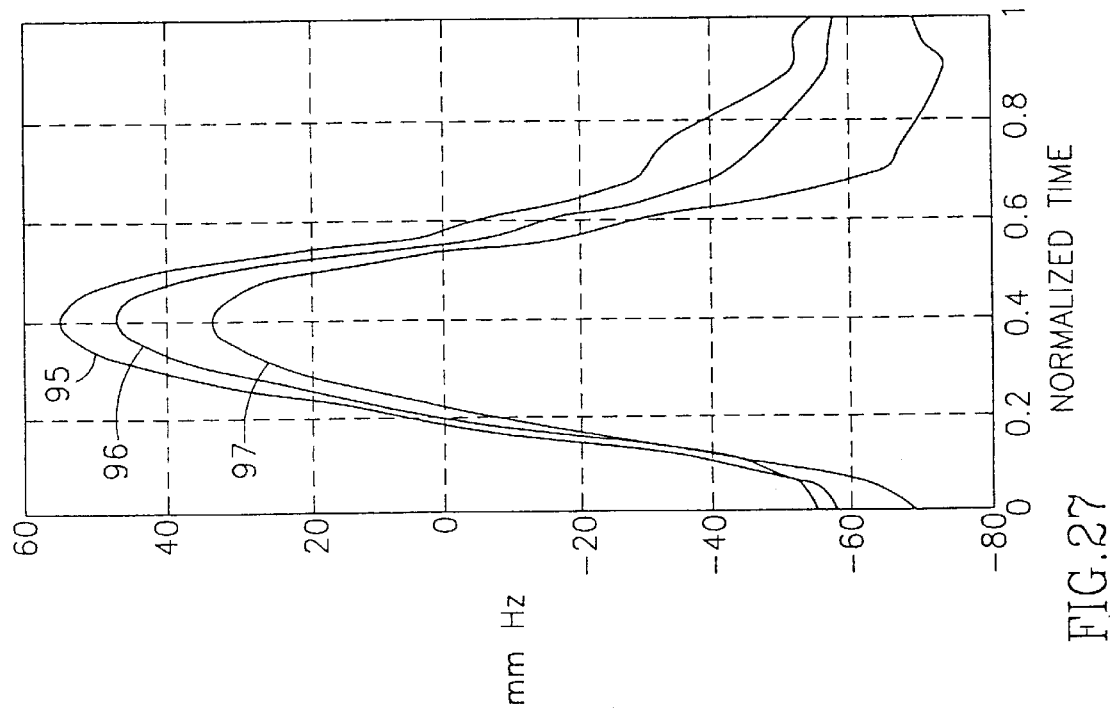
FIG. 27 presents the mean values over number of heartbeats of pressure at point A and point B at rest and vasodilatation conditions.

CFR and FFR values as calculated for each pulse are shown in FIG. 26. The mean value of CFR is 1.63, and the mean value of FFR is 0.85. A different analysis approach is to calculate the mean value of pressure (over multiple heartbeats), for every normalized (non dimensional) time. FIG. 27 presents the pressure mean value at points A and B during rest (curves 95 and 96), and pressure at point B during vasodilation (curve 97). Non-dimensional flow is calculated using these mean values, shown in FIG. 28. Curve 98 is the calculated non dimensional flow during vasodilatation. Curve 99 is the non dimensional flow during rest.

CFR and FFR calculated this way are CFR=1.61 and FFR=0.87. These values are highly correlated to the values received above. The data as shown in FIG. 27 enables estimation of the third parameter mentioned above. The diastole to systole velocity ratio (DSVR). In this case DSVR=1.3.

The parameters of interest were calculated for the same set of raw data using other methods proposed herein: Using Method 2, Optimal Overlap Method: CFR=1.92, FFR=0.78. Using Method 5, synchronization by max pressure signal:

CFR=1.46, FFR=0.81, DSVR=1.15

CLINICAL TEST EXAMPLE 2

This example demonstrates the use of pressure data for CFR and FFR calculation using Method 4, ECG based signal synchronization. The data includes blood flow measurements using the Flow wire by Endosonics, enabling the validation of the pressure based methods presented in this patent for derivation of CFR, FFR and DSVR. It is shown that highly correlated values were derived for these parameters, using both methods.
DATA ACQUISITION The example is based on human pressure data measured in the LAD artery, using a standard fluid filled pressure transducer, Radi pressure wire by Radi Medical Systems AB, Uppsala, Sweden and doppler flow wire by Endosonics. Data of ECG, pressures measured by Radi guide wire and fluid filled manometer were recorded and printed simultaneously. These data were scanned and digitized for computerized analysis. Some fragments of the digitized pressure and ECG curves, are shown in FIG. 29. The graph designated 106 describes pressure and ECG curves measured at rest while the Radi pressure sensor is located proximal to the stenosis (point A).

Figure 30:
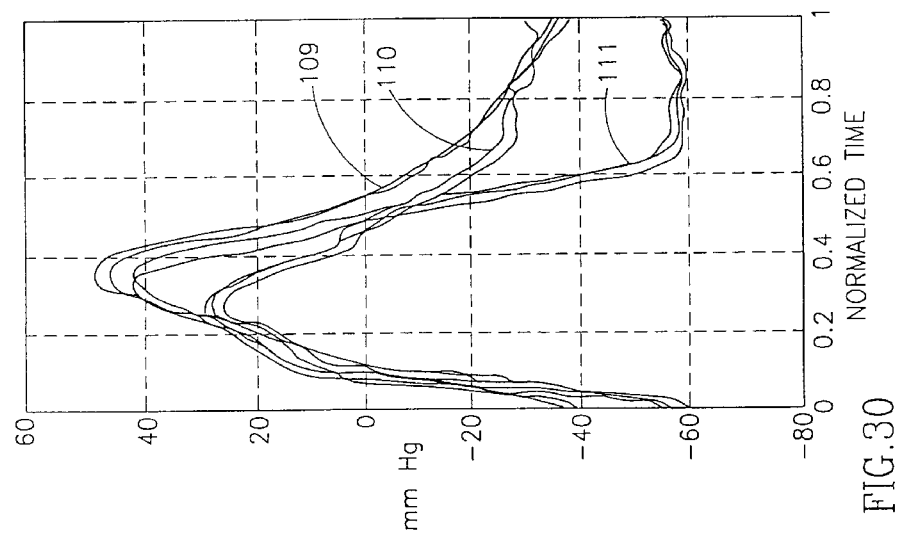
FIG. 30 presents synchronized pressure signals during rest and vasodilatation.

The graph designated 107 describes pressure and ECG curves measured at rest while the Radi pressure sensor is located distal to the stenosis (point B). The graph designated 108 describes pressure and ECG curves measured during vasodilatation while the Radi pressure sensor is located distal to the stenosis (point B). Curve 101 in graphs 106, 107, 108 illustrates the fluid filled manometer measurement. Curve 102 in graphs 106, 107, 108 illustrates the pressure measurement measured by the Radi pressure sensor. Curve 103 in graphs 106, 107, 108 illustrate the ECG measurement. Note that only the main peak of the ECG signal was digitized. These data were used for CFR calculation.
DATA ANALYSIS Method 4 was applied to calculate CFR. Results of calculations are shown in FIGS. 30, 31, 32, 33. Reference is now made to FIG. 30, which illustrates three sets of pressure signals after ECG synchronization 1. Curves set 109 is the pressure signals measured at rest and proximal to the stenosis (point A) 2. Curves set 110 is the pressure signals measured at rest and distal to the stenosis (point B) 3. Curves set 111 is the pressure signals measured during vasodilatation and distal to the stenosis (point B)

Figure 32:
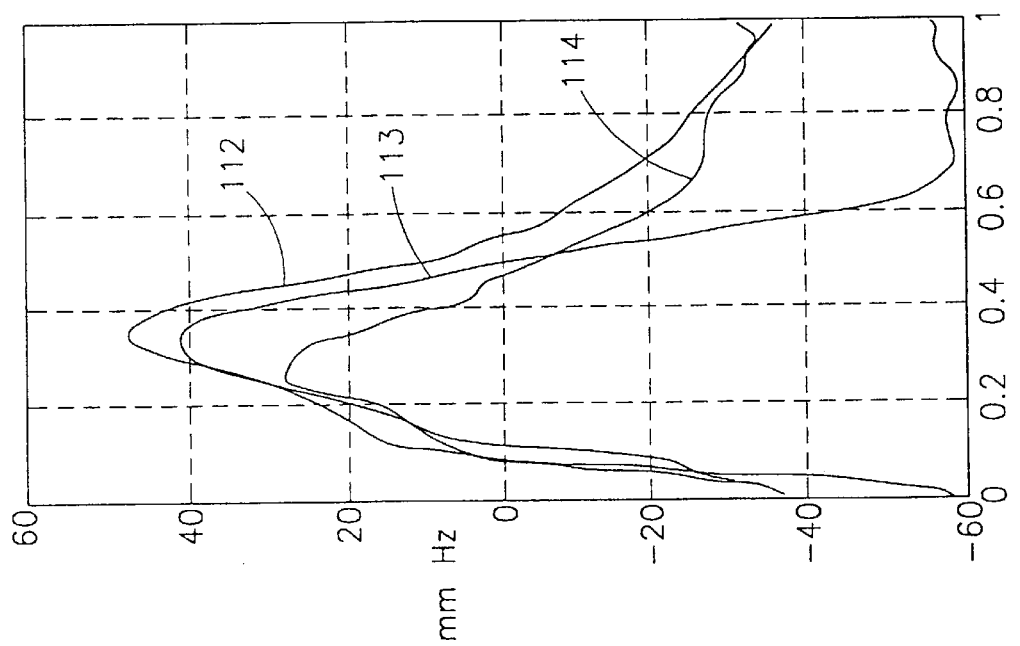
FIG. 32 presents the mean values of the synchronized pressure signals shown in FIG. 30.

FIG. 32 illustrates the mean values of each set of the pressure curves shown in FIG. 30, where Curve 112 is the mean value of the pressure signals measured at rest proximal to the stenosis (point A), Curve 113 is the mean value of the pressure signals measured at rest distal to the stenosis (point B), and Curve 114 is the mean value of the pressure signals measured during vasodilatation distal to the stenosis (point B).

Figure 31:
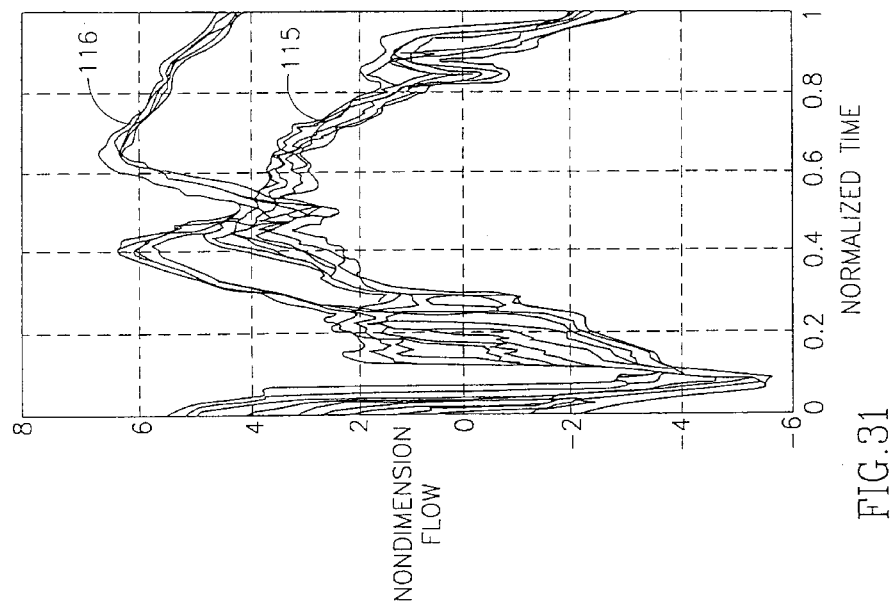
FIG. 31 presents non-dimensional flow curves calculated from the synchronized curves of FIG. 30.

FIG. 31 illustrates the non dimensional flow curves calculated from the curves of FIG. 30. The set of curves 115 describe the non dimensional flow during rest. The set of curves 116 describe the non dimensional flow during vasodilatation.

Figure 33:
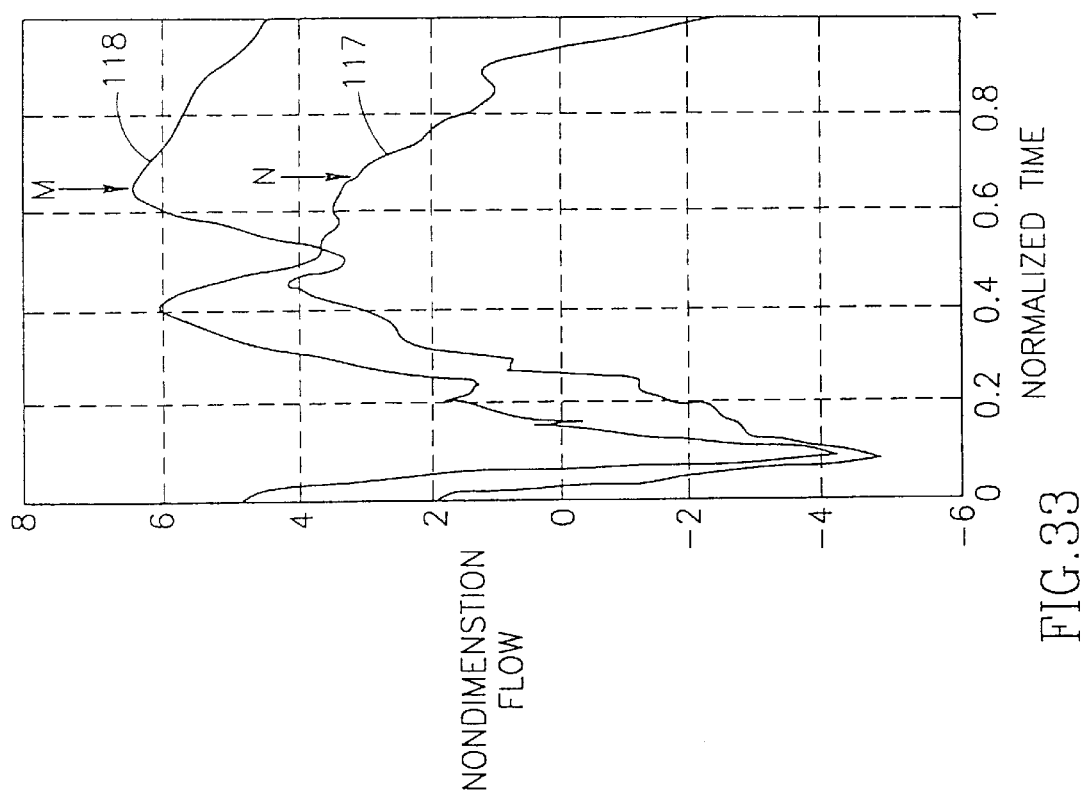
FIG. 33 presents the calculated mean non-dimensional flow used to determine hemodynamic parameters.

FIG. 33 describes the calculated mean non dimensional flow, where Curve 117 is the mean non dimensional flow at rest, and Curve 118 is the mean non dimensional flow during vasodilatation.

From FIG. 31 one may see, a major dispersion of the calculated flow during systole. Flow calculated for various heartbeats during diastole is consistent. The mean value of CFR (averaged over all heartbeats) is CFRm=1.56. The mean value of FFR (averaged over all heartbeats) is FFRm=0.79. In practice, CFR is usually determined as a ratio of the peak distal velocities. In this case, the ratio of the flow at points M and N as marked in FIG. 32 is CFRv=1.86. Using the blood flow measurements during rest and during vasodilatation, CFR and FFR are calculated: CFR=1.8 and FFR=0.75 The results using pressure measurements or flow rate measurements are highly correlated.
METHOD 4A: PULLBACK PRESSURE MEASUREMENTS WITH ECG SIGNALS SYNCHRONIZATION Reference is now made to FIG. 12, illustrating a cross section of an artery 30 having an arterial wall 32 and a stenosis 34. Two points A and B upstream and downstream of the stenosis define a section of the artery. The hemodynamic parameters: CFR, DSVR, and FFR along the section are of interest. A guiding catheter 3 (or diagnostic catheter) is inserted into the blood vessel of interest. An external fluid filled pressure transducer 31 is connected to the guiding catherter entrance (proximal end) measuring the pressure at point C (fluid filled pressure). A guiding wire 6 having a pressure sensor at its tip 4 is inserted through the guiding catheter and positioned so that the pressure sensor 4 is located at point A downstream of the stenosis. Both pressure sensors 4 and 31 are connected to the system 23 described in FIG. 1, 1.a, 1.b., 2, and 2.a. Simultaneous ECG data is collected using standard instrumentation available at all times in all catheterization procedures.

DATA ACQUISITION

The following steps are performed to obtain the required data:

Step 1: Simultaneous pressure and ECG measurements are performed. The pressure transducer 4 is at point B. Data of pressure versus time $P_{RSt}$) and $P_{RC(t)}$ and ECG are acquired, while the patient is at rest condition.

Step 2: Induce vasodilation.

Step 3: Simultaneous measurements of pressure and ECG are repeated, yielding data of pressure verses time $P_{RS(t)}$ and $P_{RC(t)}$ and ECG. The measurements are performed while the patient is at vasolidation condition.

Step 4: Pullback the pressure transducer 4 to point A.

Step 5: Simultaneous measurement of ECG and pressure is repeated, yielding data of pressure versus time $P_{VA(t)}$ and $P_{VC(t)}$, and ECG.

DATA ANALYSIS

To calculate hemodynamic parameters, simultaneous pressure at points A and B at rest and during vasolidation are required. The pressures at points A and B during rest and vasolidation are measured but non-simultaneously. Time synchronization is performed using the method that ECG signals are stable while measuring pressure points at A or B. Therefore, synchronization of the ECG signals results in synchronization of the pressure signals at points A and B. Synchronization is achieved by applying the method relating to Method 2, with the Ecg signals used instead of the fluid filled pressure signals. For the vasolidation condition, it is possible to measure pressure only at point B (downstream) since $P_{VA}=P_{RA}$. Then, the parameters CFR, DSVR, and FFR are derived using the equations mentions hereinabove. This method is more robust to changes in pressure accuracy due to drifting effects as the proximal and distal pressure measurements are taken in a short time.

METHOD 5: SYNCHRONIZATION BY MAX. PRESSURE SIGNAL CLINICAL SYSTEM

Figure 34:
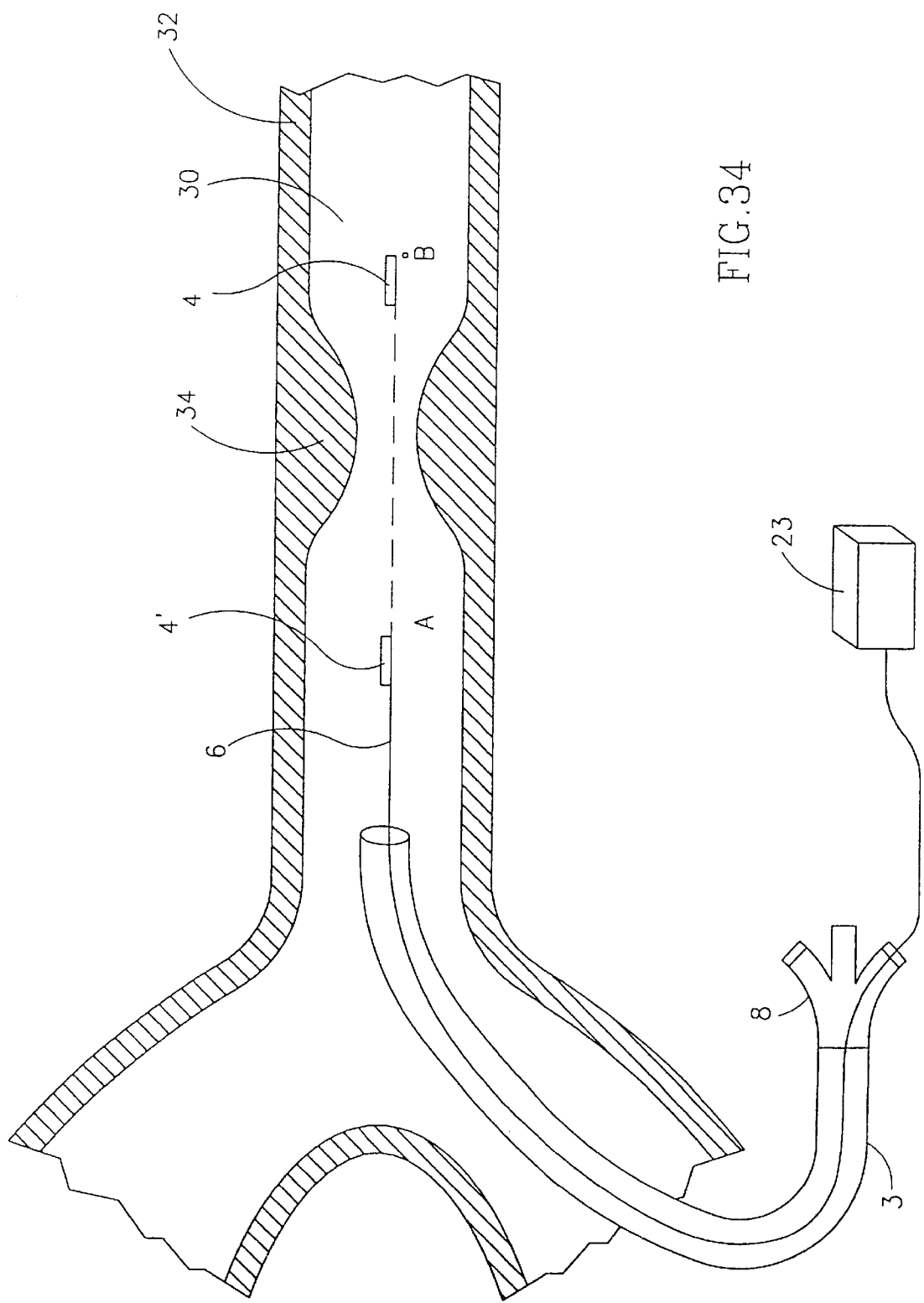
FIG. 34 illustrates the positioning of the pressure sensors and measurements location when using the method of synchronization by max. pressure signal.

Reference is now made to FIG. 34, illustrating a cross section of an artery 30 having an arterial wall 32 and a stenosis 34. The points A and B, proximal and distal to the stenosis, define a section of the artery. The parameters CFR, FFR, and DSVR of this section are of interest. A guiding catheter 3 (or diagnostic catheter, or any other hollowed catheter) is inserted into the blood vessel of interest. The guide wire 6, having a pressure sensor at its tip 4, is inserted trough the guiding catheter and positioned so that the pressure sensor 4 is located at point A, proximal to the stenosis. The pressure sensor 4 is connected to the system 23 described in FIGS. 1,1.a and 2,2.a.

DATA ACQUISITION

The following steps are performed to obtain the required data:

Step 1: Measurement of pressure is performed by the pressure sensor 4, yielding $Pr_A(t)$. The measurement is performed while the patient is at rest condition.

Step 2: The pressure sensor 4 is moved upstream to point B, distal to stenosis.

Step 3: Measurement of pressure is performed by the pressure sensor 4, yielding $Pr_B(t)$.

Step 4: Induce vasodilatation.

Step 5: Measurement of pressure is performed by the pressure sensor 4, yielding $Pv_B(t)$. The measurement is performed during vasodilatation.

Step 6(optional): Pressure sensor 4 is moved backward to point A, proximal to the stenosis, yielding $Pv_A(t)$. This step is optional. The alternative is to rely on the assumption that the pressure at point A during vasodilatation is equal to the pressure at point A during rest.

DATA ANALYSIS

Optimal Overlap method is used to synchronize the pressure pulses measured at points A and B. Synchronization is achieved by moving the pressure signal measured at point B, so that its maximum value fits the maximum value of the other pressure signal (measured at point A). Now, simultaneous pressure data, proximal and distal to the stenosis, are available, and the hemodynamic parameters are calculated. Using the human test data described in Example 1 of Method 4 the following values are calculated:

CFR=1.46

FFR=0.81

DSVR=1.15

METHOD 6: INFLATED BALLOON $CFR_0$ CALCULATIONS

A method is described for the determination of the hemodynamic parameters in a non-obstructed vessel, using a standard balloon, inserted into the blood vessel of interest. Inflating the balloon induces an artificial obstruction. The inflated balloon should not significantly impede the flow. However, a minimal pressure gradient of about 4 mmHg in rest is required. Pressures across the induced stenosis are obtained, and calculated of the hemodynamic. Parameters are performed using one of the methods mentioned herein above. The $CFR_0$ is then calculated according to the equations described herein above.

Figure 35:
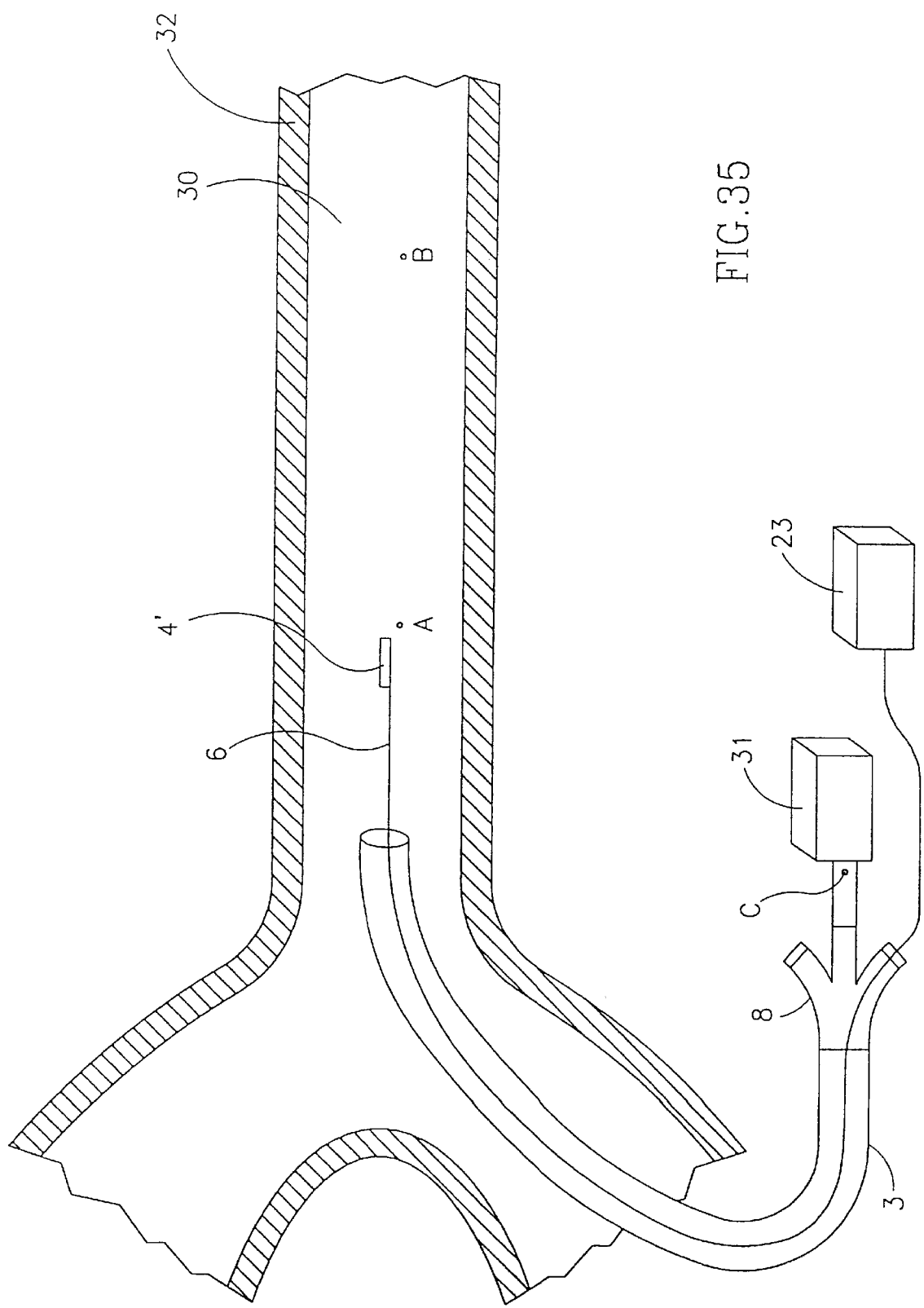
FIG. 35 illustrates the pressure measurement points inside a non-lesioned blood vessel.

Reference is now made to FIG. 35, illustrating a cross section of an artery 30 having an arterial wall 32. The points A and B, define a non-lesioned section of the artery. The parameter $CFR_0$, of this section is of interest. A guiding catheter 3 (or diagnostic catheter, or any other hollowed catheter) is inserted into the blood vessel of interest. An external fluid filled pressure transducer 31 is connected to the guiding catheter ostium (proximal end) measuring the pressure at point C (fluid filled pressure).

A guide wire 6, having a pressure sensor 4 at its tip, is inserted through the guiding catheter and positioned so that the pressure sensor 4 is located at point A. Pressure sensor 4 is connected to system 23 described in FIGS. 1,1.a and 2,2.a. A balloon catheter is then inserted into the blood vessel of interest 30 (not shown).

DATA ACQUISITION

The following steps are performed to obtain the required data:

Step 1: Simultaneous measurement of pressure is performed by the pressure sensors 4 and 31, yielding $Pr_A(t)$ and $Pr_C(t)$. The measurements are performed while the patient is at rest condition.

Figure 36:
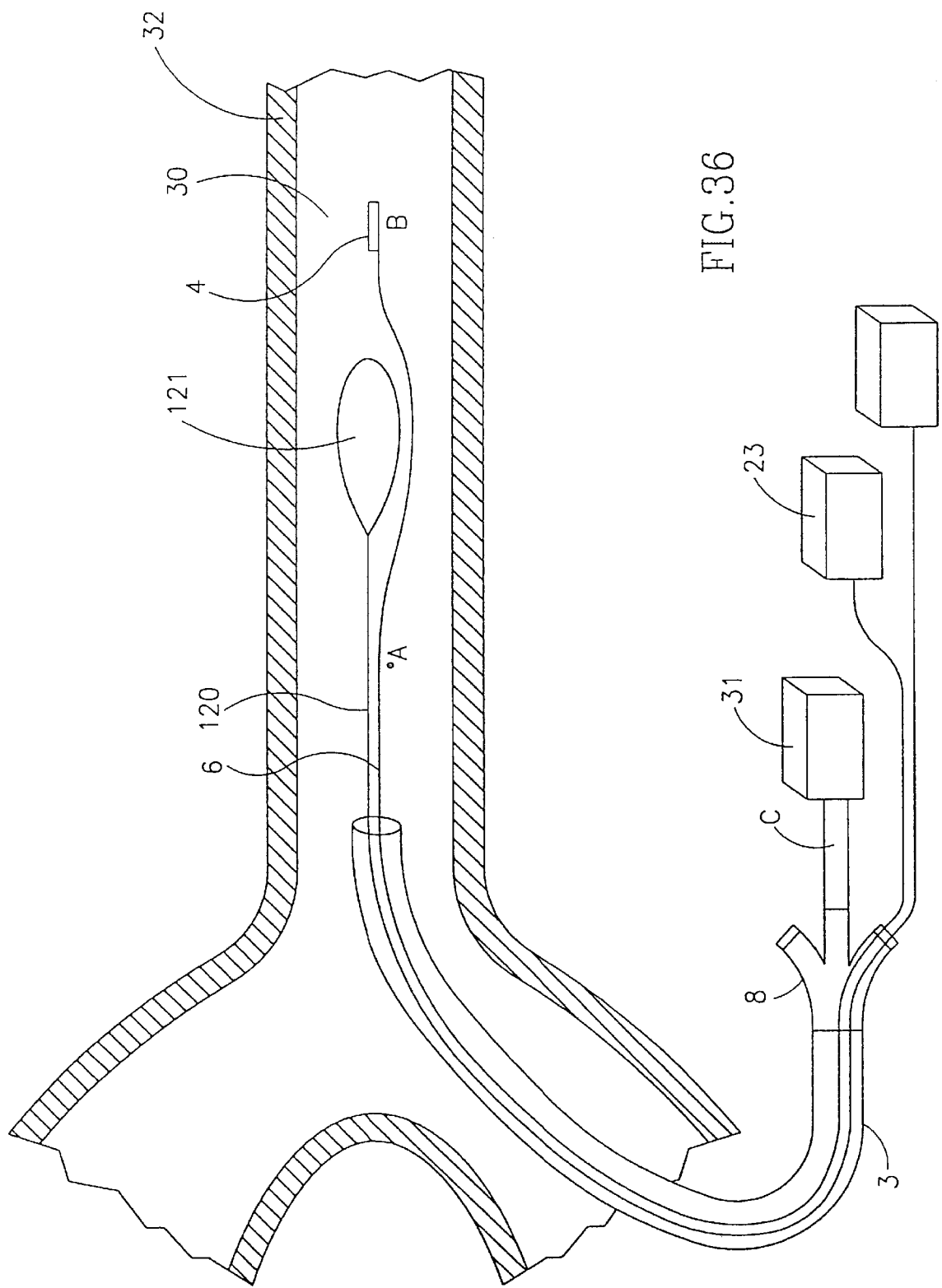
FIG. 36 illustrates a balloon artificial obstruction inside a non-lesioned blood vessel and pressure measurement distal to the balloon.

Step 2: Reference is made to FIG. 36. The pressure sensor 4 is moved to point B. The balloon catheter 120 is inserted into the blood vessel 30 and positioned so that the balloon is located between points A and B. At this stage the balloon 121 is inflated.

Step 3: Simultaneous measurement of pressure is performed by the pressure sensors 4 and 31, yielding $Pr_B(t)$ and $Pr_C(t)$.

Step 4: Induce vasodilatation.

Step 5: Simultaneous measurement of pressure is performed by pressure sensors 4 and 31, yielding $Pv_B(t)$ and $Pv_C(t)$. The measurement are performed during vasodilatation condition.

DATA ANALYSIS

CFR and FFR are calculated for the balloon obstructed vessel using the procedure described in Method 2. However, all other methods (mentioned herein above) of clinical system for pressure measurements and calculation can be used together with balloon artificial obstruction.

After CFR and FFR (for the balloon obstruction) are calculated, the mean values of the pressure gradient during rest ($P_A rest - P_B rest$) and during vasodilatation ($P_A rest - P_B vaso$) are calculated. Then $CFR_0$, for the vessel without the obstruction, is calculated using the equation mentioned herein above.

METHOD 7: CFD MODELING OF THE FLOW IN THE CORONARY ARTERY WITH STENOSIS. CFR AND FFR PARAMETERS.

Medical specialist estimate stenosis severity using either simple geometrical parameters, such as percent diameter stenosis, or hemodynamically based parameters such as the fractional flow reserve (FFR) or coronary flow reserve (CFR). As shown herein, the relationship between actual hemodynamic conditions and the above mentioned parameters of stenosis severity are established. A numerical model of the blood flow in a vessel is used with a blunt stenosis and autoregulated vascular bed to simulate a stenosed blood vessel. A key point to realistic simulations is to model properly the arterial autoregulation. The present numerical model is based on the comparison 0.1' the flow in healthy and stenotic vessels. The calculated values of CFR and FFR are in the physiological range.

Results. The hemodynamic conditions of a healthy artery may be characterized by CFRo and the vascular bed index VBlo, where the index 0 refers to healthy vessels. The new parameter VBlo, that is introduced in the present study, is equal to the ratio of mean shear to mean pressure. Instead of conducting hard to perform in-vivo experiments, in the first stage of the study a numerical model of the blood flow in a vessel with a blunt stenosis and autoregulated vascular bed is used. The exact autoregulation mechanism is unknown. Therefore, two different possible autoregulation conditions were tested: (i) constant wall shear stress and (ii) constant flow. The model is based on the comparison of flow in healthy and stenotic vessels.

Conclusions. Based on the results, the constant flow model of vascular bed autoregulation suggested in the present study allows using CFD to analyze different situations in clinical practice in an attempt to correlate between common hemodynamic parameters and the severity of stenosis.

EXAMPLE 1

In-vivo CFR-FFR Measurements in Human Subjects

Figure 44:
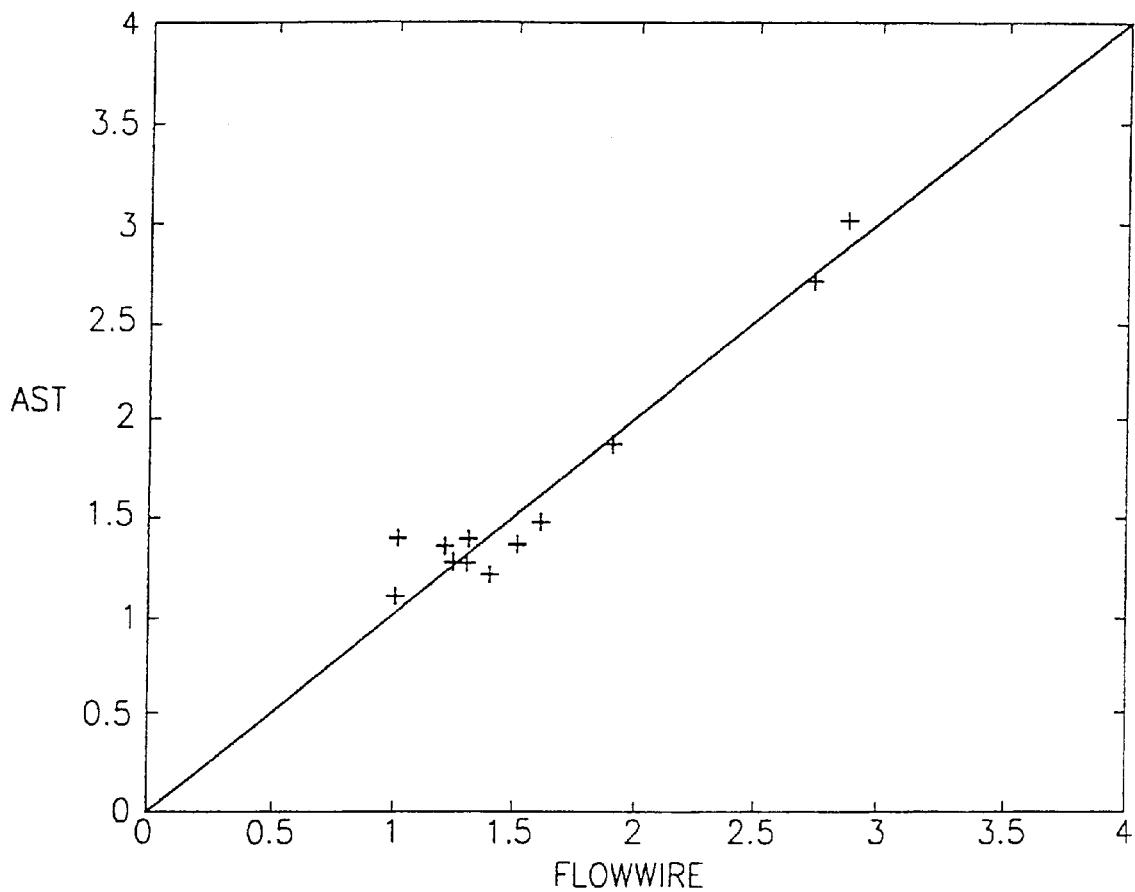
FIG. 44 In-vivo human data of CFR-AST which uses the Automatic Similar Transformation method.

Studies on human patients were conducted provided the results set forth in FIG. 44 and Tables 2–5. The system provided herein which includes the Automatic Similar Transformation method was connected to a Siemens Cathcor cathlab monitor for acquisition of the aortirial pressure wave, the Radi pressure wave and the ECG. The ECG signal output included a triggering signal which processed ECG. The system included pressure wires and pressure wire interface box and a fluoroscopy system. The velocity signal was directly sampled and used the analogous output of the Endosonics FlowMap system and flow wires.

Protocol: The patients studied with single lesion, double lesions, intermediate lesions. All the patients were symptomatic. CFR/FFR were measured using the pressure wires and flow wire simultaneously. Data analysis for comparison of pressure based and velocity based CFR estimation was done off-line.

TABLE 2

D.H.-.RCA 80–90% stenosis.

| File | CFR | FFR | BPG | HPG | Comment |
|---|---|---|---|---|---|
| 10_56_36 | 1.07 | 0.41 | 41.3 | 45.1 | Vaso 1 |
| 10_40_47 | 1.04 | 0.43 | 42 | 44 | Vaso 2 |
| | | | | | Full diast pulse at rest |
| 10_59_25 | 2.02 | 0.84 | 3.8 | 12.4 | After balloon |

TABLE 3

W.G. - CIRC 70–90% stenosis.

| File | CFR | FFR | BPG | HPG | Comment |
|---|---|---|---|---|---|
| 12_44_16 | 1.08 | 0.55 | 32.3 | 33.9 | Vaso 1 |
| 12_52_27 | 1.12 | 0.49 | 33.0 | 39.5 | Vaso 2 |
| 13_00_52 | 4.0 | 0.89 | 0.39 | 7.8 | After balloon - old proximal pressure |
| 13_00_52 | 3.0 | 0.87 | 1.3 | 10.1 | After balloon - new proximal pressure |

TABLE 4

T.I. - LAD 90% stenosis.

| File | CFR | FFR | BPG | HPG | Comment |
|---|---|---|---|---|---|
| 10_37_21 | 1.04 | 0.68 | 37.3 | 40.3 | Vaso 1 |
| 10_50_00 | 1.2 | 0.59 | 33.4 | 45.2 | Vaso 2 |
| 10_50_00 | 3.2 | 0.98 | −0.7 | 1.7 | After balloon |

TABLE 5

CLINIAL DATA REPORT: CFR AND FFR CALCULATIONS

| Patient | BPG | HPG | CFR-ATS METHOD | FFR | CFR FLOW # | FFR FLOW * |
|---|---|---|---|---|---|---|
| 1 | 68.4 | 79.9 | 1.08 | 0.36 | 1.1 | 1.1 |
| 2 | 9.7 | 32.6 | 1.87 | 0.66 | 1.9 | 1.9 |
| | 9.4 | 22.8 | 1.47 | 0.77 | 1.6 | 1.6 |

TABLE 5-continued

CLINIAL DATA REPORT: CFR AND FFR CALCULATIONS

| Patient | BPG | HPG | CFR-ATS METHOD | FFR | CFR FLOW # | FFR FLOW * |
|---|---|---|---|---|---|---|
| 3 | 1.4 | 26.2 | 2.7 | 0.75 | 2.6 | 2.72 |
|  | 1.5 | 37 | 3 | 0.66 | 1.5 | 2.85 |
|  | 1.6 | 38 | 3 | 0.66 | 1.7 | 2.6 |
| 4 | 18.5 | 27 | 1.22 | 0.65 | 1.6 | 1.6 |
|  | 19 | 30 | 1.3 | 0.6 | 1.0 | 1.0 |
|  | 18 | 32 | 1.36 | 0.58 | 1.2 | 1.2 |
|  | 18.4 | 33.5 | 1.4 | 0.56 | 1.1 | 1.1 |
| 5-Lesion 1 | 0.72 | 3.94 | 1.9 | 0.96 | 1.9 | 1.55 |
|  | 0.1 | 3.4 | 2.2 (1.65) | 0.97 | 2.1 | 1.51 |
|  | 0.73 | 0.85 | 1.6 (1.5) | 0.99 | 1.7 | 1.7 |
|  | 0.56 | 3.2 | 1.9 (1.4) | 0.97 | 1.7 | 1.7 |
| Lesions 1 | 6.4 | 12.7 | 1.3 | 0.87 | 1.6 | 1.6 |
| and 2 | 7.7 | 14.6 | 1.15 | 0.85 | 1.7 | 1.7 |
|  | 9.1 | 15 | 1.2 | 0.85 | 1.2 | 1.19 |
|  | 11.5 | 14.6 | 1.14 | 0.85 | 1.6 | 1.0 |
| 6 | 5 | 9.5 | 1.4 (1.2) | 0.8 | 1.3 | 1.3 |
|  | 4.5 | 8 | 1.4 (1.3) | 0.8 | 1.3 | 1.3 |

CFR#automatic CFR calculation by Endosonics

CFR * CFR calculated based on flow raw data.

BPG–$\Delta P_{rest}$, mean pressure gradient across stenosis at rest

HPG–$\Delta P_{vaso}$, mean pressure gradient across stenosis during vasolidation.

Results: The results demonstrate that good correlation was found between the CFR-Automatic Similar Transformation (AST) method for CFR/FFR estimation to the velocity based CFR estimation. In some case the CFR calculated based on velocity raw data actually resulted in a higher correlation, indicating problematic automatic CFR calculation of the Endosonics system. The vasodilatory effect was achieved by intracoronary Adenosine injection.

EXAMPLE 2

In-vivo CFR-FFR Measurements in Canines

Animal studies with 4 canines (20–25 Kg), were performed in a hospital in Japan. The in-vivo studies set up included: The Automatic Similar Transformation (AST) System connecting to a Nihon Kohden RM-6000 monitor for acquisition of the arterial pressure wave, a pressure signal, ECG and flow signal (fluoroscopy system which included a CardioMed CM2000 transit time and doppler flowmeter perivascular handle flowprobes (3 mm)). The flow signal was presented on the monitor screen and sampled by the System which includes the AST method. In these studies a FloWire was not used.

Protocol: The animal was anesthetized, the chest opened and the heart exposed. The LCX was then dissected to allow introduction of the perivascular flowprobe and the balloon occluder. The animal was catheterized via the carotid, and a pressure wire was introduced. Proximal and distal measurements were collected for each level of stenosis. Vasodilatation response was induced using IC Papaverine 4 mg. In the first two animals the vasodilatation dose for max hyperemic response was studied using a total occlusion technique. A series of occlusions was introduced by slowly inflating the balloon occluder, or by using a snare. In each level of occlusion the required measurements were obtained. At each level of stenosis, the percent stenosis was estimated from a rentgen picture.

Results: The animals used were very stable and in a good physiological condition throughout the procedure. The target vessel was the LCX, where a straight section with no branches was easier to find. 5–6 levels of stenosis were induced in each animal. The level of stenosis was estimated after each measurement by a Rentgen picture.

Figure 37:
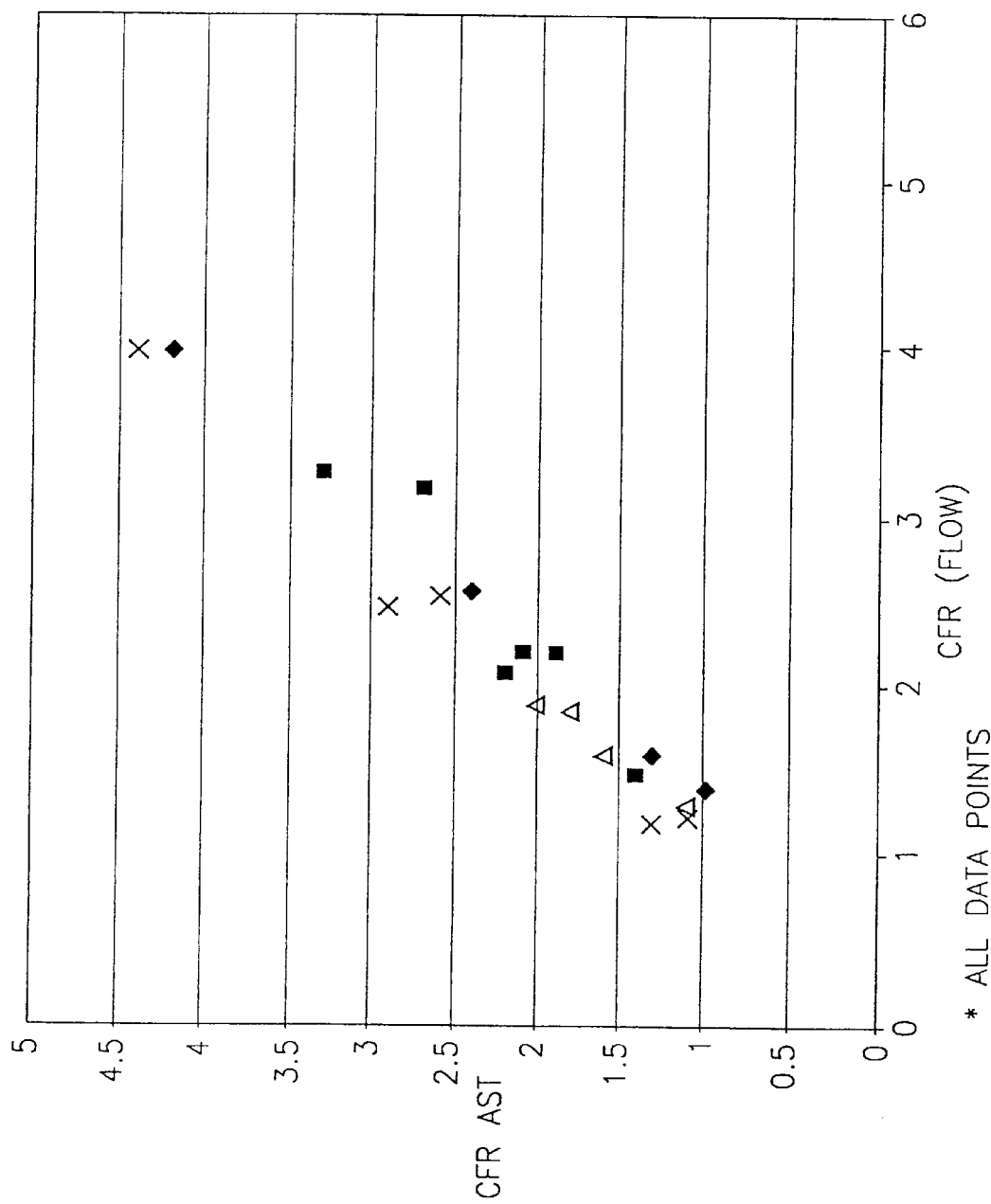
FIG. 37 In-vivo canine data of CFR –F which uses the Automatic Similar Transformation method and CFR flow.
Figure 38:
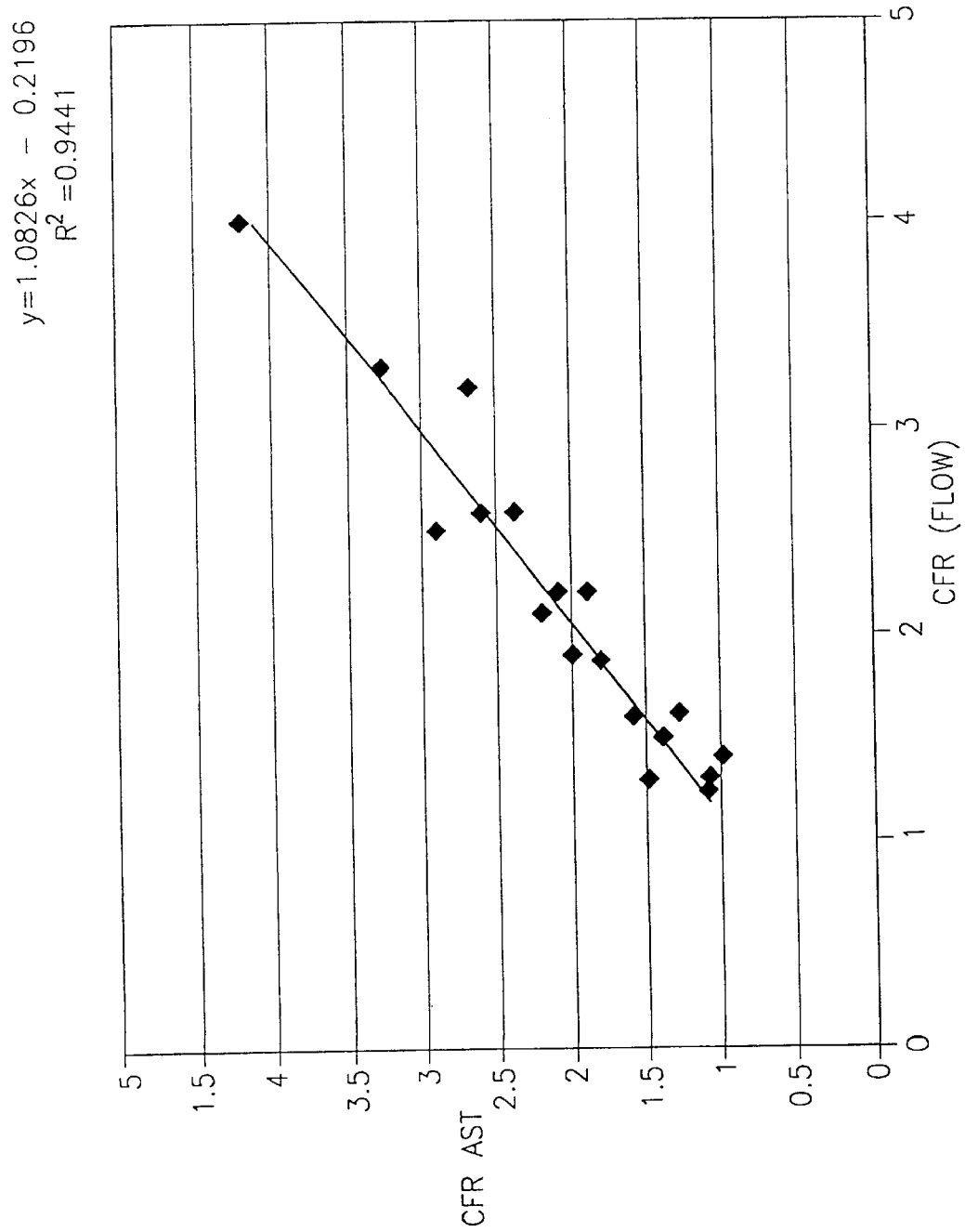
FIG. 38 In-vivo canine data of CFR –F which uses the Automatic Similar Transformation method and CFR flow.

Vasodilatory effect: Vasodilatation was achieved by intracoronary Papaverine injection. The response to Papaverine was immediate, reaching the max hyperemia after about 45 sec. The data is presented in Table 6 and FIGS. 37 and 38. All together, 22 stenoses were studied, all shown in FIG. 37. Very good correlation is observed between Automatic Similar Transformation (AST) method calculated parameters (CFR-AST) and the flow based CFR using the gold standard CardioMed flowmeter (A-CFR). As expected, low correlation is observed only in few cases of very light stenosis (25%), where the pressure gradient reaches the low limit of the method. In FIG. 38, 21 of 22 values are presented and regressed. Only one point is excluded, representing a stenosis<25%.

TABLE 6

AST-CFR/FFR calculated values compared to flow based CFR and FF pressure.

| | % | Values | | ASR Values | |
|---|---|---|---|---|---|
| Case # | Stenosis | FFR | CFR | FFR | CFR |
| Dog 1/ | 50% | 0.84 | 4 | 0.77 | 4.2 |
| 25 Kg | 75% | 0.64 | 2.6 | 0.64 | 2.4 |
|  | 90% | 0.42 | 1.6 | 0.41 | 1.3 |
|  | 99% | 0.3 | 1.4 | 0.29 | 1.0 |
| Dog 2/ | 60% | 0.78 | 3.2 | 0.77 | 2.7 |
| 22 Kg | 75% | 0.79 | 2.2 | 0.65 | 2.1 |
|  | 80% | 0.6 | 2.1 | 0.58 | 2.2 |
|  | ??? | 0.84 | 3.3 | 0.81 | 3.3 |
|  | 90% | 0.58 | 2.2 | 0.57 | 1.9 |
|  | 99% | 0.5 | 1.5 | 0.5 | 1.4 |
| Dog 3/ | 25% | 0.98 | 5.5 | 0.96 | 1.8 |
| 20 Kg | 50% | 0.76 | 1.9 | 0.61 | 2.0 |
|  | 75% | 0.54 | 1.6 | 0.49 | 1.6 |
|  | 75% | 0.74 | 1.87 | 0.6 | 1.8 |
|  | 90% | 0.6 | 1.3 | 0.55 | 1.5 |
|  | 99% | 0.43 | 1.3 | 0.4 | 1.1 |
| Dog 4/ | 25% | ? | 4.3 | 0.95 | 2.3 |
| 25 Kg | 25% | 0.52 | 4.0 | 0.67 | 4.4 |
|  | 50% | 0.87 | 2.5 | 0.89 | 2.9 |
|  | 75% | 0.48 | 2.57 | 0.47 | 2.6 |

TABLE 6-continued

AST-CFR/FFR calculated values compared to flow based CFR and FF pressure.

| Case # | % Stenosis | Values FFR | Values CFR | ASR Values FFR | ASR Values CFR |
|---|---|---|---|---|---|
| | 90% | 0.12 | 1.25 | 0.14 | 1.1 |
| | 99% | 0.46 | 1.2 | 0.42 | 1.3 |

Discussion: The significant difference (15–20 mm Hg) between the pressures measured by the fluid filled manometer and the Radi at the proximal point makes a direct estimation of the pressure gradient across the stenosis difficult. For this reason, the pressure difference was computed taking into account the change in aortic pressure. The mean pressure difference across the stenosis, denoted AP, is approximately 3 mm Hg. 2. The pressure difference across the stenosis, Ap(t), may be estimated from the volume flow rate (in short flow) Q(t), the minimal stenosis cross-sectional area A, and the (healthy) vessel cross-sectional area A, using the well-known Young-Tsai equation (this equation has been tested in vitro and ir and vivo in numerous cases):

$$\Delta p(t) = \frac{4K_\mu \mu}{\pi D^3} Q(t) + \frac{K_1 \rho}{2A_0^2}\left(\frac{A_0}{A_s} - 1\right)^2 Q(t)|Q(t)| + \frac{K_v \rho L_s}{A_0} \frac{dQ(t)}{dt} \quad (1)$$

Upon integration Eq. (1) over one heart beat one obtains:

$$\Delta P = \frac{4K_\mu \mu}{\pi D^3} \overline{Q} + \frac{K_1 \rho}{2A_0^2}\left(\frac{A_0}{A_s} - 1\right)^2 \overline{Q^2} \quad (2)$$

where a bar means averaging over a heartbeat. The Coefficient Kt is practically $$K_\mu = 32 \frac{0.83 L_s + 1.64 D_s}{D_0}\left(\frac{A_0}{A_s}\right)^2 \quad (3)$$

independent of geometry and can be approximated as 1.52. The coefficient ($L_s$—length of the stenosis, D, and $DO_s$—diameters corresponding to the areas A, and Ao, respectively). Unfortunately, the function of Q(t) is not known. For estimation of the Q2 term it is assumed that Q(t) may be approximated as Q(I+sin(27πt)), where Q is a constant $Q^2=1.5Q^2$ equal to mean flow. It follows then that (note the order in the averaging). The stenosis length Ls as well as Au are unknown. However as the linear Poiseuille term ((the first term in Eq. (2)) is small for typical stenosis, the representative values for the unknown parameters are taken: Ls=2 cm, Do=4 mm. Finally, it is assumed that blood viscosity u=0.004 again due to the smallness of the Poiseuille term, the exact value of p is not important).

For definiteness two cases were examined; 1) 50% diameter stenosis, i.e., $A_o/A_s=4$ and 2) 60% stenoisis. When there is 50% diameter stenosis, it was estimated that ΔP for various flow velocities u (Q=u*$A_o$).

TABLE 7

50% diameter stenosis.

| U (cm/s) | 6 | 12 | 18 | 24 | 30 | 36 | 42 | 48 |
|---|---|---|---|---|---|---|---|---|
| ΔP (mm Hg) | 1.4 | 3.4 | 5.9 | 9.0 | 12.6 | 16.8 | 21.6 | 26.9 |

TABLE 8

60% diameter stenosis, h/,4, = 6.25

| U (cm/s) | 6 | 12 | 18 | 24 | 30 | 36 | 42 | 48 |
|---|---|---|---|---|---|---|---|---|
| ΔP (mm Hg) | 3.55 | 8.8 | 15.7 | 24.4 | 34.7 | 46.7 | 60.5 | 75.9 |

In the above Japan results the following pressure differences across stenosis were measured: ΔPrest=3.4 mm Hg; ΔPvaso=19.7 mm Hg. As shown in Table 7 (50% stenosis') that corresponding to a vaue of ΔPrest=3.4 mm Hg there corresponds a value of velocity at rest Urest=12 cm/s and to ΔPvaso=19.7 mm there corresponds a value of velocity during vasodilatation: Uvaso=40 cm/s. Therefore, CFR=40/12=3.3. Similarly, using Table 8 (60% stenosis) Urest=6 cm/s, Uvaso=20 cm/s and again CFR=20/6=3.3.

During the experiment the velocity measured by the FlowWire in the above experiment was about 6 cm/s at rest and about 40 cm/s during vasodilatation. The measured percent stenosis was 50%. In this case, the velocity at rest is half the calculated velocity using pressure differences (Urest=12 cm/s). A possible explanation for this discrepancy is due to the misalignment of the FlowWire in the vessel.

The above results of the FlowWire measurements confirm the proposition that baseline flows both in the stenosed and healthy vessel are the same. Baseline flows before and after PTCA were 18 cm/s and hyperemic flow changed from 24 cm/s to 63 cm/s. FFR=0.55–0.59 hence, CFR/FFR= 2.26–2.42. CFR after PTCA equal to 63/24=2.62. The discrepancy is within 10%.

Simultaneous CFR and FFR measurements permit one to obtain additional information about the vascular bed. For example, in cases 4, 5 and 6. As in the previous report, one may use the Young and Tsai equation to calculate the flow in the stenosed blood vessel. In case 4, the stenosis parameters are in this case: 50% diameter stenosis, BAPV=16 cm/s, HAPV=44 cm:s, BPG=12 mm Hg, HPG=33 mm Hg., FFR=0.59–0.63. Due to change in aortic pressure during vasodilatation the HPG is calculated using the mean aortic pressure, measured at rest and FFR, as well. It was assumed that stenosis has a length of L=2 cm, artery diameter 3.0 mm, blood viscosity 0.0035. The results of the calculations are presented in Table. 9

TABLE 9

Calculations for LDA 50% diameter stenosis

| Velocity | 15 | 20 | 22 | 25 | 40 | 45 | 50 |
|---|---|---|---|---|---|---|---|
| Pressure Gradient (mm Hg) | 5.9 | 8.7 | 10.0 | 11.9 | 23.7 | 28.4 | 33.0 |

From Table 9, that the measured velocities are small for a 50% stenosis. In this case, the CFR, which corresponds to the measured pressure gradients at rest and during vasodilatation is equal to 50/25=2.0 (which is the value computed using the methods described herein AST CFR).

The measured hyperemic velocity corresponds to the measured hyperemic pressure gradient for a 52% stenosis, as shown in Table 10:

TABLE 10

Calculations for LDA 52% diameter stenosis

| Velocity | 15 | 20 | 22 | 25 | 40 | 44 | 50 |
|---|---|---|---|---|---|---|---|
| Pressure Gradient (mm Hg) | 7.1 | 10.5 | 11.9 | 14.3 | 28.6 | 33.1 | 40.5 |

As demonstrated in Table 10 the baseline:velocity measured by the FlowWire is too low for the measured pressure. The baseline velocity corresponding to the base pressure gradient is 22 cm/s and CFR is again 44/22=2.0. The ratio CFR/FFR=2.0/0.63=3.2 3 is reasonable and doesn't seem to point to any problem with the vascular bed.

In case 5, LDA stenosis, its parameters are: 50% diameter stenosis, BAPV=10 cm/s, HAPV=34 cm/s, BPG=12 mm Hg, HPG=34 mm Hg., FFR=0.66. Due to change in aortic pressure during vasodilatation, the HPG is calculated using mean aortic pressure, measured at rest. As in the previous case, stenosis length L=2 cm, artery diameter 3 mm, blood viscosity 0.0035. Results or the calculations are presented in Table. 11.

TABLE 11

Calculations for LDA 50% diameter stenosis

| Velocity | 10 | 15 | 18 | 20 | 30 | 35 | 37 |
|---|---|---|---|---|---|---|---|
| Pressure Gradient (mm Hg) | 5.6 | 9.4 | 12.0 | 13.8 | 24.7 | 31.2 | 34.0 |

The flow velocity at rest measured by FlowWire is too low for the measured pressure gradient, in this case also. The corresponding CFR=37/18=2 is close to the value 1.8 supplied by the AST-CFR method. The ratio CFR/FFR=2/0.66=3 is reasonable and doesn't seem to point to any problem with the vascular bed.

Case 6, RCA stenosis. Its parameters are: 25% diameter stenosis, BAPV=30 cm/s, HAPV=50 cm/s, BPG=5.7 mm Hg, HPG=15.9 mm Hg., FFR=0.83. Due to change in aortic pressure during vasodilatation the HPG is calculated using mean aortic pressure, measured at rest. Stenosis is L-2 cm, artery diameter 3 mm and blood viscosity at 0.0035. Results are presented in Table 12.

TABLE 12

Calculations for RCA 25% diameter stenosis

| Velocity | 50 | 60 | 75 | 100 | 130 |
|---|---|---|---|---|---|
| Pressure Gradient (mm Hg) | 4.28 | 5.45 | 7.4 | 11.2 | 16.5 |

The percent stenosis is too low for the measured velocities and the pressure gradients. The CRR corresponding to the measured pressure gradient is 130/60=2.17. This value again is in good agreement with the AST-CFR method. The following results were obtained were stenosis is 40%.

TABLE 13

Calculations for LDA 40% diameter stenosis

| Velocity | 25 | 27 | 30 | 40 | 50 | 55 | 60 |
|---|---|---|---|---|---|---|---|
| Pressure Gradient (mm Hg) | 5.2 | 5.76 | 6.65 | 9.95 | 13.8 | 15.9 | 18.2 |

In this case the CFR corresponding to the pressure gradient is 55/27=2.0, 10% less then the value calculated by the AST-CFR method. However, in this case where even a small error in the measured velocity or pressure gradient yields a 10–20% error in CFR. For example, in case 6, the HAPV (55 cm/s) and BAPV (27 cm/s) values were used instead of 50 cm/s and 30 cm/s as measured by Flow wire and obtain a CFR equal to 2.0 instead of 1.7. The ratio CFR/FFR lies between 2.0/0.83=2.4 and 2.2/0.83=2.65. These values are near the lower bound of values CFR/FFR for normal vascular bed. Thus, there is a systematic error in the Flow Wire velocity measurements at velocities lower than 15–20 cm/s.

Conclusion: The above results demonstrate that the AST-CFR method is an accurate and more precise measurement of stenosis.

EXAMPLE 3

In-vivo CFR-FFR Measurements in Swine

The goal of percutaneous coronary intervention (PC) is to reduce flow-limiting arterial obstruction. PC1 currently is guided by anatomic rather than flow assessment of lesion severity. Physiologic parameters such as Coronary Flow Reserve (CFR) and Fractional Flow reserve (FFR) more accurately describe the severity of flow reduction but are cumbersome to measure clinically. As demonstrated herein, the methods of this invention allow calculation of CFR and FFR directly from intraarterial pressure measurements.

Methods: In anesthetized pigs (30 kg.) following throacotomy an occluder and ultrasonic flow probe (distal, Transonics) were placed around the LAD. A solid state pressure guide wire (RADI Medical) and doppler flow wire (Endosonics) were placed in the LAD. Stenoses were established (30–70%)(n=IZ) and baseline and post-adenosine intracoronary pressure and flow measurements were made proximal, distal and during trans-lesional pullback. CFR and FFR were derived in real time from pressure via algorithm, and from actual measured 1 flows. In 9 patients pressure and flow wires were placed proximal and distal to isolated coronary lesion (50–90%), adenosine was administered and CFR and FFR were similarly derived.

The System which includes the AST as described above, was connected to an Astro-Med cathlab monitor for acquisition of the arterial pressure wave and the ECG. A modified Radi Pressure Wire Interface Box was used to allow high frequency data acquisition. The pressure signal was directly sampled by the AST System. A fluoroscopy system of the animal lab was used and a Transconic ultrasonic flowmeter (Model T206) with perivascular flowprobes (2, 3, and 4 mm). The flow signal was directly sampled by the AST System.

Animal Preparation: The pigs were anesthetized, the chest opened and the heart exposed. The LAD was then dissected in two separate sites to allow introduction of the perivascular flowprobe and the balloon occluder. One the preparation stage is over reference measurements are obtained. Then a series of occlusions is introduced by slowly inflating the balloon occluder. In each level of occlusion the required measurements for CFR/FFR calculations are obtained.

Vasolidation Effect: Vasolidation was achieved either by intracoronary Adenosine or intracoronary Papaverine injections. The effect of Papaverine is long (>3 min) but not different then the short effect of the Adenosine. Maximal hyperemia is achieved by both. When no effect was observed it was due to the compensatory vasolidation of the distal bed.

Figure 39:
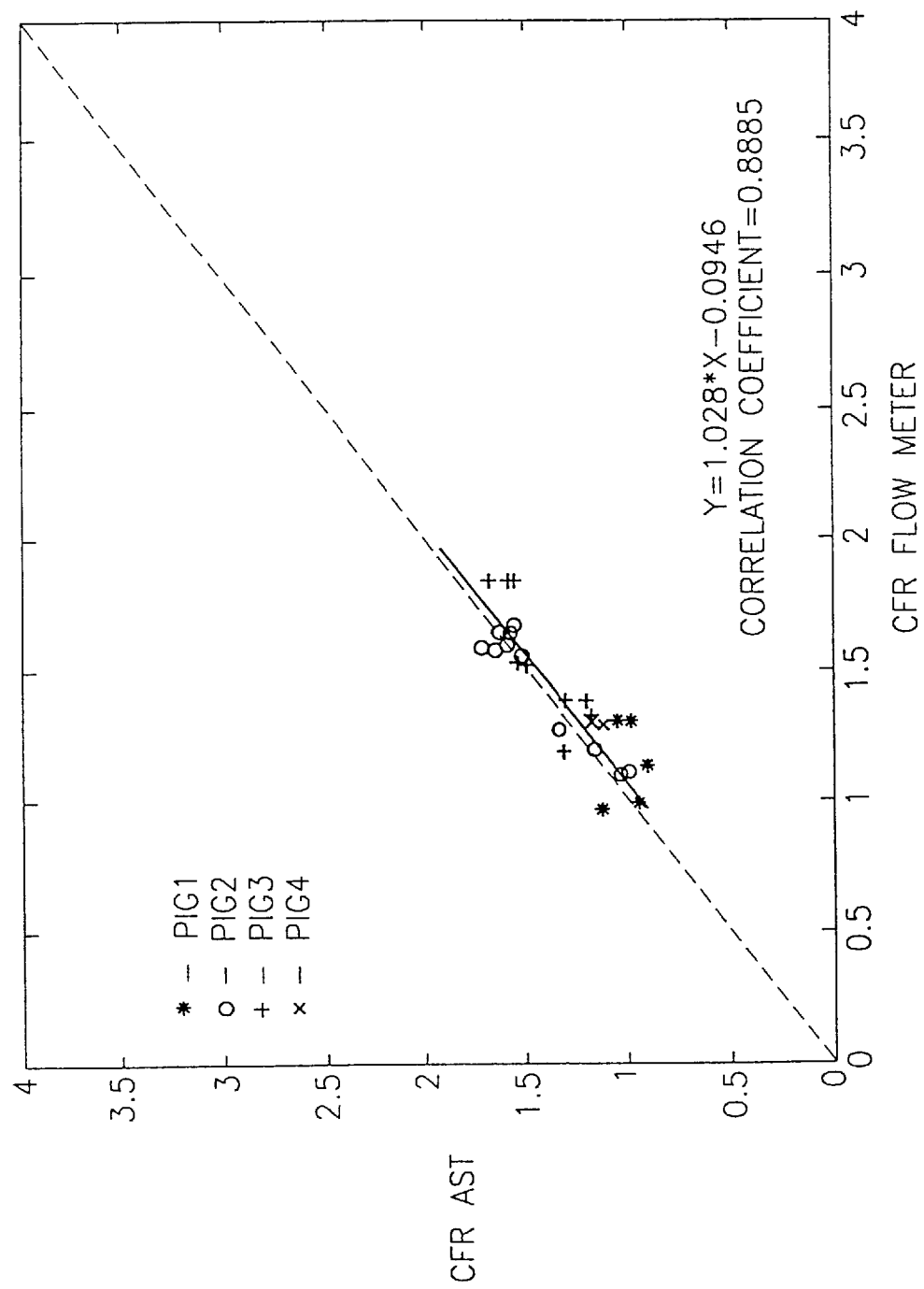
FIG. 39 In-vivo pig data of CFR –F which uses the Automatic Similar Transformation method and CFR flow.

The results are presented in Table 14 and FIG. 39.

|  | % Stenosis | BPG | HPG | AST-CFR | CFR Flow | FFR |
|---|---|---|---|---|---|---|
| Pig 1 | Ref | 12.4 | 12.0 | 0.97 | 1.0 | 0.7 |
| Pig 2 | Mild | 0.718 | 4.48 | 1.598 | 1.64 | 0.916 |
|  | Severe | 4.48 | 10.04 | 1.17 | 1.21 | 0.794 |
|  | Severe | 1.2 | 3.4 | 1.34 | 1.3 | 0.93 |
| Pig 3 | Severe | 5.6 | 7.57 | 1.4 | 1.47 | 0.89 |
|  | Severe | 4.7 | 6.4 | 1.15 | 1.18 | 0.9 |

BPG: Base Pressure Gradient across stenosis at rest.
HPG: Pressure gradient across stenosis at vasolidation.

In all pigs a close correlation was observed for pressure derived CFR ($CFR_P$) and FFR versus CFR ($CFR_F$) and FFR derived from actual flow determination ($CFR_P$=1.03, $CFR_F$=0.095, R=0.89). In the human subject the CFR and FFR correlated closely with flow velocity derived CFR and FFR ($CFR_P$=1.06, $CFR_F$=0.100, R=0.85).

Therefore, intraluminal pressured derived coronary flow indices correlate closely with indices derived from Doppler flow data. Derivation of these indices from pressure is simpler and more reliable as this method is independent of velocity profiles which may be individually variable.

EXAMPLE 4

In-vivo Results Obtained Based on the Automatic Similar Transformation Methods

The following results were obtained using the automatic similar transformation (AST) method described above.

| % stenosis | CFR AST (mean pulse) | $\sqrt{HPG/BPG}$ |
|---|---|---|
| Dog 1. | | |
| 50 | 2.93 | 2.9 |
| 75 | 2.83 | 2.86 |
| 90 | 1.4 | 1.35 |
| 99 | 1.04 | 1.03 |
| Dog 2. | | |
| 60 | 2.7 | 2.5 |
| 75 | 2.1 | 2.05 |
| 80 | 2.26 | 2.17 |
| ?? | 2.45 | 2.31 |
| 90 | 1.85 | 1.8 |
| 99 | 1.7 | 1.68 |
| Dog 3. | | |
| 50 | 1.8 | 1.92 |
| ?? | 1.7 | 1.68 |
| 75 | 1.5 | 1.45 |
| 90 | 1.5 | 1.49 |
| 99 | 1.1 | 1.11 |

-continued

| % stenosis | CFR AST (mean pulse) | $\sqrt{HPG/BPG}$ |
|---|---|---|
| Dog 4. | | |
| 25–50 | 4.3 | 4.26 |
| 50 | 3 | 2.9 |
| 75 | 2.5 | 2.36 |
| 90 | 1.1 | 1.1 |
| 99 | 1.2 | 1.22 |

EXAMPLE 5

VBI Verification

The vascular bed index is defined as VBI=$(4 \mu Q/(P\pi d^3))$=$(\mu u)/(Pd)$, where P—pressure, d—artery diameter, $\mu$—dynamic viscosity. The vascular bed index is the same for mother and daughter arteries, if the ratio of the diameters of these arteries follows Murray's law (the Murray law discussed in the paper Kassab G. S., Fung Y. B. The pattern of coronary arteriolar bifurcations and the uniform shear hypothesis.). The VBI using human data obtained was calculated.

Figure 42A:
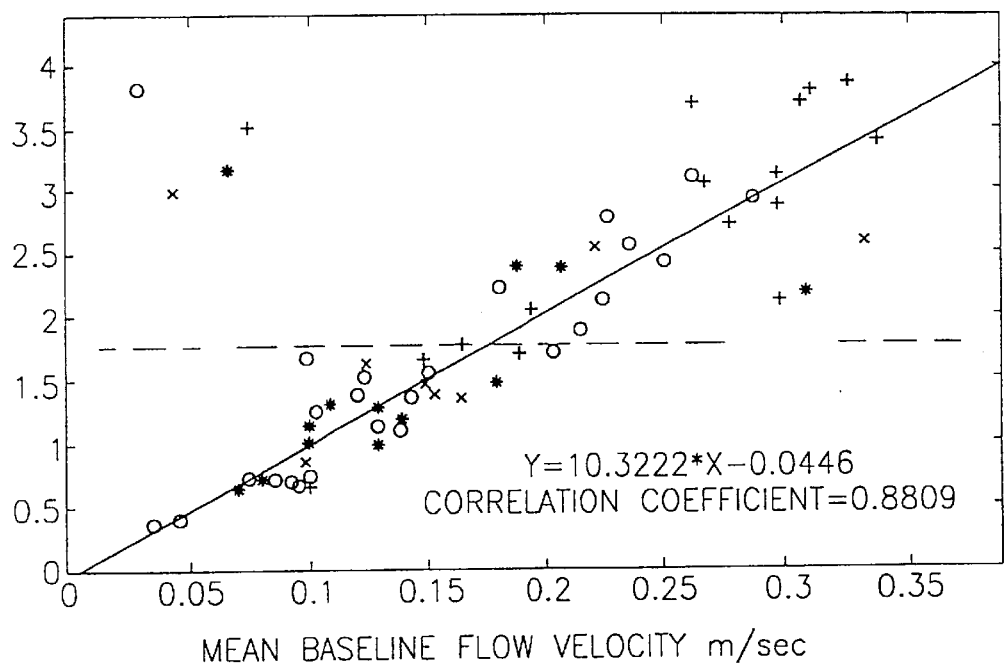
FIG. 42 Results of VBI calculation based on human data.
Figure 42B:
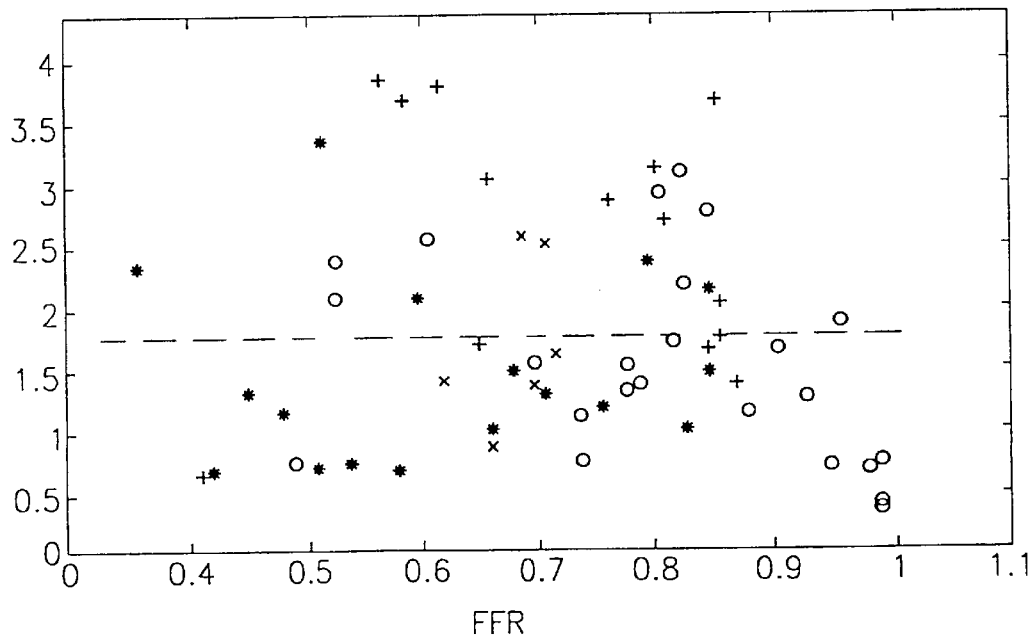
Figure 42C:
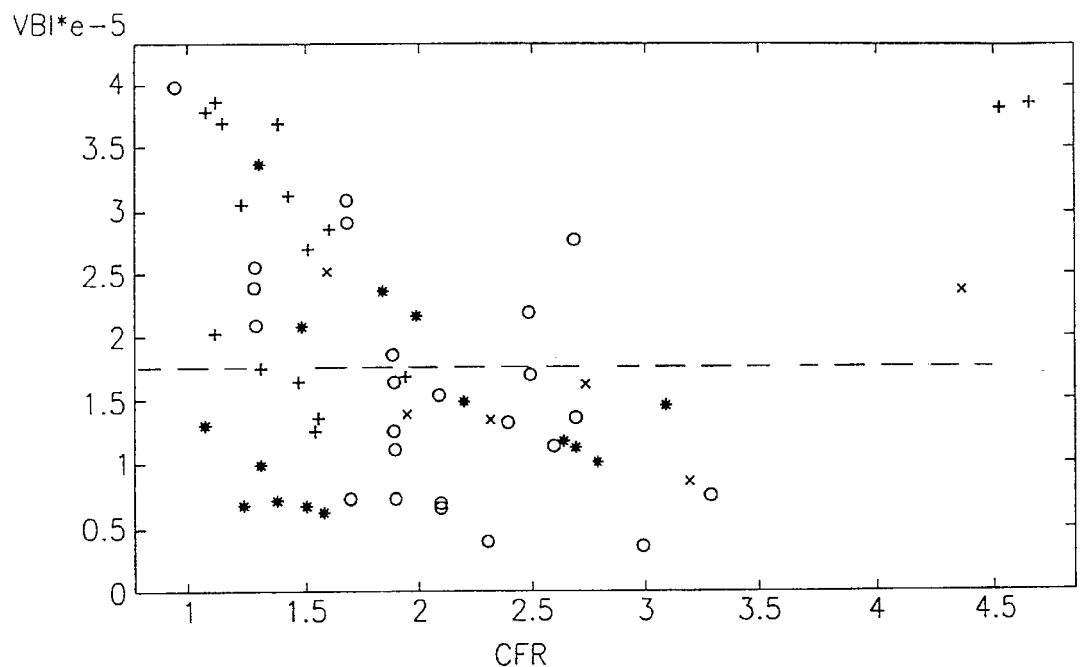
Figure 42D:
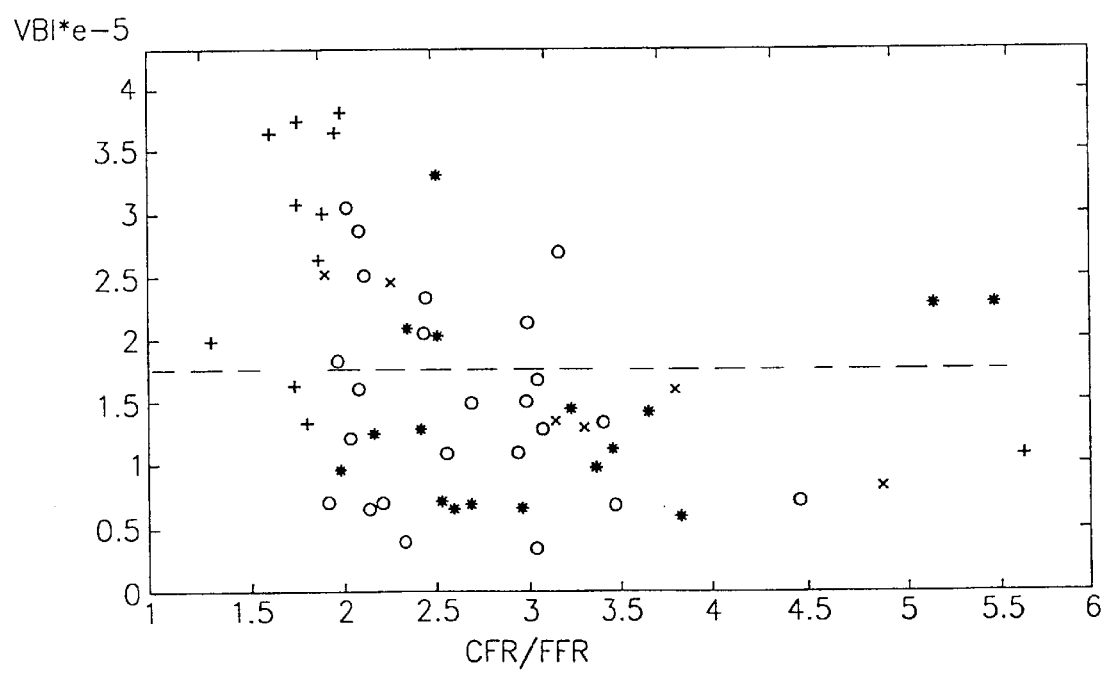

The results are present in FIG. 43a–d. There is a strong correlation between VBI and mean flow velocity at rest with correlation coefficient R=0.926 (FIG. 42a.). The mean value of the VBI=$1.7 \cdot 10^{-5}$. The VBI is independent of the CFR, FFR and the ratio CFR/FFR (FIG. 42b–d.). Hence, the VBI reflects another, then CFR and FFR, features of the vascular bed. The low values of VBI indicate "slow flow" cases.

EXAMPLE 6

Verification of CFR0 (the ratio CFR/FFR)

The calculated values of the CFR/FFR ratio are compared with in vivo test results. The results are presented and summarized in the following Table 15:

| | *Mean CFR/FFR | Mean CFR/FFR flow meter (test results) | Standard Deviation | Standard Deviation (flow meter) |
|---|---|---|---|---|
| Dog1 | 4.0925 | 4.03 | 0.334 | 0.7366 |
| Dog2 | 3.3 | 3.4983 | 0.4192 | 0.3065 |
| Dog3 | 2.834 | 2.662 | 0.1769 | 0.2225 |
| Dog4 | 4.966 | 5.784 | 1.9033 | 3.3089 |

*CFR and FFR are calculated using the Automatic Similar Transformation method

Standard deviation of the CFR/FFR for every dog is also presented in the Table 15. The results for first 3 dogs confirm that CFR/FFR ratio is independent from % stenosis. In the Dog 4 case the standard deviation is high. It is explained by the large disperse of ratio values.

What is claimed is:

1. A method for determination of coronary flow reserve in a stenotic vessel, the method comprising the steps of:
   providing an apparatus adapted to measure pressure across a blood vessel obstruction; and
   determining said coronary flow reserve from said pressure measurements.

2. The method of claim 1, further including the step of measuring aortic pressure and pressure distal to said obstruction simultaneously by said apparatus having a fluid filled manometer and a pressure transducer, respectively.

3. The method of claim 1, further including the steps of:
measuring aortic pressure with said apparatus having a fluid filled manometer;
measuring pressure across said obstruction with said apparatus having a moving pressure transducer; and
synchronizing said pressure measurements with said apparatus having an ECG.

4. The method of claim 1, further including the steps of:
measuring pressure across said obstruction with said apparatus having a moving pressure transducer; and
synchronizing said pressure measurements with said apparatus having an ECG.

5. The method of claim 1, further including the steps of:
measuring aortic pressure with said apparatus having a fluid filled manometer;
measuring pressure across said obstruction with said apparatus having a moving pressure transducer; and
synchronizing said pressure measurements with said moving pressure transducer.

6. The method of claim 1, further including the steps of:
measuring aortic pressure with said apparatus having a fluid filled manometer;
measuring pressure across said obstruction with said apparatus having a moving pressure transducer; and
synchronizing said pressure measurements with said fluid filled manometer.

7. The method of claim 1 wherein said obstruction is a natural stenosis.

8. The method of claim 1 wherein said obstruction is an artificial balloon obstruction.

9. A method for determination of coronary flow reserve in a blood vessel having an obstruction, the method including the steps of:
providing an apparatus adapted to measure pressure across said obstruction;
measuring pressures across said obstruction wherein an aortic pressure and a pressure distal to said obstruction are simultaneously measured by said apparatus having a fluid filled manometer and a pressure transducer, respectively; and
determining coronary flow reserve from said pressure measurements.

10. A method for determination of coronary flow reserve in a blood vessel having an obstruction, the method including the steps of:
providing an apparatus adapted to measure pressure across said obstruction;
measuring an aortic pressure with said apparatus having a fluid filled manometer for the aortic pressure;
measuring pressure across the obstruction with said apparatus having a moving pressure transducer; and
determining coronary flow reserve from said pressure measurements.

11. A method for determination of coronary flow reserve in a blood vessel having an obstruction, the method including the steps of:
providing an apparatus adapted to measure pressure across said obstruction;
measuring an aortic pressure with said apparatus having a fluid filled manometer for the aortic pressure;
measuring pressure across the obstruction with said apparatus having a moving pressure transducer;
synchronizing said pressure measurements with said apparatus having an ECG; and
determining coronary flow reserve from said pressure measurements.

12. A method for determination of coronary flow reserve in a blood vessel having an obstruction, the method including the steps of:
providing an apparatus adapted to measure pressure across said obstruction;
measuring an aortic pressure with said apparatus having a fluid filled manometer for the aortic pressure;
measuring pressure across said obstruction with said apparatus having a moving pressure transducer;
synchronizing said pressure measurements with said moving pressure transducer; and
determining coronary flow reserve from said pressure measurements.

13. A method for determination of coronary flow reserve in a blood vessel having an obstruction, the method including the steps of:
providing an apparatus adapted to measure pressure across said obstruction;
measuring an aortic pressure with said apparatus having a fluid filled manometer for the aortic pressure;
measuring pressure across the obstruction with said apparatus having a moving pressure transducer;
synchronizing said pressure measurements with said fluid filled manometer; and
determining coronary flow reserve from said pressure measurements.

14. A sensor apparatus for determination of coronary flow reserve in a stenotic vessel comprising:
at least one pressure sensor, wherein said at least one pressure sensor includes a plurality of pressure sensors adapted to measure pressure distal and proximal to an obstruction; and
a processor for determining coronary flow reserve from said pressure measurements.

15. A sensor apparatus for determination of coronary flow reserve in a stenotic vessel comprising:
at least one pressure sensor, wherein said at least one pressure sensor includes a fluid filled manometer and a pressure transducer adapted to simultaneously measure aortic pressure and pressure distal to said obstruction, respectively; and
a processor for determining coronary flow reserve from said pressure measurements.

16. A method for determination of diastole to systole velocity ratio in a stenotic vessel, the method comprising the steps of:
providing an apparatus adapted to measure pressure distal and proximal to a stenosis;
measuring aortic pressure with said apparatus having a fluid filled manometer;
measuring pressure across said stenosis with said apparatus having a moving pressure transducer;
synchronizing said pressure measurements with said apparatus having an ECG; and
determining diastole to systole velocity ratio from said pressure measurements.

17. A sensor apparatus for determination of coronary flow reserve in a stenotic vessel comprising:
at least one pressure sensor for obtaining pressure measurements, wherein said at least one pressure sensor comprises:

a fluid filled manometer adapted to measure aortic pressure; and a pressure transducer adapted to measure pressure across said obstruction;

an ECG cooperatively connected to said at least one pressure sensor for synchronization of said pressure measurements; and a processor for determining coronary flow reserve from said pressure measurements.

18. A sensor apparatus for determination of coronary flow reserve in a stenotic vessel comprising:

at least one pressure sensor for obtaining pressure signals, wherein said at least one pressure sensor includes a moving pressure transducer adapted to measure pressure across an obstruction;

an ECG cooperatively connected to said at least one pressure sensor for synchronization of said pressure signals; and a processor for determining coronary flow reserve from said pressure signals.

19. A sensor apparatus for determination of coronary flow reserve in a blood vessel having an obstruction, the apparatus comprising:

at least one pressure sensor adapted to measure pressure across said obstruction, wherein said at least one pressure sensor comprises:

a fluid filled manometer adapted to measure aortic pressure; and a pressure transducer adapted to measure pressure across said obstruction;

an ECG for synchronization of said pressure measurements; and a processor for determining coronary flow reserve from said pressure measurements.

20. A sensor apparatus for determination of coronary flow reserve in a blood vessel having an obstruction, the apparatus comprising:

at least one pressure sensor adapted to measure pressure across said obstruction, wherein said at least one pressure sensor comprises:

a fluid filled manometer adapted to measure aortic pressure; and a pressure transducer adapted to measure pressure across said obstruction, wherein said pressure measurements are used for synchronization of said pressure measurements; and a processor for determining coronary flow reserve from said pressure measurements.

21. A sensor apparatus for determination of coronary flow reserve in a blood vessel having an obstruction, the apparatus comprising:

at least one pressure sensor adapted to measure pressure across said obstruction, wherein said at least one pressure sensor comprises:

a fluid filled manometer adapted to measure aortic pressure; and a pressure transducer adapted to measure pressure across said obstruction, wherein said fluid filled manometer pressure measurements are used for synchronization of said pressure measurements; and a processor for determining coronary flow reserve from said pressure measurements.

22. A sensor system comprising:

at least one sensor adapted to measure pressure in a tubular conduit across and obstruction; and means for determining coronary flow reserve together with fractional flow reserve in the same blood vessel or tubular conduit without stenosis and analysis of their correlation.

23. A sensor system comprising:

at least one sensor adapted to measure pressure in a tubular conduit across and obstruction; and means for determining coronary flow reserve together with fractional flow reserve in the same blood vessel without stenosis and analysis of their correlation for estimation of vascular bed conditions or an aneurysm.

* * * * *